Figure 1A:
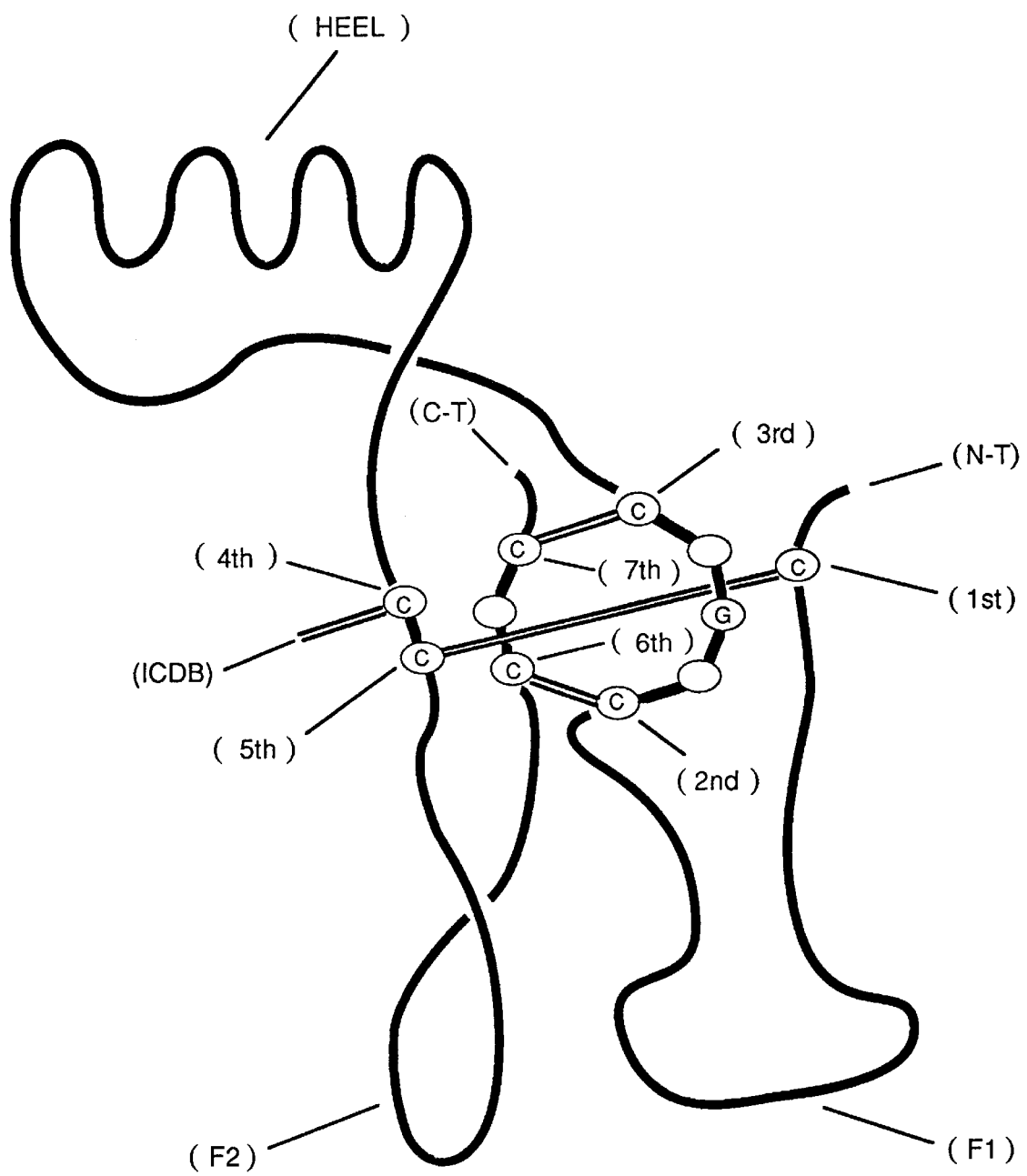

United States Patent [19]
Keck et al.

[11] Patent Number: 6,040,431
[45] Date of Patent: *Mar. 21, 2000

[54] SINGLE CHAIN ANALOGS OF THE TGF-β SUPERFAMILY (MORPHONS)

[75] Inventors: Peter C. Keck, Millbury; John E. Smart, Weston, both of Mass.

[73] Assignee: Stryker Corporation, Kalamazoo, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/478,097

[22] Filed: Jun. 7, 1995

[51] Int. Cl.⁷ ............................ C12N 15/12; C07K 14/51

[52] U.S. Cl. ............................. 530/399; 530/350

[58] Field of Search .................... 530/350, 399; 435/69.1, 69.4, 320.1, 325; 536/23.5

[56] References Cited

U.S. PATENT DOCUMENTS

| | | |
|---|---|---|
| 4,686,283 | 8/1987 | Nestor, Jr. et al. . |
| 4,816,442 | 3/1989 | McPherson et al. . |
| 4,863,899 | 9/1989 | Todaro . |
| 4,863,902 | 9/1989 | Amagase et al. . |
| 4,874,746 | 10/1989 | Antoniades et al. . |
| 4,929,442 | 5/1990 | Powell . |
| 4,968,590 | 11/1990 | Kuberasampath et al. . |
| 5,008,240 | 4/1991 | Bentz et al. . |
| 5,011,691 | 4/1991 | Oppermann et al. . |
| 5,013,649 | 5/1991 | Wang et al. . |
| 5,037,643 | 8/1991 | Green . |
| 5,055,447 | 10/1991 | Palladino et al. . |
| 5,061,786 | 10/1991 | Burnier et al. . |
| 5,091,513 | 2/1992 | Huston et al. . |
| 5,104,977 | 4/1992 | Sporn et al. . |
| 5,108,922 | 4/1992 | Wang et al. . |
| 5,108,989 | 4/1992 | Amento et al. . |
| 5,118,791 | 6/1992 | Burnier et al. . |
| 5,120,535 | 6/1992 | Marquardt et al. . |
| 5,141,905 | 8/1992 | Rosen et al. . |
| 5,187,076 | 2/1993 | Wozney et al. . |
| 5,258,498 | 11/1993 | Huston et al. . |
| 5,266,683 | 11/1993 | Oppermann et al. . |
| 5,284,756 | 2/1994 | Grinna et al. . |
| 5,316,921 | 5/1994 | Godowski et al. . |
| 5,322,933 | 6/1994 | Davies . |
| 5,804,416 | 9/1998 | Wolfman et al. . |

FOREIGN PATENT DOCUMENTS

| | | |
|---|---|---|
| 0 132 021 | 1/1985 | European Pat. Off. . |
| 0 433 225 A1 | 6/1991 | European Pat. Off. . |
| WO 84/01106 | 3/1984 | WIPO . |
| WO 88/05789 | 8/1988 | WIPO . |
| WO 88/09344 | 12/1988 | WIPO . |
| WO 89/09788 | 10/1989 | WIPO . |
| WO 90/11366 | 10/1990 | WIPO . |
| WO 90/14359 | 11/1990 | WIPO . |
| WO 91/04274 | 4/1991 | WIPO . |
| WO 91/05565 | 5/1991 | WIPO . |
| WO 91/05802 | 5/1991 | WIPO . |
| WO 92/07073 | 4/1992 | WIPO . |
| WO 93/05751 | 4/1993 | WIPO . |
| WO 94/15966 | 7/1994 | WIPO . |
| WO 94/17099 | 8/1994 | WIPO . |

OTHER PUBLICATIONS

Amberg et al. (19 ) "SurfZAP Vector: Linking Phenotype to Genotype for Phagemid Display Libraries," *Strategies in Molecular Biology* 6: 2–6.

Basler et al. (1993) "Control of Cell Pattern in the Neutral Tube: Regulation of Cell Differentiation by Dorsalin–1, a Novel TGFβ Family Member," *Cell* 73: 687–702.

Braun et al. (1988) "Transforming Growth Factor β mRNA Increases During Liver Regeneration: A Possible Paracrine Mechanism of Growth Regulation," *Proc. Natl. Acad. Sci. USA* 85: 1539–1543.

Brunner et al. (1989) "Site–directed Mutagenesis of Cysteine Residues in the Pro Region of the Transforming Growth Factor β1 Precursor," *Journal of Biological Chemistry* 264: 13660–13664.

Celeste et al. (1990) "Identification of Transforming Growth Factor β Family Members Present in Bone–inductive Protein Purified from Bovine Bone," *Proc. Natl. Acad. Sci. USA* 87: 9843–9847.

Daopin et al. (1992) "Crystal Structure of Transforming Growth Factor–β2: An Unusual Fold for the Superfamily," *Science* 257: 369–373.

Ealick et al. (1991) "Three–Dimensional Structure of Recombinant Human Interferon–γ" *Science* 252: 698–702.

Griggs et al. (1992) "The N–terminus and C–terminus of IFN–γ are Binding Domains for Cloned Soluble IFN–γ Receptor," *Journal of Immunology* 149: 517–520.

Gruppuso et al. (1990) "Transforming Growth Factor Receptors in Liver Regeneration Following Partial Hepatectomy in the Rat," *Cancer Research* 50: 1464–1469.

Gruppuso et al. (1991) "Fetal Growth Factors as Determinants of Intrauterine Hepatic Growth," *Diabetes* 40: 51–55.

Kulkarni et al. (1993) "Transforming Growth Factor $β_1$ Null Mutation in Mice Causes Excessive Inflammatory Response and Early Death," *Proc. Natl. Acad. Sci. USA* 90: 770–774.

Ibáñez et al. (1993); "An Extended Surface of Binding to Trk Tyrosine Kinase Receptors in NGF and BDNF Allows the Engineering of a Multifunctional Pan–neurotrophin," *EMBO Journal* 12: 2281–2293.

(List continued on next page.)

*Primary Examiner*—Marianne P. Allen
*Attorney, Agent, or Firm*—Testa, Hurwitz & Thibeault, LLP

[57] ABSTRACT

Disclosed are a family of single-chain polypeptide constructs designed to agonize or mimic members of the TGF-β superfamily by binding to a cell surface receptor complementary to the superfamily member. The single-chain constructs of the invention called "morphons" contain in a single biologically active subunit interacting finger and heel regions which together define a tertiary protein structure complimentary to the ligand binding surface of a receptor that binds a TGF-β superfamily member. Also disclosed are truncated versions of the morphon constructs. Methods are disclosed for making and using single-chain morphons that have binding affinity for predetermined receptors of the TGF-β superfamily.

9 Claims, 23 Drawing Sheets

OTHER PUBLICATIONS

Lee, S. (1991) "Expression of Growth/Differentiation Factor 1 in the Nervous System: Conservation of a Bicistronic Structure," *Biochemistry* 88: 4250–4254.

Legerski et al. (1992) "Molecular Cloning and Characterization of a Novel Rat Activin Receptor," *Biochemical and Biophysical Research Communications* 183: 672–679.

Lin et al. (1993) "GDNF: A Glial Cell Line–Derived Neurotrophic Factor for Midbrain Dopaminergic Neurons," *Science*.260: 1130–1132.

Lowman et al. (1991) "Selecting High–Affinity Binding Proteins by Monovalent Phage Display," *Biochemistry* 30: 10832–10838.

Lyons, et al. (1989) "Vgr–1, A Mammalian Gene Related to Xenopus Vg–1, is a Member of the Transforming Growth Factor β Gene Superfamily," *Proc. Natl. Acad. Sci. USA* 86: 4554–4558.

Marks et al. (1992) "Molecular Evolution of Proteins on Filamentous Phage," *Journal of Biological Chemistry* 267: 16007–16010.

Massagué, J. (1987) "The TGF–β Family of Growth and Differentiation Factors," *Cell* 49: 437–438.

Massagué, J. (1992) "Receptors for the TGF–β Family," *Cell* 69: 1067–1070.

McCafferty et al. (1990) "Phage Antibodies: Filamentous Phage Displaying Antibody Variable Domains," *Nature* : 348: 552–554.

McDonald et al. (1991) "New Protein Fold Revealed by a 2.3–Å Resolution Crystal Structure of Nerve Growth Factor," *Nature* 354: 411–414.

McDonald et al. (1993) "A Structural Superfamily of Growth Factors Containing a Cysteine Knot Motif," *Cell* 73: 421–424.

McPherron et al. (1993) "GDF–3 and GDF–9: Two New Members of the Transforming Growth Factor–β Superfamily Containing a Novel Pattern of Cysteines," *The Journal of Biological Chemistry* 268: 3444–3449.

Mead et al. (1989) "Transforming Growth Factor α may be a Physiological Regulator of Liver Regeneration by Means of an Autocrine Mechanism," *Proc. Natl. Acad. Sci. USA* 86: 1558–1562.

Miyazono et al. (1993) "Transforming Growth Factor–β: Latent Forms, Binding Proteins and Receptors," *Growth Factors* 8 : 11–22.

Oefner et al. (1992) "Crystal Structure of Human Platelet–derived Growth Factor BB" *The EMBO Journal* 11: 3921–3926.

Ozkaynak, et al. (1990) "OP–1 cDNA encodes an osteogenic protein in the TGF–β Family" *The EMBO Journal* 9: 2085–2093.

Pepinsky et al. (1988) "Proteolytic Processing of Mullerian Inhibiting Substance Produces a Transforming Growth Factor–β–like Fragment," *Journal of Biological Chemistry* 263: 18961–18964.

Qian et al. (1992) "Identification of a Structural Domain that Distinguishes the Actions of the Type 1 and 2 Isoforms of Transforming Growth Factor β on Endothelial Cells," *Proc. Natl. Acad. Sci. USA* 89: 6290–6294.

Schlunegger et al. (1990) "An Unusual Feature Revealed by the Crystal Structure at 2.2Å Resolution of Human Transforming Growth Factor–β2," *Nature* 358: 430–434.

Smith et al. (1990) "Automatic Generation of Primary Sequence Patterns From Sets of Related Protein Sequences," *Proc. Natl. Acad. Sci. USA* 87: 118–122.

Wells et al. "Optimizing Binding and Catalysis by Phage Display," *Advances in Gene Technology: Protein Engineering and Beyond* pp. 105.

Wharton et al. (1991) "Drosophila 60A Gene, Another Transforming Growth Factor β Family Member, is Closely Related to Human Bone Morphogenetic Proteins," *Proc. Natl. Acad. Sci USA* 88: 9214–9218.

Honigwachs–Sha 'Anani et al. "Restrictin–P: The First Member of a Putative Family of Novel Inhibitors", *Annals New York Academy of Sciences* pp. 287–297.

FIG. 5A

| | | BETA | | | | | | | | | HELIX | | | | | | | | LOOP | | | | | | | | | BETA | | | | | RING KNOT_A | | |
|---|---|---|---|---|---|---|---|---|---|---|---|---|---|---|---|---|---|---|---|---|---|---|---|---|---|---|---|---|---|---|---|---|---|---|---|
| | 1 | | | | | | | | | 10 | | | | | | | | | 20 | | | | | | | | | 30 | | | | | | | |
| | K | | | | | | | | | | | | | | | | | | FINGER 1 | | | | | | | | | | | | | | | | |

TGF-β Subgroup
TGF-β1:   C C V R Q L Y I D F R K D L G W K - W I H E P K G Y H A N F C L G P C
TGF-β2:   C C V R P L Y I D F R Q D L G W K - W I H E P K G Y N A N F C A G A C
TGF-β3:   C C L R P L Y I D F R Q D L G W K - W V H E P K G Y Y A N F C S G P C
TGF-β4:   C C V R P L Y I D F R R D L G W K - W I H E P M G Y E A N F C M G P C
TGF-β5:   C C V K P L Y I D F R Q D L G W K - W I H E P K G Y Y A N F C L G P C
Pattern:  C C V R P L Y I D F R x D L G W K - W I H E P K G Y x A N F C x G x C Vg/dpp Subgroup
dpp:      C R R H S L Y V D F S - - D V G W - D W I V A P P G Y D A Y Y C H G K C
Vg-1:     C K K R H L Y V E F K - - D V G W - Q N W V I A P Q G Y M A N Y C Y G E C
Vgr-1:    C K K R H L Y V S F Q - - D L G W - Q D W I I A P K G Y A A N Y C D G E C
60A:      C Q M R Q T H V D F K - - D V G W - D D W I I A P L G Y E A Y H C E G L C
BMP-2A:   C K R H P L Y V D F S - - E I G W - N D W I V A P P G Y Q A F Y C H G D C
BMP-2B/BMP-4: C R R H S L Y V D F S - - D V G W - N D W I V A P P G Y H A F Y C H G E C
DORSALIN: C A R R Y L K V D F A - - D I G W - S E W I I A P K G Y A A N Y C D G E C
BMP-3:    C K K H E L Y V S F Q - - D L G W - Q D W I I A P K G Y A A N Y C D G E C
BMP-5:    C K K H E L Y V S F R - - D L G W - Q D W I I A P E G Y S A Y Y C E G E C
BMP-6:    C R R H S L Y V D F S - - D V G W - L D W I I A P Q G Y A A Y Y C E G E C
OP-1/BMP-7: C K K H E L Y V S F R - - D L G W - D D W I I A P Q G Y A A Y Y C E G E C
OP-2:     C R K H E L Y V S F Q - - D L G W - S D W I I A P A G Y Y A Y Y C A G E C
OP-3:     C R R H S L Y V D F R - - D L G W - D D W I I A P P G Y X A d Y C r G k C
Pattern:  C x R H x L Y V D F x - - D x G W - x D W I x A P x G Y x A x Y C x G x C GDF Subgroup
GDF-1:    C R T R R L H V S F R - - E V G W - H R W V I A P R G F L A N F C Q G T C
GDF-3:    C H R H Q L F I N F Q - - D L G W - H K W V I A P K G F M A N Y C H G E C
GDF-9:    C E L H D F R L S F S - - Q L K W - D N W I V A P H R Y N P R Y C K G D C
Pattern:  C r x r r L x x f x - - x r x W - x r W x a

FIG. 5B

| | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| TGF-β Subgroup | | | | | | | | | | | | | | | | | | | | | | | | | | | | | | | | | |
| TGF-β1: | P | Y | I | W | S | - | - | - | - | - | L | D | T | Q | Y | S | K | V | L | A | L | Y | N | Q | H | N | P | - | G | A | S | A | A | P | C |
| TGF-β2: | P | Y | L | W | S | - | - | - | - | - | S | D | T | Q | H | S | R | V | L | L | Y | N | I | H | N | P | - | E | A | S | A | S | P | C |
| TGF-β3: | P | Y | L | R | S | - | - | - | - | - | A | D | T | T | H | S | T | V | L | G | L | Y | N | T | L | N | P | - | E | A | S | A | S | P | C |
| TGF-β4: | P | Y | I | W | S | - | - | - | - | - | A | D | T | Q | H | S | K | V | L | A | L | Y | N | Q | H | N | P | - | G | A | S | A | A | P | C |
| TGF-β5: | P | Y | I | W | S | - | - | - | - | - | M | D | T | Q | Y | S | K | V | L | A | L | Y | N | Q | H | N | P | - | G | A | S | A | A | P | C |
| Pattern: | P | Y | c | W | s | - | - | - | - | - | x | D | T | Q | Y | s | x | V | L | a | L | Y | N | x | H | N | P | - | x | A | S | A | j | P | C |
| Vg/dpp Subgroup | | | | | | | | | | | | | | | | | | | | | | | | | | | | | | | | | |
| dpp: | P | F | P | L | A | D | H | F | - | - | N | S | T | N | H | A | V | V | Q | T | L | V | N | S | V | N | P | - | G | K | V | P | K | A | C |
| Vg-1: | P | Y | P | L | L | T | E | H | L | - | N | G | A | T | N | H | A | I | L | Q | T | L | M | N | M | E | P | - | E | D | I | P | L | P | C |
| Vgr-1: | S | F | P | L | R | S | A | H | M | - | N | A | T | N | H | A | I | V | Q | T | L | V | N | L | V | N | P | - | E | Y | K | P | K | P | C |
| 60A: | N | F | P | L | N | A | H | M | L | - | T | P | T | N | H | A | T | I | Q | S | L | L | N | L | V | N | P | - | K | K | K | I | P | K | C |
| BMP-2A: | F | F | P | L | A | D | D | H | V | - | N | T | T | N | H | A | I | V | Q | T | L | V | N | S | V | N | P | - | S | K | I | P | K | A | C |
| DORSALIN: | F | F | P | L | A | D | H | H | L | - | T | H | T | N | H | A | I | V | Q | T | L | L | N | Y | V | N | P | - | K | I | P | P | E | P | C |
| BMP-2B/BMP-4: | F | F | P | M | P | K | S | L | M | - | N | K | T | N | K | A | I | V | Q | T | L | V | N | H | M | N | P | - | S | S | I | P | K | P | C |
| BMP-3: | Q | F | P | L | N | A | H | M | N | - | T | P | T | N | H | A | I | V | Q | T | L | L | N | R | V | N | P | - | D | P | G | H | V | P | P |
| BMP-5: | S | F | P | L | N | A | H | M | M | - | N | A | T | N | H | A | I | V | Q | T | L | V | H | L | M | N | P | V | E | Y | T | V | P | K | C |
| BMP-6: | S | F | P | L | D | S | C | M | - | - | N | S | T | N | H | A | T | I | H | T | L | L | N | H | L | N | P | - | N | A | I | H | P | K | C |
| OP-1/BMP-7: | A | F | P | L | N | S | Y | M | - | - | N | A | T | N | H | A | I | V | Q | T | L | V | N | I | M | K | P | - | E | T | V | P | K | A | C |
| OP-2: | S | F | P | L | D | S | C | M | - | - | N | K | T | N | K | A | T | V | Q | T | L | L | N | M | K | K | P | - | N | A | I | P | K | V | C |
| OP-3: | H | Y | P | L | N | S | Y | M | - | - | N | S | T | N | H | A | I | H | Q | A | L | V | H | L | M | K | P | - | D | I | H | P | K | P | C |
| Pattern: | x | F | P | L | x | x | x | x | - | - | N | j | T | N | H | A | x | V | Q | T | L | V | N | x | x | x | P | n | x | x | a | P | j | P | C |
| GDF Subgroup | | | | | | | | | | | | | | | | | | | | | | | | | | | | | | | | | |
| GDF-1: | A | L | P | E | T | L | R | G | P | G | P | P | A | L | N | S | S | P | V | H | A | A | A | P | T | - | - | - | P | G | A | G | S | P | C |
| GDF-3: | P | F | S | M | T | T | Y | L | - | - | A | S | S | P | V | M | L | R | A | A | L | M | H | A | A | D | L | - | - | P | K | V | P | A | V |
| GDF-9: | P | R | A | V | R | H | R | Y | - | - | I | G | S | P | V | H | T | M | V | L | R | A | A | L | M | H | I | - | - | P | K | S | V | R | P |
| Pattern: | j | x | j | x | x | x | x | x | - | - | x | j | x | x | x | x | x | x | x | x | x | x | x | x | x | x | x | - | - | P | x | x | x | j | x |
| Inhibin Subgroup | | | | | | | | | | | | | | | | | | | | | | | | | | | | | | | | | |
| Inhibin α: | G | L | H | I | P | P | N | L | S | L | P | V | P | G | A | P | P | T | P | A | Q | P | Y | S | L | - | - | - | L | P | G | A | Q | P | C |
| Inhibin βA: | P | S | H | I | A | G | T | S | G | G | S | L | S | W | H | P | Y | R | M | R | G | H | S | P | F | A | N | - | L | G | N | L | K | S | C |
| Inhibin βB: | P | A | Y | L | A | G | V | P | G | G | S | A | S | W | H | T | M | Q | Y | R | M | R | G | L | N | - | - | - | P | F | A | N | S | P | C |
| Pattern: | x | x | e | c | j | j | x | x | j | x | x | j | x | x | H | a | x | x | x | x | x | x | x | x | x | x | - | - | x | x | j | x | x | j | C |

| 40 | 50 | 60 | 70 | | |
|---|---|---|---|---|---|
| | | HELIX | | HEEL | I K |

FIG. 5C

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| TGF-β Subgroup | | | | | | | | | | | | | | | | | | | | | | | | | | | | |
| TGF-β1: | V | - | - | P | Q | A | L | E | P | L | P | I | V | Y | Y | V | - | - | - | R | K | P | K | V | E | Q | L | S | N | M | I | V | R | S | C | K | C | S |
| TGF-β2: | V | - | - | S | Q | D | L | E | P | L | T | I | L | Y | Y | I | G | - | - | R | K | P | K | V | E | Q | L | S | N | M | V | V | K | S | C | K | C | S |
| TGF-β3: | V | - | - | P | Q | D | L | E | P | L | T | I | L | Y | Y | V | G | - | - | R | T | P | K | V | E | Q | L | S | N | M | V | V | K | S | C | K | C | S |
| TGF-β4: | V | - | - | P | Q | T | V | L | D | P | L | P | I | V | Y | Y | V | - | - | R | T | A | R | V | R | Q | L | S | N | M | I | V | R | A | C | K | C | S |
| TGF-β5: | V | - | - | P | Q | D | V | L | E | P | L | P | I | V | Y | Y | V | - | - | R | K | P | K | V | R | Q | L | S | N | M | V | V | R | S | C | K | C | S |
| Pattern: | V | - | - | P | Q | x | L | E | P | L | j | I | c | Y | Y | V | - | - | R | r | j | K | V | E | Q | L | S | N | M | a | V | n | S | C | K | C | S |
| Vg/dpp Subgroup | | | | | | | | | | | | | | | | | | | | | | | | | | | | |
| dpp: | V | - | - | P | T | Q | L | D | S | V | A | M | L | Y | L | N | D | Q | - | S | T | V | V | L | K | N | Y | Q | E | M | T | V | V | D | E | C | G | C | R |
| Vg-1: | V | - | - | P | T | K | M | S | P | I | H | S | M | L | F | Y | D | N | N | D | N | V | V | L | R | R | H | Y | E | N | M | A | V | D | E | C | G | C | R |
| Vgr-1: | A | - | - | P | T | K | L | N | A | I | S | V | L | Y | F | D | D | N | - | S | N | V | I | L | K | K | Y | R | N | M | V | V | R | A | C | G | C | H |
| 60A: | A | - | - | P | T | R | L | G | A | L | H | L | M | L | Y | H | L | D | A | E | V | P | T | L | H | N | L | S | N | M | I | V | K | S | C | G | C | H |
| BMP-2A: | V | - | - | P | T | E | L | L | D | A | H | L | Y | L | D | N | E | D | - | V | D | K | V | V | L | K | N | Y | Q | D | M | V | V | E | G | C | G | C | R |
| DORSALIN: | V | - | - | P | T | E | L | L | N | A | M | S | L | L | Y | L | A | G | - | - | K | V | P | L | K | K | Y | R | N | M | V | V | K | A | C | G | C | H |
| BMP-2B/BMP-4: | V | - | - | P | T | K | M | S | P | I | S | M | L | Y | L | D | E | D | - | E | K | V | V | L | K | N | Y | Q | D | M | V | V | E | G | C | G | C | R |
| BMP-3: | V | - | - | P | E | T | K | L | N | A | I | S | V | L | Y | F | D | D | N | S | N | V | I | L | K | K | Y | R | N | M | V | V | R | A | C | G | C | H |
| BMP-5: | A | - | - | P | T | K | L | S | P | I | S | V | L | Y | F | D | D | S | - | S | N | V | I | L | K | K | Y | R | N | M | V | V | R | A | C | G | C | H |
| BMP-6: | A | - | - | P | T | Q | L | N | A | I | S | V | L | Y | Y | D | D | S | - | S | N | V | I | L | K | K | Y | R | N | M | V | V | R | A | C | G | C | H |
| OP-1/BMP-7: | A | - | - | P | T | Q | L | N | A | I | S | V | L | Y | F | D | D | N | - | S | N | V | I | L | K | K | Y | R | N | M | V | V | R | A | C | G | C | H |
| OP-2: | A | - | - | P | T | E | L | S | A | T | S | L | L | Y | Y | D | R | N | - | S | N | V | I | L | R | R | H | E | N | M | V | V | R | A | C | G | C | H |
| OP-3: | V | - | - | P | T | p | L | r | A | a | s | c | L | Y | f | D | m | r | - | N | r | V | a | L | n | r | Y | p | l | M | x | V | p | j | C | G | C | r |
| Pattern: | x | - | - | P | T | p | L | r | A | a | s | c | L | Y | f | D | m | r | - | N | r | V | a | L | n | r | Y | p | l | M | x | V | p | j | C | G | C | r |
| GDF Subgroup | | | | | | | | | | | | | | | | | | | | | | | | | | | | |
| GDF-1: | V | - | - | P | E | R | L | S | P | I | S | V | L | F | F | D | N | S | - | D | N | V | V | L | R | H | Y | E | D | M | V | V | D | E | C | G | C | R |
| GDF-3: | V | - | - | P | T | K | L | S | P | I | S | M | L | Y | Q | D | S | D | - | K | G | V | I | L | R | R | H | E | Y | M | V | V | D | E | C | G | C | G |
| GDF-9: | V | - | - | P | G | K | Y | S | P | L | S | V | L | T | I | H | E | P | - | G | x | I | A | Y | f | n | Y | E | D | M | A | I | A | T | R | C | C | T | C |
| Pattern: | V | - | - | P | x | n | f | s | P | c | L | Y | L | x | l | x | x | r | - | x | x | I | a | l | x | f | n | Y | E | D | M | a | x | r | p | C | C | j | C | x |
| Inhibin Subgroup | | | | | | | | | | | | | | | | | | | | | | | | | | | | |
| Inhibin α: | A | A | L | P | G | T | M | R | P | L | H | V | R | T | T | S | D | G | G | Y | S | F | K | Y | E | T | V | P | N | L | L | T | Q | H | C | A | C | I |
| Inhibin βA: | V | - | - | P | T | K | L | R | P | M | S | M | L | Y | Y | D | D | G | - | Q | N | I | I | K | K | D | I | Q | N | M | I | V | E | E | C | G | C | S |
| Inhibin βB: | I | - | - | P | T | K | L | S | T | M | S | M | L | Y | F | D | D | E | - | Y | N | I | V | K | R | D | V | P | N | M | I | V | E | E | C | G | C | A |
| Pattern: | x | z | x | P | j | r | b | r | j | b | r | c | x | x | x | x | x | r | - | x | x | I | x | x | x | x | x | x | x | M | x | x | x | x | C | x | C | x |

| BETA | | BETA | | FINGER 2 | LOOP | | BETA | | RING |
|---|---|---|---|---|---|---|---|---|---|
| 80 | | | | 90 | | | 100 | | 110 KNOT2 |

FIG. 7A

Finger 1 Fragment: Large Peptide

```
TGF-ß Subgroup ---------+----------+--------------------+----------
     TGF-ß1:  Q L Y I D|F R K D L|G WK - W I H E P K|G Y H A N
     TGF-ß2:  P L Y I D|F K R D L|G W K - W I H E P K|G Y N A N
     TGF-ß3:  P L Y I D|F R Q D L|G W K - W V H E P K|G Y Y A N
     TGF-ß4:  P L Y I D|F R K D L|Q W K - W I H E P K|G Y M A N
     TGF-ß5:  P L Y I N|F R K D L|G W K - W I H E P K|G Y E A N
    Pattern:  P L Y I D|F R n D L|G W K - W I H E P K|G Y X A N
Vg/dpp Subgroup---------+----------+--------------------+----------
        dpp:  S L Y V D|F S - D V|G W D D W I V A P L|G Y D A Y
       Vg-1:  H L Y V E|F K - D V|G W Q N W V I A P Q|G Y M A N
      Vgr-1:  E L Y V S|F Q - D L|G W Q D W I I A P K|G Y A A N
        60A:  T L Y I D|F K - D L|G W H D W I I A P E|G Y G A F
     BMP-2A:  P L Y V D|F S - D V|G W N D W I V A P P|G Y H A F
    DORSALIN: S L H V N|F K - E I|G W D S W I I A P K|D Y E A F
BMP-2B/BMP-4: S L Y V D|F S - D V|G W N D W I V A P P|G Y Q A F
      BMP-3:  Y L K V D|F A - D I|G W S E W I I S P K|S F D A Y
      BMP-5:  E L Y V S|F R - D L|G W Q D W I I A P E|G Y A A F
      BMP-6:  E L Y V S|F Q - D L|G W Q D W I I A P K|G Y A A N
   OP-1/BMP-7:E L Y V S|F R - D L|G W Q D W I I A P E|G Y A A Y
       OP-2:  E L Y V S|F Q - D L|G W L D W V I A P Q|G Y S A Y
       OP-3:  E L Y V S|F R - D L|G W L D S V I A P Q|G Y S A Y
    Pattern:  r L Y V r|F r - D c|G W r D W I I A P p|G Y X A d
GDF Subgroup------------+----------+--------------------+----------
      GDF-1:  R L H V S|F R - E V|G W H R W V I A P R|G F L A N
      GDF-3:  Q L F I N|F Q - D L|G W H K W V I A P K|G F M A N
      GDF-9:  D F R L S|F S - Q L|K W D N W I V A P H|R Y N P R
    Pattern:  r f X c r|F r - r c|X W r r W a a A P r|X d X j r
Inhibin Subgroup--------+----------+--------------------+----------
   Inhibin α: A L N I S|F Q - E L|G W E R W I V Y P P|S F I F H
   Inhibin ßA:Q F F V S|F K - D I|G W N D W I I A P S|G Y H A N
   Inhibin ßB:Q F F I D|F R - L I|G W N D W I I A P T|G Y Y G N
    Pattern:  X f X a r|F p - X c|G W m r W I a X P j|j d X X r
-----------+----------+--------------------+----------
            10        |           20       |
```

FIG. 7B

Finger 1 Fragment: Medium Peptide

```
TGF-ß Subgroup ----+---------+--------------------+------
     TGF-ß1:   Y I D|F R K D L|G W K - W I H E P K|G Y H
     TGF-ß2:   Y I D|F K R D L|G W K - W I H E P K|G Y N
     TGF-ß3:   Y I D|F R Q D L|G W K - W V H E P K|G Y Y
     TGF-ß4:   Y I D|F R K D L|Q W K - W I H E P K|G Y M
     TGF-ß5:   Y I N|F R K D L|G W K - W I H E P K|G Y E
    Pattern:   Y I D|F R n D L|G W K - W I H E P K|G Y X
Vg/dpp Subgroup----+---------+--------------------+------
        dpp:   Y V D|F S - D V|G W D D W I V A P L|G Y D
       Vg-1:   Y V E|F K - D V|G W Q N W V I A P Q|G Y M
      Vgr-1:   Y V S|F Q - D L|G W Q D W I I A P K|G Y A
        60A:   Y I D|F K - D L|G W H D W I I A P E|G Y G
      BMP-2A:  Y V D|F S - D V|G W N D W I V A P P|G Y H
    DORSALIN:  H V N|F K - E I|G W D S W I I A P K|D Y E
 BMP-2B/BMP-4: Y V D|F S - D V|G W N D W I V A P P|G Y Q
      BMP-3:   K V D|F A - D I|G W S E W I I S P K|S F D
      BMP-5:   Y V S|F R - D L|G W Q D W I I A P E|G Y A
      BMP-6:   Y V S|F Q - D L|G W Q D W I I A P K|G Y A
   OP-1/BMP-7: Y V S|F R - D L|G W Q D W I I A P E|G Y A
       OP-2:   Y V S|F Q - D L|G W L D W V I A P Q|G Y S
       OP-3:   Y V S|F R - D L|G W L D S V I A P Q|G Y S
    Pattern:   Y V r|F r - D c|G W r D W I I A P p|G Y X
GDF Subgroup-------+---------+--------------------+------
      GDF-1:   H V S|F R - E V|G W H R W V I A P R|G F L
      GDF-3:   F I N|F Q - D L|G W H K W V I A P K|G F M
      GDF-9:   R L S|F S - Q L|K W D N W I V A P H|R Y N
    Pattern:   X c r|F r - r c|X W r r W a a A P r|X d X
Inhibin Subgroup---+---------+--------------------+------
   Inhibin α:  N I S|F Q - E L|G W E R W I V Y P P|S F I
   Inhibin ßA: F V S|F K - D I|G W N D W I I A P S|G Y H
   Inhibin ßB: F I D|F R - L I|G W N D W I I A P T|G Y Y
    Pattern:   X a r|F p - X c|G W m r W I a X P j|j d X
              ------+---------+--------------------+------
                   10         |          20        |
```

FIG. 7C

Finger 1 Fragment: Small Peptide

```
TGF-ß Subgroup ------+------------------
      TGF-ß1:  R K D L|G W K - W I H E P
      TGF-ß2:  K R D L|G W K - W I H E P
      TGF-ß3:  R Q D L|G W K - W V H E P
      TGF-ß4:  R K D L|Q W K - W I H E P
      TGF-ß5:  R K D L|G W K - W I H E P
     Pattern:  R n D L|G W K - W I H E P
Vg/dpp Subgroup------+------------------
         dpp:  S - D V|G W D D W I V A P
        Vg-1:  K - D V|G W Q N W V I A P
       Vgr-1:  Q - D L|G W Q D W I I A P
         60A:  K - D L|G W H D W I I A P
      BMP-2A:  S - D V|G W N D W I V A P
    DORSALIN:  K - E I|G W D S W I I A P
 BMP-2B/BMP-4: S - D V|G W N D W I V A P
       BMP-3:  A - D I|G W S E W I I S P
       BMP-5:  R - D L|G W Q D W I I A P
       BMP-6:  Q - D L|G W Q D W I I A P
    OP-1/BMP-7: R - D L|G W Q D W I I A P
        OP-2:  Q - D L|G W L D W V I A P
        OP-3:  R - D L|G W L D S V I A P
     Pattern:  r - D c|G W r D W I I A P
GDF Subgroup---------+------------------
       GDF-1:  R - E V|G W H R W V I A P
       GDF-3:  Q - D L|G W H K W V I A P
       GDF-9:  S - Q L|K W D N W I V A P
     Pattern:  r - r c|X W r r W a a A P
Inhibin Subgroup-----+------------------
    Inhibin α: Q - E L|G W E R W I V Y P
    Inhibin ßA: K - D I|G W N D W I I A P
    Inhibin ßB: R - L I|G W N D W I I A P
     Pattern:  p - X c|G W m r W I a X P
             --------+------------------
                     |         20
```

FIG. 7D
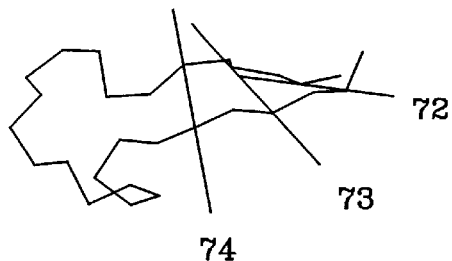 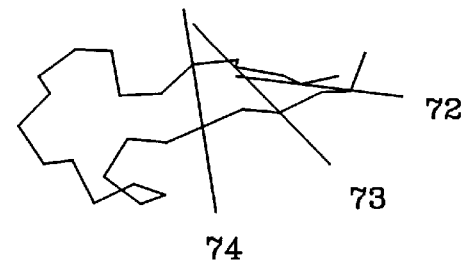
FIG. 7E
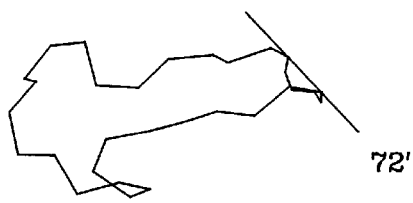 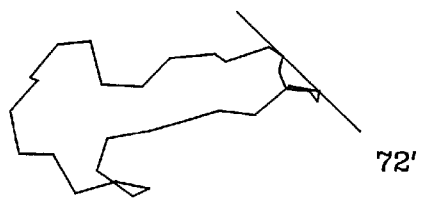
FIG. 7F
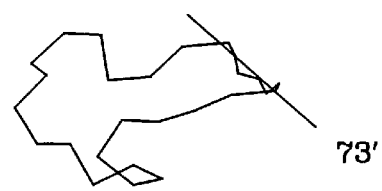 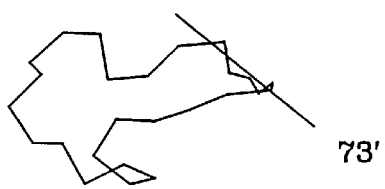
FIG. 7G
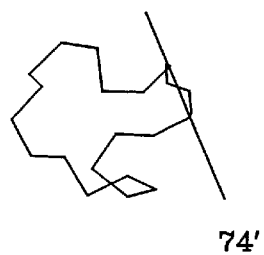 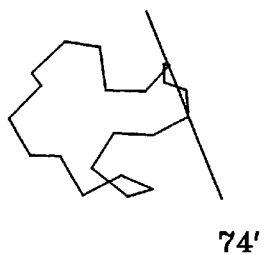

FIG. 8A

Heel Fragment: Large Peptide

```
TGF-ß Subgroup-------------------+---------------
      TGF-ß1:  K V L A L Y N Q H N|P - - G A S A A
      TGF-ß2:  R V L S L Y N T I N|P - - E A S A S
      TGF-ß3:  T V L G L Y N T L N|P - - E A S A S
      TGF-ß4:  K V L A L Y N Q H N|P - - G A S A A
      TGF-ß5:  K V L S L Y N Q N N|P - - G A S I S
     Pattern:  n V L j L Y N r X N|P - - X A S A j
Vg/dpp Subgroup------------------+---------------
         dpp:  V V Q T L V N N M N|P - - G K V P K
        Vg-1:  I L Q T L V H S I E|P - - E D I P L
       Vgr-1:  I V Q T L V H L M N|P - - E Y V P K
         60A:  I V Q T L V H L L E|P - - K K V P K
      BMP-2A:  I V Q T L V N S V N|- - - S K I P K
    DORSALIN:  I V Q T L V H L Q N|P - - K K A S K
 BMP-2B/BMP-4: I V Q T L V N S V N|- - - S S I P K
       BMP-3:  T I Q S I R A V G|V V - P G I P E
       BMP-5:  I V Q T L V H L M F|P - - D H V P K
       BMP-6:  I V Q T L V H L M N|P - - E Y V P K
    OP-1/BMP-7: I V Q T L V H F I N|P - - E T V P K
        OP-2:  I L Q S L V H L M K|P - - N A V P K
        OP-3:  T M Q A L V H L M K|P - - D I I P K
     Pattern:  I a Q T L V r X c r|z z - r X a P K
GDF Subgroup---------------------+---------------
       GDF-1:  V L R A L M H A A A|P T - P G A G S
       GDF-3:  F M Q A L M H M A D|- - - P K V P K
       GDF-9:  M V Q N I I Y E K L|D - - P S V P R
     Pattern:  f c p X c c e X X X|z z - P X X j r
Inhibin Subgroup-----------------+---------------
   Inhibin α:  P T P A Q P Y S L -|- - - L P G A Q
   Inhibin ßA: T V I N H Y R M R G|H S P F A N L K
   Inhibin ßB: A V V N Q Y R M R G|L N - P G T V N
     Pattern:  j X X X r X X X X z|z z z X j X X r
              -------------------+---------------
                              60  |              70
```

FIG. 8B

Heel Fragment: Medium Peptide

```
TGF-ß Subgroup------------+----------------
    TGF-ß1:  A L Y N Q H N|P - - G A S A A
    TGF-ß2:  S L Y N T I N|P - - E A S A S
    TGF-ß3:  G L Y N T L N|P - - E A S A S
    TGF-ß4:  A L Y N Q H N|P - - G A S A A
    TGF-ß5:  S L Y N Q N N|P - - G A S I S
   Pattern:  j L Y N r X N|P - - X A S A j
Vg/dpp Subgroup-----------+----------------
       dpp:  T L V N N M N|P - - G K V P K
      Vg-1:  T L V H S I E|P - - E D I P L
     Vgr-1:  T L V H L M N|P - - E Y V P K
       60A:  T L V H L L E|P - - K K V P K
    BMP-2A:  T L V N S V N|- - - S K I P K
  DORSALIN:  T L V H L Q N|P - - K K A S K
BMP-2B/BMP-4: T L V N S V N|- - - S S I P K
     BMP-3:  S I V R A V G|V V - P G I P E
     BMP-5:  T L V H L M F|P - - D H V P K
     BMP-6:  T L V H L M N|P - - E Y V P K
  OP-1/BMP-7: T L V H F I N|P - - E T V P K
      OP-2:  S L V H L M K|P - - N A V P K
      OP-3:  A L V H L M K|P - - D I I P K
   Pattern:  T L V r X c r|z z - r X a P K
GDF Subgroup-------------+----------------
     GDF-1:  A L M H A A A|P T - P G A G S
     GDF-3:  A L M H M A D|- - - P K V P K
     GDF-9:  N I I Y E K L|D - - P S V P R
   Pattern:  X c c e X X X|z z - P X X j r
Inhibin Subgroup----------+----------------
 Inhibin α:  A Q P Y S L -|- - - L P G A Q
 Inhibin ßA: N H Y R M R G|H S P F A N L K
 Inhibin ßB: N Q Y R M R G|L N - P G T V N
   Pattern:  X r X X X X z|z z z X j X X r
             -------------+----------------
                       60  |             70
```

FIG. 8C

Heel Fragment: Small Peptide

```
TGF-ß Subgroup-----+------------
     TGF-ß1:  Q H N|P - - G A S
     TGF-ß2:  T I N|P - - E A S
     TGF-ß3:  T L N|P - - E A S
     TGF-ß4:  Q H N|P - - G A S
     TGF-ß5:  Q N N|P - - G A S
    Pattern:  r X N|P - - X A S
Vg/dpp Subgroup---+------------
        dpp:  N M N|P - - G K V
       Vg-1:  S I E|P - - E D I
      Vgr-1:  L M N|P - - E Y V
        60A:  L L E|P - - K K V
      BMP-2A: S V N|- - - S K I
   DORSALIN:  L Q N|P - - K K A
 BMP-2B/BMP-4: S V N|- - - S S I
      BMP-3:  A V G|V V - P G I
      BMP-5:  L M F|P - - D H V
      BMP-6:  L M N|P - - E Y V
   OP-1/BMP-7: F I N|P - - E T V
       OP-2:  L M K|P - - N A V
       OP-3:  L M K|P - - D I I
    Pattern:  X c r|z z - r X a
GDF Subgroup-------+------------
      GDF-1:  A A A|P T - P G A
      GDF-3:  M A D|- - - P K V
      GDF-9:  E K L|D - - P S V
    Pattern:  X X X|z z - P X X
Inhibin Subgroup---+------------
   Inhibin α: S L -|- - - L P G
   Inhibin ßA: M R G|H S P F A N
   Inhibin ßB: M R G|L N - P G T
    Pattern:  X X z|z z z X j X
              ------+------------
                   | 65
```

FIG. 9A

Finger 2 Fragment: Large Peptide

```
TGF-ß Subgroup---------+----------------+----------
    TGF-ß1:   L P I V Y|Y V G - - R K P|K V E Q L
    TGF-ß2:   L T I L Y|Y I G - - K T P|K I E Q L
    TGF-ß3:   L T I L Y|Y V G - - R T P|K V E Q L
    TGF-ß4:   L P I I Y|Y V G - - R N V|R V E Q L
    TGF-ß5:   L P I I Y|Y V G - - R T A|K V E Q L
   Pattern:   L j I c Y|Y V G - - R r j|K V E Q L
Vg/dpp Subgroup--------+----------------+----------
        dpp:  V A M L Y|L N D Q - S T V|V L K N Y
       Vg-1:  I S M L F|Y D N N - D N V|V L R H Y
      Vgr-1:  I S V L Y|F D D N - S N V|I L K K Y
        60A:  L P V L Y|H L N D - E N V|N L K K Y
      BMP-2A: I S M L Y|L D E N - E K V|V L K N Y
    DORSALIN: I S I L Y|K D D A G V P T|L I Y N Y
 BMP-2B/BMP-4:I S M L Y|L D E Y - D K V|V L K N Y
      BMP-3:  L S I L F|F D E N - K N V|V L K V Y
      BMP-5:  I S V L Y|F D D S - S N V|I L K K Y
      BMP-6:  I S V L Y|F D D N - S N V|I L K K Y
   OP-1/BMP-7:I S V L Y|F D D S - S N V|I L K K Y
       OP-2:  T S V L Y|Y D S S - N N V|I L R K H
       OP-3:  I S L L Y|Y D R N - N N V|I L R R E
    Pattern:  a S c L Y|f D m r z r r V|a L n r Y
GDF Subgroup-----------+----------------+----------
      GDF-1:  I S V L F|F D N S - D N V|V L R H Y
      GDF-3:  I S M L Y|Q D S D - K N V|I L R H Y
      GDF-9:  L S V L T|I E P D - G S I|A Y K E Y
    Pattern:  c S c L X|X k X r - X r a|X f n r Y
Inhibin Subgroup-------+----------------+----------
   Inhibin α: L H V R T|T S D G G Y S F|K Y E T V
   Inhibin ßA:M S M L Y|Y D D G - Q N I|I K K D I
   Inhibin ßB:M S M L Y|F D D E - Y N I|V K R D V
    Pattern:  b r c X X|X r D X z X r f|X X p r a
-----------------------+----------------+----------
                       | 90             | 100
```

FIG. 9B

Finger 2 Fragment: Medium Peptide

```
TGF-ß Subgroup-----+----------------+------
       TGF-ß1:  I V Y|Y V G - - R K P|K V E
       TGF-ß2:  I L Y|Y I G - - K T P|K I E
       TGF-ß3:  I L Y|Y V G - - R T P|K V E
       TGF-ß4:  I I Y|Y V G - - R N V|R V E
       TGF-ß5:  I I Y|Y V G - - R T A|K V E
      Pattern:  I c Y|Y V G - - R r j|K V E
Vg/dpp Subgroup----+----------------+------
          dpp:  M L Y|L N D Q - S T V|V L K
         Vg-1:  M L F|Y D N N - D N V|V L R
        Vgr-1:  V L Y|F D D N - S N V|I L K
          60A:  V L Y|H L N D - E N V|N L K
       BMP-2A:  M L Y|L D E N - E K V|V L K
     DORSALIN:  I L Y|K D D A G V P T|L I Y
  BMP-2B/BMP-4: M L Y|L D E Y - D K V|V L K
        BMP-3:  I L F|F D E N - K N V|V L K
        BMP-5:  V L Y|F D D S - S N V|I L K
        BMP-6:  V L Y|F D D N - S N V|I L K
     OP-1/BMP-7:V L Y|F D D S - S N V|I L K
         OP-2:  V L Y|Y D S S - N N V|I L R
         OP-3:  L L Y|Y D R N - N N V|I L R
      Pattern:  c L Y|f D m z r r V|a L n
GDF Subgroup-------+----------------+------
        GDF-1:  V L F|F D N S - D N V|V L R
        GDF-3:  M L Y|Q D S D - K N V|I L R
        GDF-9:  V L T|I E P D - G S I|A Y K
      Pattern:  c L X|X k X r - X r a|X f n
Inhibin Subgroup---+----------------+------
     Inhibin α:  V R T|T S D G G Y S F|K Y E
     Inhibin ßA: M L Y|Y D D G - Q N I|I K K
     Inhibin ßB: M L Y|F D D E - Y N I|V K R
      Pattern:   c X X|X r D X z X r f|X X p
      ------+----------------+------
            | 90                    |
```

FIG. 9C

Finger 2 Fragment: Small Peptide

```
TGF-ß Subgroup-+---------------+--
     TGF-ß1:  Y|Y V G - - R K P|K
     TGF-ß2:  Y|Y I G - - K T P|K
     TGF-ß3:  Y|Y V G - - R T P|K
     TGF-ß4:  Y|Y V G - - R N V|R
     TGF-ß5:  Y|Y V G - - R T A|K
    Pattern:  Y|Y V G - - R r j|K
Vg/dpp Subgroup+---------------+--
        dpp:  Y|L N D Q - S T V|V
       Vg-1:  F|Y D N N - D N V|V
      Vgr-1:  Y|F D D N - S N V|I
        60A:  Y|H L N D - E N V|N
      BMP-2A: Y|L D E N - E K V|V
    DORSALIN: Y|K D D A G V P T|L
  BMP-2B/BMP-4: Y|L D E Y - D K V|V
       BMP-3: F|F D E N - K N V|V
       BMP-5: Y|F D D S - S N V|I
       BMP-6: Y|F D D N - S N V|I
    OP-1/BMP-7: Y|F D D S - S N V|I
        OP-2: Y|Y D S S - N N V|I
        OP-3: Y|Y D R N - N N V|I
     Pattern: Y|f D m z r r V|a
GDF Subgroup---+---------------+--
      GDF-1:  F|F D N S - D N V|V
      GDF-3:  Y|Q D S D - K N V|I
      GDF-9:  T|I E P D - G S I|A
    Pattern:  X|X k X r - X r a|X
Inhibin Subgroup---------------+--
   Inhibin α: T|T S D G G Y S F|K
   Inhibin ßA: Y|Y D D G - Q N I|I
   Inhibin ßB: Y|F D D E - Y N I|V
     Pattern: X|X r D X z X r f|X
              --+---------------+--
              | 90              |
```

FIG. 11A

```
OP-1/BMP-7: |C K K H E L Y V S|F R - D L|G W Q D W I I A P E|G Y A A Y Y|C E G E C - - -
   M-OP1: |C K K H E L Y V S|F R - D L|G W Q D W I I A P E|G Y A A Y Y|C - - -
          +-----------------+--------+---------------------+-----------+
          1                 10                    20                  30
          |K|  BETA          HELIX      LOOP              BETA       RING
                            FINGER_1                                KNOT_A
```

FIG. 11B

```
OP-1/BMP-7: |- - - - - - - - - -|
   M-OP1: |G S G G G S G G G S G|
          +---------------------+
                LINKER_1
```

FIG. 11C

```
OP-1/BMP-7: |A F P L N S Y - - - - M N A T|N H A I V Q T L V H F I N|P - - E T V P K P|C - -
   M-OP1: |A F P L N S Y - - - - M N A T|N H A I V Q T L V H F I N|P - - E T V P K P|- - I
          +---------------------------+-------------------------+------------------+
          40                          50                   60                    70
                                              HEEL
                                              HELIX
```

FIG. 11D

```
OP-1/BMP-7: |- - - - - -|
   M-OP1: |A  S  G  G |
          +-----------+
           |LINK_2|
```

FIG. 11E

```
OP-1/BMP-7: |C A - - - P T Q L N A I S V L Y|F D D S - S N V|I L K K Y R N M V V R A|C G C H
   M-OP1: |C A - - - P T Q L N A I S V L Y|F D D S - S N V|I L K K Y R N M V V R A|C G S H
          +-----------------------------+-----------------+-------------------------+--------
          80                           90                100                     110
                 BETA            LOOP          BETA              RING
                             FINGER_2                           KNOT2
```

SINGLE CHAIN ANALOGS OF THE TGF-β SUPERFAMILY (MORPHONS)

BACKGROUND OF THE INVENTION

This invention relates to the design and production of single-chain biosynthetic constructs herein called "morphons" which mimic the activities of one or more members of the TGF-β superfamily.

The TGF-β superfamily includes five distinct forms of TGF-β (Sporn and Roberts (1990) in *Peptide Growth Factors and Their Receptors*, Sporn and Roberts, eds., Springer-Verlag: Berlin pp. 419–472), as well as the differentiation factors vg-1 (Weeks and Melton (1987) *Cell* 51: 861–867), DPP-C polypeptide (Padgett et al. (1987) *Nature* 325: 81–84), the hormones activin and inhibin (Mason et al. (1985) *Nature* 318: 659–663; Mason et al. (1987) *Growth Factors* 1: 77–88), the Mullerian-inhibiting substance, MIS (Cate et al. (1986) *Cell* 45:685–698), osteogenic and morphogenic proteins OP-1 (PCT/US90/05903), OP-2 (PCT/US91/07654), OP-3 (PCT/WO94/10202), the BMPs, (see U.S. Pat. Nos. 4,877,864; 5,141,905; 5,013,649; 5,116,738; 5,108,922; 5,106,748; and 5,155,058), the developmentally regulated protein VGR-1 (Lyons et al. (1989) *Proc. Natl. Acad. Sci. USA* 86: 4554–4558) and the growth/differentiation factors GDF-1, GDF-3, GDF-9 and dorsalin-1 (McPherron et al. (1993) *J. Biol. Chem.* 268: 3444–4449; Basler et al. (1993) *Cell* 73: 687–702).

The proteins of the TGF-β superfamily are disulfide-linked homo- or heterodimers that are expressed as large precursor polypeptide chains containing a hydrophobic signal sequence, a long and relatively poorly conserved N-terminal pro region of several hundred amino acids, a cleavage site, and a mature domain comprising an N-terminal region which varies among the family members and a more highly conserved C-terminal region. This C-terminal region, present in the processed mature proteins of all known family members, contains approximately 100 amino acids with a characteristic cysteine motif having a conserved six or seven cysteine skeleton. Although the position of the cleavage site between the mature and pro regions varies among the family members, the cysteine pattern of the C-terminus of all of the proteins is in the identical format, ending in the sequence Cys-X-Cys-X, Ser. ID No: 44 (Sporn and Roberts (1990), supra).

Recombinant TGF-β1 has been cloned (Derynck et al. (1985) *Nature* 316: 701–705), and expressed in Chinese hamster ovary cells (Gentry et al. (1987) *Mol. Cell. Biol.* 7: 3418–3427). Additionally, recombinant human TGF-β2 (deMartin et al. (1987) *EMBO J.* 6: 3673), as well as human and porcine TGF-β3 (Derynck et al. (1988) *EMBO J.* 7: 3737–3743; Dijke et al. (1988) *Proc. Natl. Acad. Sci. USA* 85: 4715), have been cloned. Expression levels of the mature TGF-β1 protein in COS cells have been increased by substituting cysteine residues located in the pro region of the TGF-β1 precursor with serine residues (Brunner et al. (1989) *J. Biol. Chem.* 264: 13660–13664).

A unifying feature of the biology of the proteins of the TGF-β superfamily is their ability to regulate developmental processes. These structurally related proteins have been identified as being involved in a variety of developmental events. For example, TGF-β and the polypeptides of the inhibin/activin group appear to play a role in the regulation of cell growth and differentiation. MIS causes regression of the Mullerian duct in development of the mammalian male embryo, and dpp, the gene product of the Drosophila decapentaplegic complex, is required for appropriate dorsal-ventral specification. Similarly, Vg-1 is involved in mesoderm induction in Xenopus, and Vgr-1 has been identified in a variety of developing murine tissues. Regarding bone formation, many of the proteins in the TGF-β supergene family, namely OP-1 and a subset of the BMPs apparently play the major role. OP-1 (BMP-7) and other osteogenic proteins have been produced using recombinant techniques (U.S. Pat. No. 5,011,691 and PCT Application No. US 90/05903) and shown to be able to induce formation of true endochondral bone in vivo. BMP-2 has been recombinantly produced in monkey COS-1 cells and Chinese hamster ovary cells (Wang et al. (1990) *Proc. Natl. Acad. Sci. USA* 87: 2220–2224).

Recently the family of proteins taught as having osteogenic activity as judged by the Sampath and Reddi bone formation assay have been shown to be morphogenic, i.e., capable of inducing the developmental cascade of tissue morphogenesis in a mature mammal (See PCT Application No. US 92/01968). In particular, these proteins are capable of inducing the proliferation of uncommitted progenitor cells, and inducing the differentiation of these stimulated progenitor cells in a tissue-specific manner under appropriate environmental conditions. In addition, the morphogens are capable of supporting the growth and maintenance of these differentiated cells. These morphogenic activities allow the proteins to initiate and maintain the developmental cascade of tissue morphogenesis in an appropriate, morphogenically permissive environment, stimulating stem cells to proliferate and differentiate in a tissue-specific manner, and inducing the progression of events that culminate in new tissue formation. These morphogenic activities also allow the proteins to induce the "redifferentiation" of cells previously stimulated to stray from their differentiation path. Under appropriate environmental conditions it is anticipated that these morphogens also may stimulate the "redifferentiation" of committed cells.

The tertiary and quaternary structure of both TGF-β2 and OP-1 have been determined. Although TGF-β2 and OP-1 exhibit only about 35% amino acid identity in their respective amino acid sequences the tertiary and quaternary structures of both molecules are strikingly similar. Both TGF-β2 and OP-1 are dimeric in nature and have a unique folding pattern involving six of the seven C-terminal cysteine residues, as illustrated in FIG. 1A. FIG. 1A shows that in each subunit four cysteines bond to generate an eight residue ring, and two additional two cysteine residues form a disulfide bond that passes through the ring to form a knot-like structure. With a numbering scheme beginning with the most N-terminal cysteine of the 7 conserved cysteine residues assigned number 1, the 2nd and 6th cysteine residues bond to close one side of the eight residue ring while the 3rd and 7th cysteine residues close the other side. The 1st and 5th conserved cysteine residues bond through the center of the ring to form the core of the knot. The 4th cysteine forms an interchain disulfide bond with the corresponding residue in the other subunit.

Figure 1B:
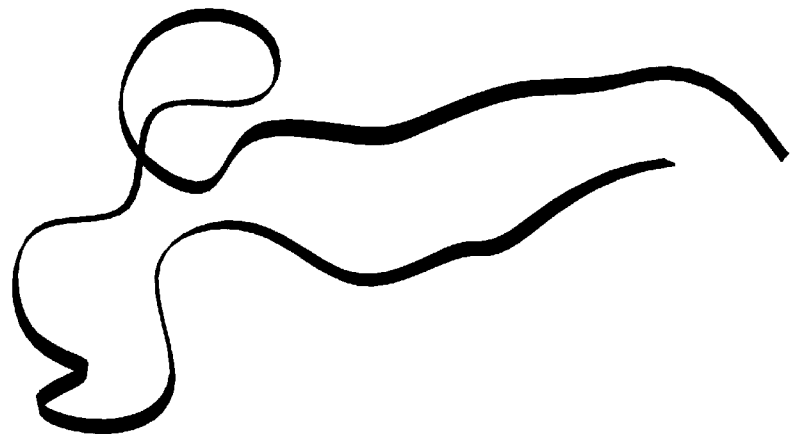

The TGF-β2 and OP-1 monomer subunits comprise three major structural elements and an N-terminal region. The structural elements are made up of regions of contiguous polypeptide chain that possess over 50% secondary structure of the following types: (1) loop, (2) helix and (3) β-sheet. Furthermore, in these regions the N-terminal and C-terminal strands are not more than 7 A apart. The residues between the 1st and 2nd conserved cysteines (FIG. 1A) form a structural region characterized by an anti-parallel β-sheet finger, referred to herein as the finger 1 region (F1). A ribbon trace of the finger 1 peptide backbone is shown in FIG. 1B.

Figure 1C:
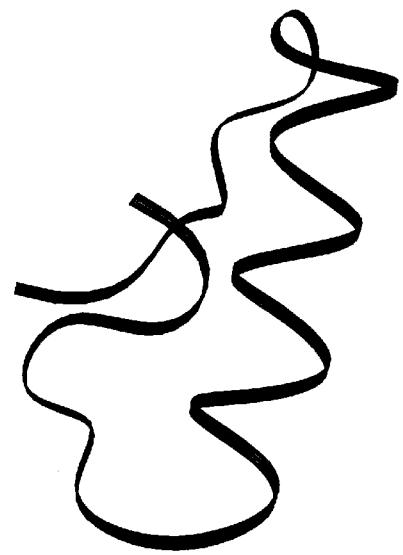
Figure 1D:
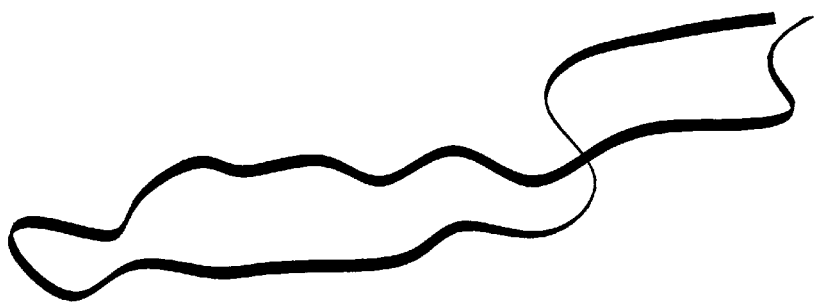

Similarly the residues between the 5th and 6th conserved cysteines in FIG. 1A also form an antiparallel β-sheet finger, referred to herein as the finger 2 region (F2). A ribbon trace of the finger 2 peptide backbone is shown in FIG. 1D. A β-sheet finger is a single amino acid chain, comprising a β-strand that folds back on itself by means of a β-turn or some larger loop so that the entering and exiting strands form one or more anti-parallel β-sheet structures. The third major structural region, involving the residues between the 3rd and 4th conserved cysteines in FIG. 1A, is characterized by a three turn α-helix referred to herein as the heel region (H). A ribbon trace of the heel peptide backbone is shown in FIG. 1C.

The organization of the monomer structure is similar to that of a left hand where the knot region is located at the position equivalent to the palm, finger 1 is equivalent to the index and middle fingers, the α-helix is equivalent to the heel of the hand, and finger 2 is equivalent to the ring and small fingers. The N-terminal region (not well defined in the published structures) is predicted to be located at a position roughly equivalent to the thumb.

Figure 2A:
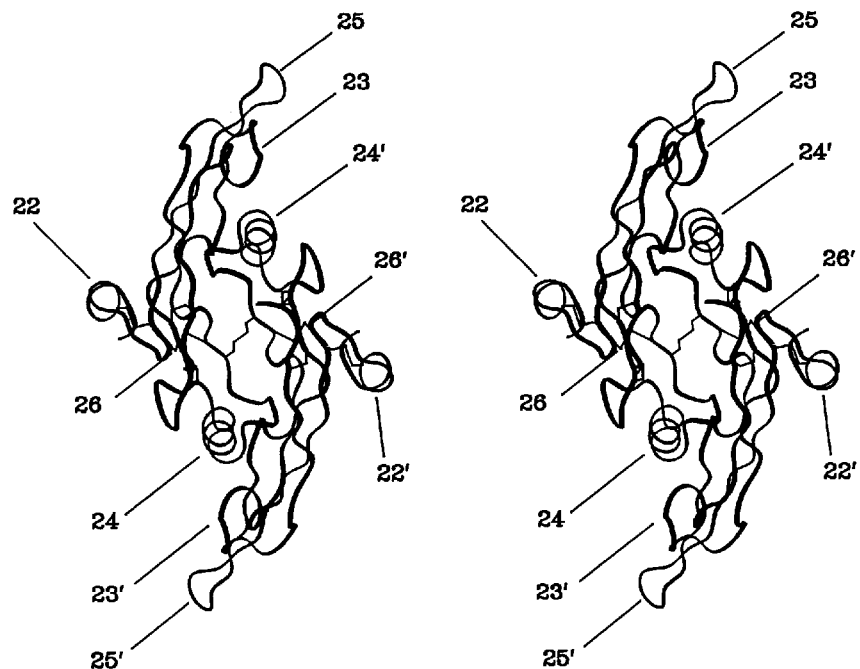
Figure 2B:
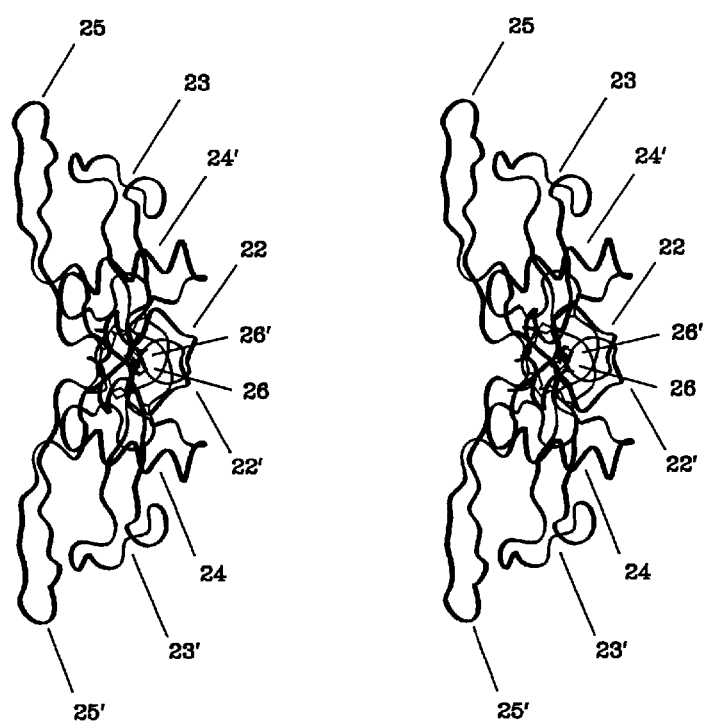

In the dimeric forms of both TGF-β2 and OP-1, the subunits are oriented such that the heel region of one subunit contacts the finger regions of the other subunit with the knot regions of the connected subunits forming the core of the molecule. The 4th cysteine forms a disulfide bridge with its counterpart on the second chain thereby equivalently linking the chains at the center of the palms. The dimer thus formed is an ellipsoidal (cigar shaped) molecule when viewed from the top looking down the two-fold axis of symmetry between the subunits (FIG. 2A). Viewed from the side, the molecule resembles a bent "cigar" since the two subunits are oriented at a slight angle relative to each other (FIG. 2B).

U.S. Pat. Nos.: 5,132,405; 5,091,513; and 5,258,498 and PCT Application No. PCT/US88/01737 disclose how to make single-chain binding proteins which mimic the structure of an immunoglobulin Fv region by linking the C- and N-termini of light- and heavy chain variable region domains, and how to make multifunctional proteins by linking together separate protein domains which function either independently or in concert. U.S. Pat. Nos.: 4,704,692; 4,881,175; 4,939,666; 4,946,778; and 5,260,203 disclose computer-based techniques for selecting a peptide linker sequences for connecting separate protein chains to produce a single-chain protein.

SUMMARY OF THE INVENTION

The invention provides a family of single-chain constructs of the TGF-β superfamily (hereinafter called "morphons") which mimic the physiological effects of one or more members of the superfamily. Specifically, the morphon constructs of the invention bind preferentially to a natural cell surface receptor that typically interacts with a TGF-β superfamily member, and the morphon, upon binding with the receptor initates a cascade of events that would occur when the TGF-β superfamily member binds to the receptor.

The morphon constructs differ from the natural TGF-β superfamily members in that they are single-chain proteins which preferably are expressed from a single DNA in a host cell. The natural members of the TGF-β superfamily are dimeric structures wherein the monomer subunits are held together by non-covalent interactions or by one or more disulfide bonds. The TGF-β superfamily members are inactive as monomers. In contrast, the morphon constructs comprise a functional monomer subunit and, therefore, are believed to be more stable than the natural dimers, particularly under reducing conditions. In addition, the morphon constructs may have a molecular weight significantly lower than the natural dimers and thus are likely to diffuse faster and be cleared by the body faster than natural superfamily members.

The morphon constructs preferably are manufactured in accordance with the principles disclosed herein by assembly of nucleotides and/or joining DNA restriction fragments to produce synthetic DNAs. The DNAs are transfected into an appropriate protein expression vehicle, the encoded protein expressed, folded if necessary, and purified. Particular constructs can be tested for agonist activity in vitro. The tertiary structure of the candidate morphon constructs may be iteratively refined and binding modulated by site-directed or nucleotide sequence directed mutagenesis aided by the principles disclosed herein, computer-based protein structure modeling, and recently developed rational drug design techniques to improve or modulate specific properties of a molecule of interest. Known phage display or other nucleotide expression systems may be exploited to produce simultaneously a large number of candidate constructs. The pool of candidate constructs subsequently may be screened for binding specificity using, for example, a chromatography column comprising surface immobilized receptors, salt gradient elution to select for, and to concentrate high binding candidates, and in vitro assays to determine whether or not particular isolated candidates agonize the activity of the template superfamily member. Identification of a useful construct is followed by production of cell lines expressing commercially useful quantities of the construct for laboratory use and ultimately for producing therapeutically useful drugs. It is contemplated also that preferred single-chain constructs, once identified and characterized by the recombinant DNA methodologies described above, may be produced by standard peptide synthesis methodologies.

It has now been discovered how to design, make, test and use single-chain amino acid constructs comprising an amino acid sequence which, when properly folded, assume a tertiary structure defining a finger 1 region, a finger 2 region, and a heel region which together are complementary to the ligand binding interactive surface of a TGF-β superfamily member receptor. The constructs, upon binding with the receptor agonize the activity of a TGF-β superfamily member. In one important subset of embodiments, the constructs agonize initiation of cellular differentiation and tissue morphogenesis, e.g., initiate cell transformation leading to new tissue formation, such as, bone formation. The constructs comprise an amino acid sequence sufficiently duplicative of the amino acid sequence of a TGF-β superfamily member such that it preferentially binds the cognate receptor for that member.

All of the morphon constructs of the invention comprise regions of amino acid sequences defining the three regions required for utility, namely, finger 1, finger 2, and heel regions, and additional linker sequences which join these regions, maintain them in their proper conformation individually, and maintain their relative positions and orientations in space. Sequences for the finger and heel regions may be copied from the respective finger and heel region sequences of any known TGF-β superfamily member identified herein. Alternatively, the finger and heel regions may be selected from the amino acid sequence of a new member of this superfamily discovered hereafter using the principles disclosed hereinbelow.

The finger, heel, and linker sequences also may be altered by amino acid substitution, for example by exploiting substitute amino acid residues selected in accordance with the principles disclosed in Smith et al. (1990) *Proc. Natl. Acad. Sci. USA* 87: 118–122, the disclosure of which is incorporated herein by reference. Smith et al. disclose an amino acid class hierarchy, similar to the amino acid hierarchy table set forth in FIG. 10, which may be used to rationally substitute one amino acid for another while minimizing gross conformational distortions of the type which otherwise may inactivate the protein. In any event, it is contemplated that many synthetic finger 1, finger 2, and heel region sequences, having only 70% homology with natural regions, preferably 80%, and most preferably at least 90%, may be used to produce active morphon constructs. It is contemplated also, as disclosed herein, that the size of the constructs may be reduced significantly by truncating the natural finger and heel regions of the template TGF-β superfamily member, while compensating for dimensional changes using linkers as disclosed below.

The linker sequences, as described herein, join and maintain the spatial relationship of the finger and heel regions within a monomeric subunit. The linker sequences typically comprising about 3–13 amino acids serve to maintain, for example, the cysteine structural motif, namely, the cysteine pattern and knot structure (cysteines 1, 2, 3, 5, 6, and 7, and their respective spatial and bonding relationship) which characterize, and are believed to be essential for maintaining the tertiary structure of the members of the superfamily. Principles and methods for selecting appropriate polypeptide linker sequences are disclosed hereinbelow.

More specifically, the invention provides a functional morphon construct that is constituted by a finger 1, a finger 2, and a heel region, joined together by peptide linkers having, e.g., 3–13 amino acids, and optionally including an N-terminal sequence upstream of the first cysteine beginning the sequence of the finger 1 region. In the single-chain morphon constructs of the invention, the finger 1, finger 2 and heel regions together define a structure complementary to the ligand binding surface of a TGF-β superfamily member receptor structure and are sufficiently duplicative of a sequence of a member of the TGF-β superfamily such that the construct preferentially binds the receptor. Where the finger 1 region is designated F1, the finger 2 designated F2, and the heel designated H, the constructs of this type can take the form of one of the constructs set forth below, and include:

F1-linker-F2-linker-H
F1-linker-H-linker-F2
F2-linker-F1-linker-H
F2-linker-H-linker-F1
H-linker-F1-linker-F2, and
H-linker-F2-linker-F1.

Generic and specific sequences of amino acids which constitute the finger 1, finger 2, heel regions, and N-terminal sequences are disclosed hereinbelow.

The invention further comprises DNAs encoding the morphon constructs of the invention, cell lines transformed with the DNAs, and methods of making the morphons by culturing transformed cells to produce them followed by purification.

The invention may be understood further, and various of its objects and features better appreciated by referring to the drawings, description, sequence listing, and claims which follow.

BRIEF DESCRIPTION OF THE DRAWING

FIG. 1A is a simplified line drawing useful in describing the structure of a monomeric subunit of a TGF-β superfamily member. See the Background of the Invention, supra, for explanation.

FIGS. 1B, 1C, and 1D are monovision ribbon tracings of the respective peptide backbones of typical secondary structures of the finger 1, heel, and finger 2 regions.

FIGS. 2A and 2B are stereo peptide backbone ribbon trace drawings illustrating the generic three-dimensional shape of TGF-β superfamily member protein dimer: A) from the "top" (down the two-fold axis of symmetry between the subunits) with the axes of the helical heel regions generally normal to the paper and the axes of each of the finger 1 and finger 2 regions generally vertical, and B) from the "side" with the two-fold axis between the subunits in the plane of the paper, with the axes of the heels generally horizontal, and the axes of the fingers generally vertical. The reader is encouraged to view the stereo alpha carbon trace drawings in wall eyed stereo to understand better the spatial relationships in the morphon design.

FIGS. 3A and 3B are respective schematic representations of a natural member of the TGF-β superfamily and a morphon construct of the invention.

FIGS. 4A and 4B are stereo peptide backbone ribbon trace drawings of a half molecule or morphon construct viewed from the top (same convention as used in FIG. 2) and side, respectively.

FIGS. 5A, 5B, and 5C are single letter code listings of amino acid sequences, arranged to indicate alignments and homologies of the finger 1, heel, and finger 2 regions, respectively, of the currently known members of the TGF-β superfamily. Shown are the respective amino acids comprising each region of human TGF-β1 through TGF-β5 (the TGF-β subgroup), the Vg/dpp subgroup consisting of dpp, Vg-1, Vgr-1, 60A (see copending U.S. Ser. No. 08/271,556), BMP-2A (also known in the literature as BMP-2), dorsalin, BMP-2B (also known in the literature as BMP-4), BMP-3, BMP-5, BMP-6, OP-1 (also known in the literature as BMP-7), OP-2 (see PCT/US91/07635 and U.S. Pat. No. 5,266,683) and OP-3 (U.S. Ser. No. 07/971,091), the GDF subgroup consisting of GDF-1, GDF-3, and GDF-9, the Inhibin subgroup consisting of Inhibin α, Inhibin βA, and Inhibin βB. The dashes (–) indicate a peptide bond between adjacent amino acids. A consensus sequence pattern for each subgroup is shown at the bottom of each subgroup.

Each of the recited sequences are identified by Sequence Listing identifiers as follows: TGF-β1, SEQ ID NO: 1; TGF-β2, SEQ ID NO: 2; TGF-β3, SEQ ID NO: 3; TGF-β4, SEQ ID NO: 4; TGF-β5, SEQ ID NO: 5; TGF-β Pattern, SEQ ID NO: 25; dpp, SEQ ID NO: 6; Vg-1, SEQ ID NO: 7; Vgr-1, SEQ ID NO: 8; 60A, SEQ ID NO: 9; BMP-2A, SEQ ID NO: 10; Dorsalin, SEQ ID NO: 15; BMP-2B/BMP-4, SEQ ID NO: 12; BMP-3, SEQ ID NO: 11; BMP-5, SEQ ID NO: 13; BMP-6, SEQ ID NO: 14; OP-1/BMP-7, SEQ ID NO: 16; OP-2, SEQ ID NO: 17; OP-3, SEQ ID NO: 18; Vg/dpp Pattern, SEQ ID NO: 26; GDF-1, SEQ ID NO: 19; GDF-3, SEQ ID NO: 20; GDF-9, SEQ ID NO: 21; GDF Pattern, SEQ ID NO: 27; Inhibin α, SEQ ID NO: 22; Inhibin βA, SEQ ID NO: 23; Inhibin βB, SEQ ID NO: 24, and Inhibin Pattern, SEQ ID NO: 28.

FIG. 6 is a single letter code listing of amino acid sequences, identified in capital letter in standard single letter amino acid code, and in lower case letters to identify groups of amino acids useful in that location, wherein the lower case letters stand for the amino acids indicated in accordance with the pattern definition key table set forth in FIG. 10. FIG. 6 identifies preferred pattern sequences for constituting the finger 1, heel, and finger 2 regions of biosynthetic constructs of the invention. The dashes (–) indicate a peptide bond between adjacent amino acids.

FIGS. 7A, 7B, and 7C are single letter code listings of large, medium, and small peptides, respectively, comprising 24 (large), 20 (medium) or 12 (small) amino acids embodying truncated versions of finger 1 regions useful in constructing morphon constructs of the invention. Also disclosed in FIGS. 7A, 7B, and 7C are sequence patterns identifying specific amino acid residues (upper case letters in accordance with the standard single letter amino acid code) or groups of amino acid residues (lower case letters in accordance with the principles described in FIG. 10) that are useful at particular locations in the finger 1 region or the truncated versions thereof.

Each of the recited sequences are identified by Sequence Listing identifiers as follows: TGF-β Pattern, SEQ ID NO: 25; Vg/dpp Pattern, SEQ ID NO: 26; GDF Pattern, SEQ ID NO: 27; and Inhibin Pattern, SEQ ID NO: 28.

FIGS. 7D, 7E, 7F, and 7G are stereo peptide backbone ribbon trace drawings defining the whole TGF-β2 finger 1 region, and the large, medium, and small finger 1 peptide sequences, respectively. The stereo ribbon trace drawings of FIGS. 7E, 7F, and 7G correspond to the TGF-62 2 peptide sequences set forth in FIGS. 7A, 7B, and 7C, respectively.

FIGS. 8A, 8B, and 8C are single letter code listings of large, medium, and small peptides comprising amino acid sequences embodying truncated versions of heel regions useful in constructing morphon constructs of the invention. The "large" sequence comprises as few as 14 amino acids (e.g., for Inhibin α) and up to 18 (e.g., for Inhibin βA TGF-β2 and OP-1 exhibit only about 36% amino acid sequence identity, when taken together with the fact that TGF-β2 and OP-1 exhibit different physiological activities it is striking that both the tertiary and quaternary structures of these molecules are substantially the same Each of the subunits in either TGF β2 or OP-1 have a characteristic folding pattern, illustrated schematically in FIG. 1A, that involves six of the seven C-terminal cysteine residues. Briefly, four of the cysteine residues in each subunit form two disulfide bonds which together create an eight residue ring, while two additional cysteine residues form a disulfide bond that passes through the ring to form a knot-like structure. With a numbering scheme beginning with the most N-terminal cysteine of the 7 conserved cysteine residues assigned number 1, the 2nd and 6th cysteine residues are disulfide bonded to close one side of the eight residue ring while the 3rd and 7th cysteine residues are disulfide bonded to close the other side of the ring. The 1st and 5th conserved cysteine residues are disulfide bonded through the center of the ring to form the core of the knot. Amino acid sequence alignment patterns suggest this structural motif is conserved between members of the TGF-β superfamily. The 4th cysteine is semiconserved conserved and when present typically forms an interchain disulfide bond (ICDB) with the corresponding cysteine residue in the other subunit.

The structure of each subunit in TGF-β2 and OP-1 comprise three major tertiary structural elements and an N-terminal region. The structural elements are made up of regions of contiguous polypeptide chain that possess over 50% secondary structure of the following types: (1) loop, (2) helix and (3) β-sheet. Another defining criterion for each structural region is that the entering (N-terminal) and exiting (C-terminal) peptide strands are fairly close together, being about 7 A apart.

The amino acid sequence between the 1st and 2nd conserved cysteines, as shown in FIG. 1A, form a structural region characterized by an anti-parallel β-sheet finger referred to herein as the finger 1 region. Similarly the residues between the 5th and 6th conserved cysteines, as shown in FIG. 1A, also form an anti-parallel β-sheet finger, referred to herein as the finger 2 region. A β-sheet finger is a single amino acid chain, comprising a β-strand that folds back on itself by means of a β-turn or some larger loop so that the polypeptide chain entering and exiting the region form one or more anti-parallel β-sheet structures. The third major structural region, involving the residues between the 3rd and 5th conserved cysteines, as shown in FIG. 1A, is characterized by a three turn a α-helix, referred to herein as the heel region. The organization of the monomer structure is similar to that of a left hand where the knot region is located at the position equivalent to the palm, the finger 1 region is equivalent to the index and middle fingers, the α-helix, or heel region, is equivalent to the heel of the hand, and the finger 2 region is equivalent to the ring and small fingers. The N-terminal region whose sequence is not conserved across the TGF-β superfamily is predicted to be located at a position roughly equivalent to the thumb.

Monovision ribbon tracings of the alpha carbon backbones of each of the three major independent structural elements of the TGF-β2 monomer are illustrated in FIGS. 1B–1D. Specifically, an exemplary finger 1 region comprising the first anti-parallel β-sheet segment is shown in FIG. 1B, an exemplary heel region comprising the three turn α-helical segment is shown in FIG. 1C, and an exemplary finger 2 region comprising second and third anti-parallel β-sheet segments is shown in FIG. 1D.

FIG. 2 shows stereo ribbon trace drawings of the peptide backbone of the conformationally active TGF-β2 dimer complex. The two monomer subunits in the dimer complex are oriented symmetrically such that the heel region of one subunit contacts the finger regions of the other subunit with the knot regions of the connected subunits forming the core of the molecule. The 4th cysteine forms an interchain disulfide bond with its counterpart on the second chain thereby equivalently linking the chains at the center of the palms. The dimer thus formed is an ellipsoidal (cigar shaped) molecule when viewed from the top looking down the two-fold axis of symmetry between the subunits (FIG. 2A). Viewed from the side, the molecule resembles a bent "cigar" since the two subunits are oriented at a slight angle relative to each other (FIG. 2B).

As shown in FIG. 2, each of the structural elements which together define the native monomer subunits of the dimer are labeled 22, 22', 23, 23', 24, 24', 25, 25', 26, and 26', wherein, elements 22, 23, 24, 25, and 26 are defined by one subunit and elements 22', 23', 24', 25', and 26' belong to the other subunit. Specifically, 22 and 22' denote N-terminal domains; 23 and 23' denote the finger 1 regions; 24 and 24' denote heel regions; 25 and 25' denote the finger 2 regions; and 26 and 26' denote disulfide bonds which connect the 1st and 5th conserved cysteines of each subunit to form the knot-like structure. From FIG. 2, it can be seen that the heel region from one subunit, e.g., 24, and the finger 1 and finger 2 regions, e.g., 23' and 25', respectively from the other subunit, interact with one another. These three elements co-operate with one other to define a structure interactive with, and complimentary to the ligand binding interactive surface of the cognate receptor.

Single-Chain Biosynthetic Constructs of the Invention (Morphons).

As mentioned above, the morphon constructs differ from the natural TGF-β superfamily members in that they are single-chain proteins expressed preferably from a single DNA in a host cell. Natural TGF-β superfamily members are dimeric molecules wherein the subunits are held together by non-polar interactions and/or one or more inter-chain disulfide bonds. The TGF-β superfamily members are only active in their dimeric conformation. In contrast, the morphons are active as a monomer subunit and comprise in the single subunit, two finger regions which normally would belong to one subunit of the natural dimer and a heel region which normally would belong to the other subunit of the natural dimer. It is, therefore, contemplated that the biosynthetic constructs of the invention may be more stable, particularly under reducing conditions, than the natural morphogen dimers. In addition, it is contemplated that the biosynthetic morphon constructs may have a molecular weight substantially lower than natural biologically active TGF-β superfamily members, and therefore may diffuse faster, and be cleared by the body faster than the natural superfamily members.

Figure 3B:
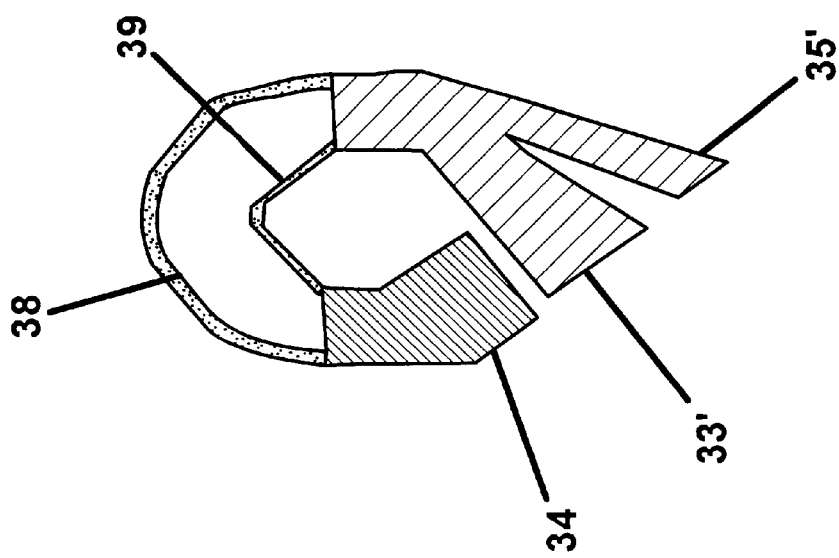
Figure 3A:
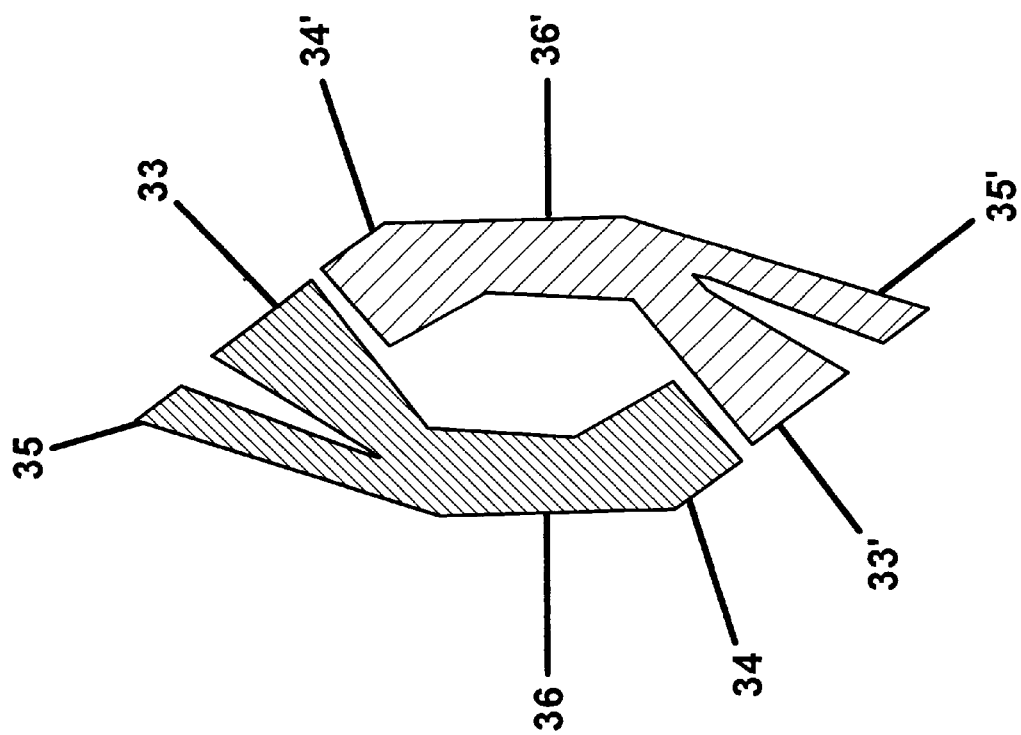

The differences between functionally active TGF-β superfamily members and morphons are shown schematically in FIG. 3. For example, FIG. 3A shows a dimeric TGF-β superfamily member wherein one subunit defining a finger 1 (33), finger 2 (35), heel region (34), and a knot region (36) and the other subunit defining a finger 1 (33'), finger 2 (35'), a heel region (34') and a knot region (36') are represented by the differently hatched motifs. FIG. 3B shows a morphon construct defining a finger 1 (33') a finger 2 (35') and a heel region (34); however, the finger 1 and finger 2 regions typically are derived from one subunit of a dimeric TGF-β superfamily member and the heel region typically is derived from the other subunit of the TGF-β superfamily member. In the morphon construct, the finger and heel regions are connected by two polypeptide linkers (38 and 39) as depicted by the stippled regions.

The morphon constructs of the invention comprise a finger 1 region, a heel region and a finger 2 region, joined together by polypeptide linkers comprising, for example, about 3–13 amino acids, and optionally including an N-terminal sequence upstream of the first cysteine beginning the sequence of the first finger region. Where the finger 1 region is designated F1, the finger 2 region is designated F2, and the heel region is designated H, the constructs of this type can take several forms and include, for example:

F1-linker-F2-linker-H
F1-linker-H-linker-F2
F2-linker-F1-linker-H
F2-linker-H-linker-F1
H-linker-F1-linker-F2, and
H-linker-F2-linker-F1.

Figure 4A:
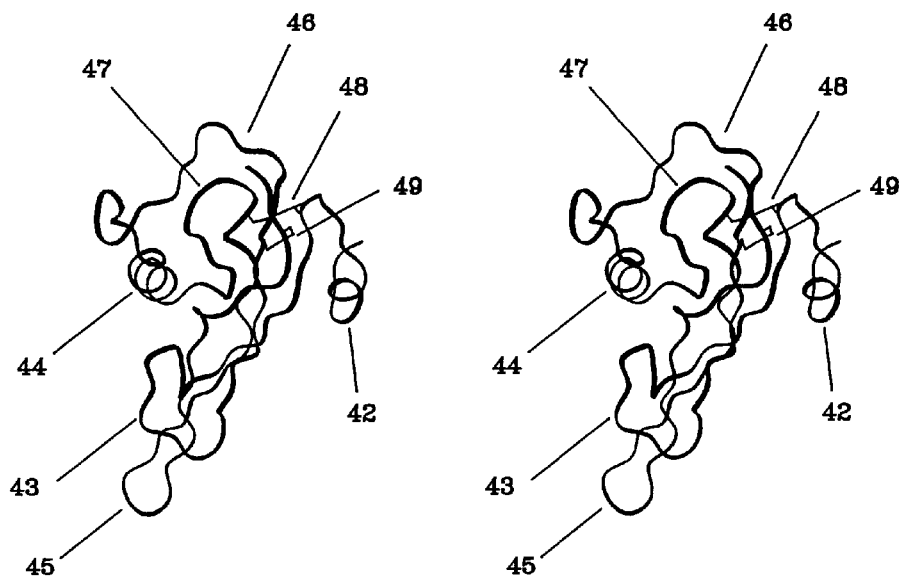
Figure 4B:
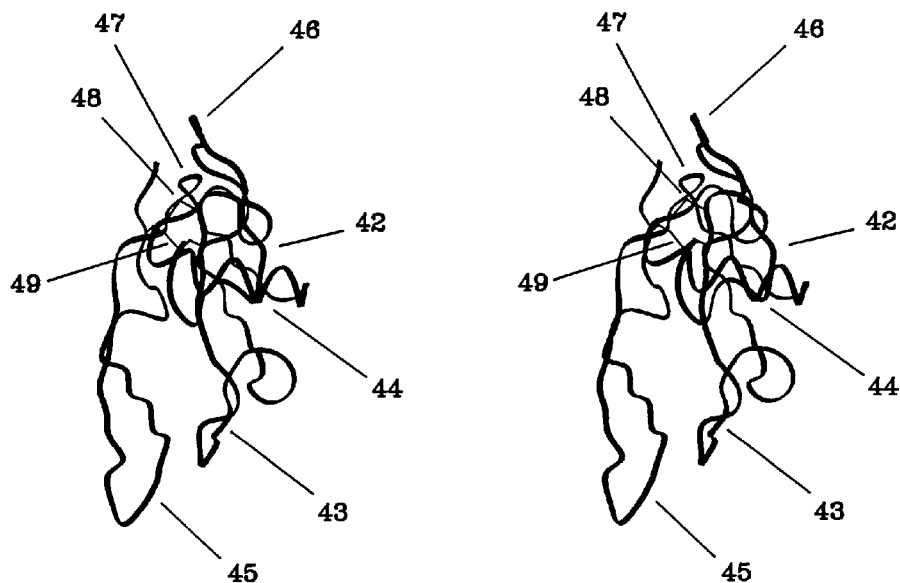

FIG. 4 shows stereo ribbon trace drawings of the peptide backbone of an exemplary morphon construct, wherein FIGS. 4A and 4B show top and side views of the morphon, respectively, using the same convention as described in FIG. 2. Each of the structural elements of the exemplary morphon are labeled 42, 43, 44, 45, 46, 47, 48, and 49. Label 42 denotes the N-terminal domain, label 43 denotes the finger 1 region, label 44 denotes the heel region, label 45 denotes the finger 2 region, labels 46 and 47 denote polypeptide linkers which link the finger and heel regions, and labeled 48 and 49 denote disulfide bonds. In this figure, the disulfide bond 48 links an N-terminal part of the finger 1 region to an N-terminal part of the finger 2 region and the disulfide bond 49 links a C-terminal part of the finger 1 region to a C-terminal part of the finger 2 region.

Without wishing to be bound by theory, it is contemplated that hydrophobic interactions between the finger and heel elements may stabilize the tertiary structure of each morphon. It is contemplated also that engineered disulfide bonds may likewise stabilize the folded structure of the morphon construct. It is understood that the skilled artisan need not determine a priori the precise locations of the disulfide bonds when designing the constructs because morphogen constructs having optimal stability and biological activity may be isolated using conventional screening methodologies, such as those discussed hereinbelow.

It is contemplated that the amino acid sequences defining the finger and heel regions may be copied from the respective finger and heel region sequences of any known member of the TGF-β superfamily. Furthermore, it is contemplated also that the size of the morphon constructs of the invention may be reduced significantly by truncating the natural finger and heel regions of the template TGF-β superfamily member, while compensating for dimensional changes by using polypeptide linker sequences. Truncated forms of the morphon constructs are referred to herein as "mini morphons".

I. Selection of Finger and Heel Regions

As mentioned above, amino acid sequences defining finger and heel regions may be copied either from the respective finger and heel region sequences of any known TGF-β superfamily member, identified herein, or from amino acid sequences of a new superfamily member discovered hereafter.

FIG. 5 summarizes the amino acid sequences of currently identified TGF-β superfamily members aligned into finger 1 (FIG. 5A), heel (FIG. 5B) and finger 2 (FIG. 5C) regions.

The sequences were aligned by a computer algorithm which in order to optimally align the sequences inserted gaps into regions of amino acid sequence known to define loop structures rather than regions of amino acid sequence known to have conserved amino acid sequence or secondary structure. For example, if possible, no gaps were introduced into amino acid sequences of finger 1 and finger 2 regions defined by β sheet or heel regions defined by α helix. The dashes (–) indicate a peptide bond between adjacent amino acids. A consensus sequence pattern for each subgroup is shown at the bottom of each subgroup.

After the amino acid sequences of each of the TGF-β superfamily members were aligned, the aligned sequences were used to produce amino acid sequence alignment patterns which identify amino acid residues that may be substituted by another amino acid or group of amino acids without altering the overall tertiary structure of the morphon construct. The amino acids or groups of amino acids that may be useful at a particular position in the finger and heel regions were identified by a computer algorithm implementing the amino acid hierarchy pattern structure shown in FIG. 10.

Briefly, the algorithm performs four levels of analysis. In level I, the algorithm determines whether a particular amino acid residue occurs with a frequency greater than 75% at a specific position within the amino acid sequence. For example, if a glycine residue occurs 8 out of 10 times at a particular position in an amino acid sequence, then a glycine is designated at that position. If the position to be tested consists of all gaps then a gap character (–) is assigned to the position, otherwise, if at least one gap exists then a "z" (standing for any residue or a gap) is assigned to the position. If, no amino acid occurs in 75% of the candidate sequences at a particular position the algorithm implements the Level II analysis.

Level II defines pattern sets a, b, d, l, k, o, n, i, and h, wherein l, k, and o share a common amino acid residue. The algorithm then determines whether 75% or more of the amino acid residues at a particular position in the amino acid sequence satisfy one of the aforementioned patterns. If so, then the pattern is assigned to that position. It is possible, however, that both patterns l and k may be simultaneously satisfied because they share the same amino acid, specifically aspartic acid. If simultaneous assignment of l and k occurs then pattern m (Level III) is assigned to that position. Likewise, it is possible that both patterns k and o may be simultaneously assigned because they share the same amino acid, specifically glutamic acid. If simultaneous assignment of k and o occurs, then pattern q (Level III) is assigned to that position. If neither a Level II pattern nor the Level III patterns, m and q, satisfy a particular position in the amino acid sequence then the algorithm implements a Level III analysis.

Level III defines pattern sets c, e, m, q, p, and j, wherein m, q, and p share a common amino residue. Pattern q, however, is not tested in the Level III analysis. It is possible that both patterns m and p may be simultaneously satisfied because they share the same amino acid, specifically, glutamic acid. If simultaneous assignment of m and p occurs then pattern r (Level IV) is assigned to that position. If 75% of the amino acids at a pre-selected position in the aligned amino acid sequences satisfy a Level III pattern, then the Level III pattern is assigned to that position. If a Level III pattern cannot be assigned to that position then the algorithm implements a Level IV analysis.

Level IV comprises two non-overlapping patterns f and r. If 75% of the amino acids at a particular position in the amino acid sequence satisfy a Level IV pattern then the pattern is assigned to the position. If no Level IV pattern is assigned the algorithm assigns an X representing any amino acid (Level V) to that position.

Figure 9D:
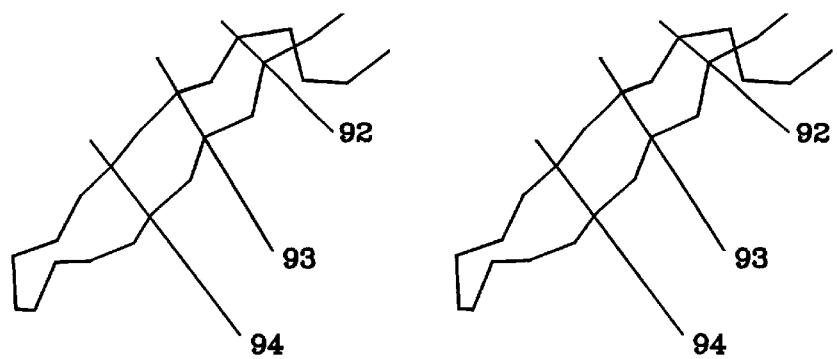
Figure 9E:
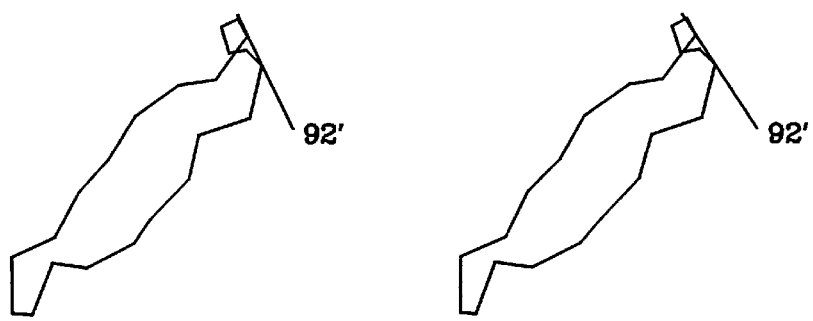
Figure 9F:
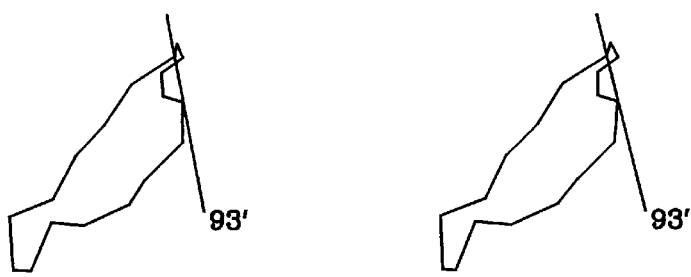
Figure 9G:
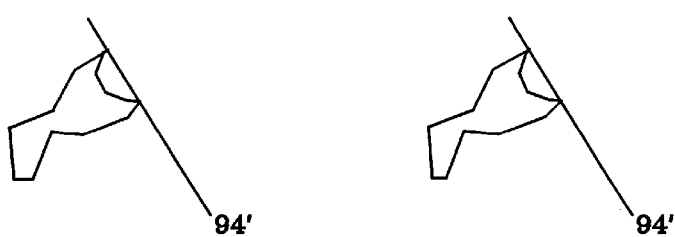
Figure 10:
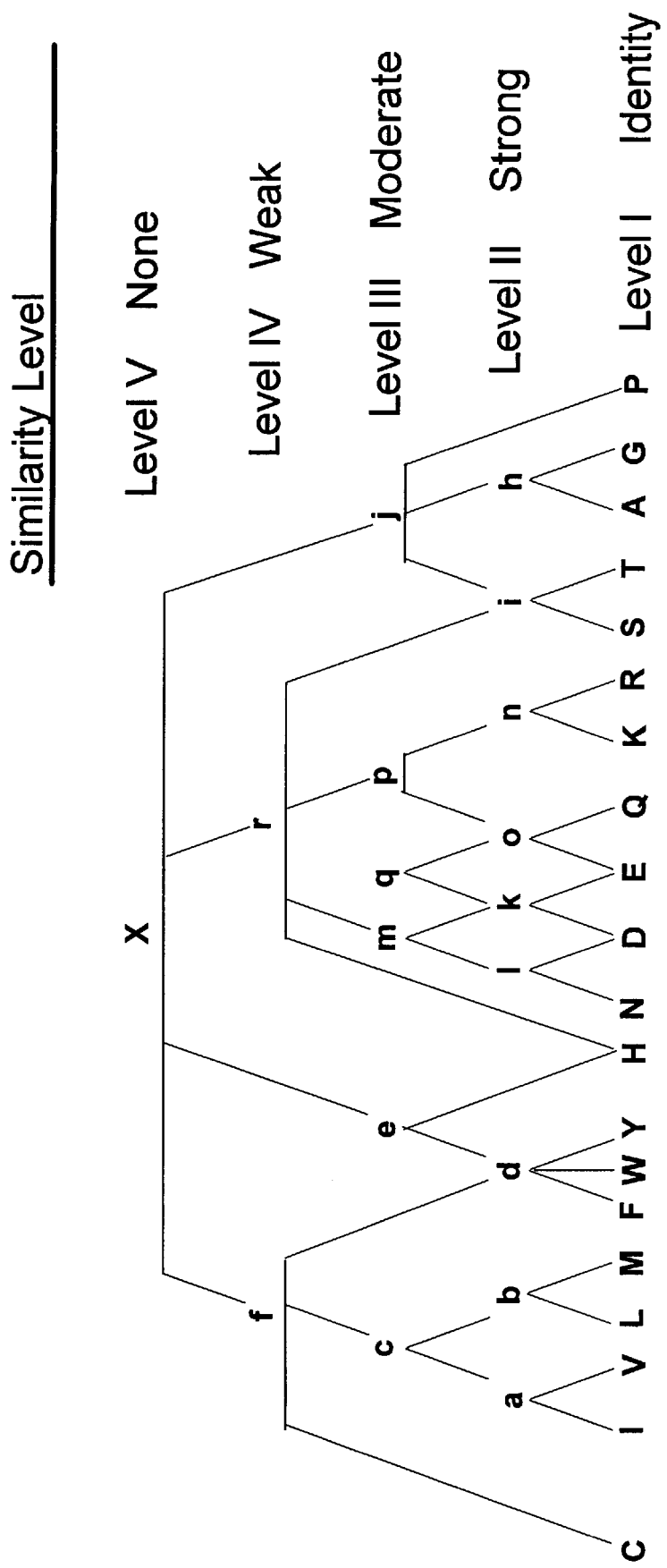

In FIG. 10, Level I lists in upper case letters in single amino acid code the 20 naturally occurring amino acids. Levels II–V define, in lower case letters, groups of amino acids based upon the amino acid hierarchy set forth in Smith et al., supra. The amino acid sequences set forth in FIGS. 5 through 9 were aligned using the aforementioned computer algorithms.

It is contemplated that if the artisan wishes to produce a morphon construct based upon currently identified members of the TGF-β superfamily, then the artisan may use the amino acid sequences shown in FIG. 5 to provide the finger 1, finger 2 and heel regions useful in the production of the morphon constructs of the invention. In the case of members of the TGF-β superfamily discovered hereafter, the amino acid sequence of the new member may be aligned, either manually or by means of a computer algorithm, with the sequences set forth in FIG. 5 to define heel and finger regions useful in the practice of the invention.

Table 1 below summarizes publications which describe the amino acid sequences of each TGF-β superfamily member that were used to produce the sequence alignment patterns set forth in FIGS. 5–9.

TABLE 1

| TGF-β Superfamily Member | SEQ. ID. No. | Publication |
| --- | --- | --- |
| TGF-β1 | 1 | Derynck et al. (1987) Nucl. Acids. Res. 15:3187 |
| TGF-β2 | 2 | Burt et al. (1991) DNA Cell Biol. 10:723–734 |
| TGF-β3 | 3 | Ten Dijke et al. (1988) Proc. Natl. Acad. Sci. USA 85:4715–4719; Derynck et al. (1988) EMBO J. 7:3737–3743. |
| TGF-β4 | 4 | Burt et al. (1992) Mol. Endcrinol. 6:989–922. |
| TGF-β5 | 5 | Kondaiah et al. (1990) J. Biol. Chem 265:1089–1093 |
| dpp | 6 | Padgett et al. (1987) Nature 325:81–84; Paganiban et al. (1990) Mol. Cell Biol. 10:2669–2677. |
| vg-1 | 7 | Weeks et al. (1987) Cell 51:861–867 |
| vgr-1 | 8 | Lyons et al. (1989) Proc. Natl. Acad. Sci USA 86:4554–4558 |
| 60A | 9 | Wharton et al. (1991) Proc. Natl. Acad. Sci. USA 88:9214–9218; Doctor et al. (1992) Dev. Biol. 151:491–505 |
| BMP-2A | 10 | Wozney et al. (1988) Science 242:1528–1534 |
| BMP-3 | 11 | Wozney et al. (1988) Science 242:1528–1534 |
| BMP-4 | 12 | Wozney et al. (1988) Science 242:1528–1534 |
| BMP-5 | 13 | Celeste et al. (1990) Proc. Natl. Acad. Sci. USA 87:9843–9847 |
| BMP-6 | 14 | Celeste et al. (1990) Proc. Natl. Acad. Sci. USA 87:9843–9847 |
| Dorsalin | 15 | Basler et al. (1993) Cell 73:687–702 |
| OP-1 | 16 | Celeste et al. (1990) Proc. Natl. Acad. Sci. USA 87:9843–9847; Ozkaynak et al. (1990) EMBO J. 9:2085–2093 |
| OP-2 | 17 | Ozkaynak et al. (1992) J. Biol. Chem. 267:25220–25227 |
| OP-3 | 18 | Ozkaynak et al. PCT/WO94/10203 Seq. I.D. No. 1. |

TABLE 1-continued

| TGF-β Superfamily Member | SEQ. ID. No. | Publication |
| --- | --- | --- |
| GDF-1 | 19 | Lee (1990) Mol. Endocrinol. 4:1034–1040 |
| GDF-3 | 20 | McPherron et al. (1993) J. Biol. Chem. 268:3444–3449 |
| GDF-9 | 21 | McPherron et al. (1993) J. Biol. Chem. 268:3444–3449 |
| Inhibin α | 22 | Mayo et al. (1986) Proc. Natl. Acad. Sci. USA 83:5849–5853; Stewart et al. (1986) FEBS Lett 206:329–334; Mason et al. (1986) Biochem. Biophys. Res. Commun. 135:957–964 |
| Inhibin βA | 23 | Forage et al. (1986) Proc. Natl. Acad. Sci. USA 83:3091–3095; Chertov et al. (1990) Biomed. Sci. 1:499–506 |
| Inhibin βB | 24 | Mason et al. (1986) Biochem. Biophys. Res. Commun. 135:957–964 |

In particular, it is contemplated that amino acid sequences defining finger 1 regions useful in the practice of the instant invention may be copied directly from the amino acid sequence defining a finger 1 region for any TGF-β superfamily member identified herein. Useful intact finger 1 regions include, but are not limited to

| TGF-β1 | SEQ. ID. No. 1, residues 2 through 29, |
| --- | --- |
| TGF-β2 | SEQ. ID. No. 2, residues 2 through 29, |
| TGF-β3 | SEQ. ID. No. 3, residues 2 through 29, |
| TGF-β4 | SEQ. ID. No. 4, residues 2 through 29, |
| TGF-β5 | SEQ. ID. No. 5, residues 2 through 29, |
| dpp | SEQ. ID. No. 6, residues 2 through 29, |
| Vg-1 | SEQ. ID. No. 7, residues 2 through 29, |
| Vgr-1 | SEQ. ID. No. 8, residues 2 through 29, |
| 60A | SEQ. ID. No. 9, residues 2 through 29, |
| BMP-2A | SEQ. ID. No. 10, residues 2 through 29, |
| BMP-3 | SEQ. ID. No. 11, residues 2 through 29, |
| BMP-4 | SEQ. ID. No. 12, residues 2 through 29, |
| BMP-5 | SEQ. ID. No. 13, residues 2 through 29, |
| BMP-6 | SEQ. ID. No. 14, residues 2 through 29, |
| Dorsalin | SEQ. ID. No. 15, residues 2 through 29, |
| OP-1 | SEQ. ID. No. 16, residues 2 through 29, |
| OP-2 | SEQ. ID. No. 17, residues 2 through 29, |
| OP-3 | SEQ. ID. No. 18, residues 2 through 29, |
| GDF-1 | SEQ. ID. No. 19, residues 2 through 29, |
| GDF-3 | SEQ. ID. No. 20, residues 2 through 29, |
| GDF-9 | SEQ. ID. No. 21, residues 2 through 29, |
| Inhibin α | SEQ. ID. No. 22, residues 2 through 29, |
| Inhibin βA | SEQ. ID. No. 23, residues 2 through 29, and |
| Inhibin βB | SEQ. ID. No. 24, residues 2 through 29. |

It is contemplated also that amino acid sequences defining heel regions useful in the practice of the instant invention may be copied directly from the amino acid sequence defining an intact heel region for any TGF-β superfamily member identified herein. Useful intact heel regions may include, but are not limited to

| TGF-β1 | SEQ. ID. No. 1, residues 35 through 62, |
| --- | --- |
| TGF-β2 | SEQ. ID. No. 2, residues 35 through 62, |
| TGF-β3 | SEQ. ID. No. 3, residues 35 through 62, |
| TGF-β4 | SEQ. ID. No. 4, residues 35 through 62, |
| TGF-β5 | SEQ. ID. No. 5, residues 35 through 62, |
| dpp | SEQ. ID. No. 6, residues 35 through 65, |
| Vg-1 | SEQ. ID. No. 7, residues 35 through 65, |

-continued

| | |
|---|---|
| Vgr-1 | SEQ. ID. No. 8, residues 35 through 65, |
| 60A | SEQ. ID. No. 9, residues 35 through 65, |
| BMP-2 | SEQ. ID. No. 10, residues 35 through 64, |
| BMP3 | SEQ. ID. No. 11, residues 35 through 66, |
| BMP-4 | SEQ. ID. No. 12, residues 35 through 64, |
| BMP-5 | SEQ. ID. No. 13, residues 35 through 65, |
| BMP-6 | SEQ. ID. No. 14, residues 35 through 65, |
| Dorsalin | SEQ. ID. No. 15, residues 35 through 65, |
| OP-1 | SEQ. ID. No. 16, residues 35 through 65, |
| OP-2 | SEQ. ID. No. 17, residues 35 through 65, |
| OP-3 | SEQ. ID. No. 18, residues 35 through 65, |
| GDF-1 | SEQ. ID. No. 19, residues 35 through 70, |
| GDF-3 | SEQ. ID. No. 20, residues 35 through 64, |
| GDF-9 | SEQ. ID. No. 21, residues 35 through 65, |
| Inhibin α | SEQ. ID. No. 22, residues 35 through 65, |
| Inhibin βA | SEQ. ID. No. 23, residues 35 through 69, and |
| Inhibin βB | SEQ. ID. No. 24, residues 35 through 68. |

It is contemplated also that amino acid sequences defining finger 2 regions useful in the practice of the instant invention may be copied directly from the amino acid sequence defining an intact finger 2 region for any TGF-β superfamily member identified herein. Useful intact finger 2 regions may include, but are not limited to

| | |
|---|---|
| TGF-β1 | SEQ. ID. No. 1, residues 65 through 94, |
| TGF-β2 | SEQ. ID. No. 2, residues 65 through 94, |
| TGF-β3 | SEQ. ID. No. 3, residues 65 through 94, |
| TGF-β4 | SEQ. ID. No. 4, residues 65 through 94, |
| TGF-β5 | SEQ. ID. No. 5, residues 65 through 94, |
| dpp | SEQ. ID. No. 6, residues 68 through 98, |
| Vg-1 | SEQ. ID. No. 7, residues 68 through 98, |
| Vgr-1 | SEQ. ID. No. 8, residues 68 through 98, |
| 60A | SEQ. ID. No. 9, residues 68 through 98, |
| BMP-2A | SEQ. ID. No. 10, residues 67 through 97, |
| BMP-3 | SEQ. ID. No. 11, residues 69 through 99, |
| BMP-4 | SEQ. ID. No. 12, residues 67 through 97, |
| BMP-5 | SEQ. ID. No. 13, residues 68 through 98, |
| BMP-6 | SEQ. ID. No. 14, residues 68 through 98, |
| Dorsalin | SEQ. ID. No. 15, residues 68 through 99, |
| OP-1 | SEQ. ID. No. 16, residues 68 through 98, |
| OP-2 | SEQ. ID. No. 17, residues 68 through 98, |
| OP-3 | SEQ. ID. No. 18, residues 68 through 98, |
| GDF-1 | SEQ. ID. No. 19, residues 73 through 103, |
| GDF-3 | SEQ. ID. No. 20, residues 67 through 97, |
| GDF-9 | SEQ. ID. No. 21, residues 68 through 98, |
| Inhibin α | SEQ. ID. No. 22, residues 68 through 101, |
| Inhibin βA | SEQ. ID. No. 23, residues 72 through 102, and |
| Inhibin βB | SEQ. ID. No. 24, residues 71 through 101. |

Furthermore, it is contemplated that the size of the constructs may be reduced significantly by truncating the natural finger and heel regions of the template TGFβ superfamily members, while compensating for dimensional change using linkers as disclosed hereinbelow. Preferred truncated polypeptide sequences that define the finger 1, heel and finger 2 domains are shown in FIGS. 7, 8, and 9, respectively. The truncated polypeptides of the finger and heel regions are defined as: large peptides (typically about 25 amino acids in length); medium peptides (typically about 20 amino acids in length); or small peptides (typically about 16 amino acids in length). Each of the aforementioned large, medium, and small finger and heel region peptides preferably comprise an additional residue(s) i.e., either cys or ser-cys at the N-termini and either cys or cys-ser at the C-termini in order to introduce structure stabilizing disulfide bonds into the constructs. Although, the additional N- and C-terminal serine residues may enhance the water solubility of the constructs, it is anticipated that polar amino acid residues other than serine may likewise be used to enhance solubility of the peptides.

Specifically, FIG. 7 shows preferred amino acid sequences, in a single letter code, for the finger 1 large peptide (FIG. 7A), the finger 1 medium peptide (FIG. 9B) and the finger small peptide (FIG. 7C) for each member of the TGF-β superfamily. Consensus sequence patterns, described in detail below, for each subgroup are shown also at the bottom of each subgroup. In the patterns, upper case letters identify conserved amino acids in the standard single letter amino acid code, the upper case letter "X" indicates that any naturally occurring amino acid is acceptable at that particular location. Lower case letters identify groups of amino acids, in accordance with the pattern definition table set forth in FIG. 10, that also may be introduced into that position without affecting the structure of the resulting morphon construct.

FIG. 7D shows stereo alpha carbon traces illustrating the whole finger 1 region whereas FIGS. 7E, 7F, and 7G, show stereo alpha carbon traces of the finger 1 large, medium, and small peptides, respectively. In FIG. 7D, the lines labeled 72, 73, and 74 pass through the alpha carbons that are cyclized to form the large, medium, and small peptides of the finger 1 region, respectively. The lines with primed labels pass through the cyclized alpha carbons and correspond to the similarly numbered unprimed lines in FIG. 7D. It is apparent from FIGS. 7D–7G that the structural features indicative of the finger 1 region can be maintained while reducing the overall size of the finger 1 element.

It is contemplated that large finger 1 peptides useful in the practice of the instant invention may be selected from a finger 1 sequence belonging any one of the TGF-β superfamily members identified herein. Large finger 1 peptides useful in the practice of the instant invention are set forth below and include, for example:

| | |
|---|---|
| TGF-β1 | SEQ. ID. No. 1, residues 5 through 28, |
| TGF-β2 | SEQ. ID. No. 2, residues 5 through 28, |
| TGF-β3 | SEQ. ID. No. 3, residues 5 through 28, |
| TGF-β4 | SEQ. ID. No. 4, residues 5 through 28, |
| TGF-β5 | SEQ. ID. No. 5, residues 5 through 28, |
| dpp | SEQ. ID. No. 6, residues 5 through 28, |
| Vg-1 | SEQ. ID. No. 7, residues 5 through 28, |
| Vgr-1 | SEQ. ID. No. 8, residues 5 through 28, |
| 60A | SEQ. ID. No. 9, residues 5 through 28, |
| BMP-2A | SEQ. ID. No. 10, residues 5 through 28, |
| BMP-3 | SEQ. ID. No. 11, residues 5 through 28, |
| BMP-4 | SEQ. ID. No. 12, residues 5 through 28, |
| BMP-5 | SEQ. ID. No. 13, residues 5 through 28, |
| BMP-6 | SEQ. ID. No. 14, residues 5 through 28, |
| Dorsalin | SEQ. ID. No. 15, residues 5 through 28, |
| OP-1 | SEQ. ID. No. 16, residues 5 through 28, |
| OP-2 | SEQ. ID. No. 17, residues 5 through 28, |
| OP-3 | SEQ. ID. No. 18, residues 5 through 28, |
| GDF-1 | SEQ. ID. No. 19, residues 5 through 28, |
| GDF-3 | SEQ. ID. No. 20, residues 5 through 28, |
| GDF-9 | SEQ. ID. No. 21, residues 5 through 28, |
| Inhibin α | SEQ. ID. No. 22, residues 5 through 28, |
| Inhibin βA | SEQ. ID. No. 23, residues 5 through 28, and |
| Inhibin βB | SEQ. ID. No. 24, residues 5 through 28, |

In addition, it is contemplated that medium finger 1 peptides useful in the practice of the instant invention may be selected from a finger 1 sequence belonging any one of the TGF-β superfamily members identified herein. Medium finger 1 peptides useful in the practice of the instant invention are set forth below and include, for example:

| | |
|---|---|
| TGF-β1 | SEQ. ID. No. 1, residues 7 through 26, |
| TGF-β2 | SEQ. ID. No. 2, residues 7 through 26, |
| TGF-β3 | SEQ. ID. No. 3, residues 7 through 26, |
| TGF-β4 | SEQ. ID. No. 4, residues 7 through 26, |
| TGF-β5 | SEQ. ID. No. 5, residues 7 through 26, |
| dpp | SEQ. ID. No. 6, residues 7 through 26, |
| Vg-1 | SEQ. ID. No. 7, residues 7 through 26, |
| Vgr-1 | SEQ. ID. No. 8, residues 7 through 26, |
| 60A | SEQ. ID. No. 9, residues 7 through 26, |
| BMP-2A | SEQ. ID. No. 10, residues 7 through 26, |
| BMP-3 | SEQ. ID. No. 11, residues 7 through 26, |
| BMP-4 | SEQ. ID. No. 12, residues 7 through 26, |
| BMP-5 | SEQ. ID. No. 13, residues 7 through 26, |
| BMP-6 | SEQ. ID. No. 14, residues 7 through 26, |
| Dorsalin | SEQ. ID. No. 15, residues 7 through 26, |
| OP-1 | SEQ. ID. No. 16, residues 7 through 26, |
| OP-2 | SEQ. ID. No. 17, residues 7 through 26, |
| OP-3 | SEQ. ID. No. 18, residues 7 through 26, |
| GDF-1 | SEQ. ID. No. 19, residues 7 through 26, |
| GDF-3 | SEQ. ID. No. 20, residues 7 through 26, |
| GDF-9 | SEQ. ID. No. 21, residues 7 through 26, |
| Inhibin α | SEQ. ID. No. 22, residues 7 through 26, |
| Inhibin βA | SEQ. ID. No. 23, residues 7 through 26, and |
| Inhibin βB | SEQ. ID. No. 24, residues 7 through 26, |

In addition, it is contemplated that small finger 1 peptides useful in the practice of the instant invention may be selected from a finger 1 sequence belonging any one the TGF-β superfamily members identified herein. Small finger 1 peptides useful in the practice of the instant invention are set forth below and include, for example:

| | |
|---|---|
| TGF-β1 | SEQ. ID. No. 1, residues 11 through 22, |
| TGF-β2 | SEQ. ID. No. 2, residues 11 through 22, |
| TGF-β3 | SEQ. ID. No. 3, residues 11 through 22, |
| TGF-β4 | SEQ. ID. No. 4, residues 11 through 22, |
| TGF-β5 | SEQ. ID. No. 5, residues 11 through 22, |
| dpp | SEQ. ID. No. 6, residues 11 through 22, |
| Vg-1 | SEQ. ID. No. 7, residues 11 through 22, |
| Vgr-1 | SEQ. ID. No. 8, residues 11 through 22, |
| 60A | SEQ. ID. No. 9, residues 11 through 22, |
| BMP-2A | SEQ. ID. No. 10, residues 11 through 22, |
| BMP-3 | SEQ. ID. No. 11, residues 11 through 22, |
| BMP-4 | SEQ. ID. No. 12, residues 11 through 22, |
| BMP-5 | SEQ. ID. No. 13, residues 11 through 22, |
| BMP-6 | SEQ. ID. No. 14, residues 11 through 22, |
| Dorsalin | SEQ. ID. No. 15, residues 11 through 22, |
| OP-1 | SEQ. ID. No. 16, residues 11 through 22, |
| OP-2 | SEQ. ID. No. 17, residues 11 through 22, |
| OP-3 | SEQ. ID. No. 18, residues 11 through 22, |
| GDF-1 | SEQ. ID. No. 19, residues 11 through 22, |
| GDF-3 | SEQ. ID. No. 20, residues 11 through 22, |
| GDF-9 | SEQ. ID. No. 21, residues 11 through 22, |
| Inhibin α | SEQ. ID. No. 22, residues 11 through 22, |
| Inhibin βA | SEQ. ID. No. 23, residues 11 through 22, and |
| Inhibin βB | SEQ. ID. No. 24, residues 11 through 22. |

Similarly, it is contemplated that the large, medium and small subgroup peptide patterns shown in FIGS. 7A, 7B, and 7C, respectively, for the TGF-β subgroup, the vg/dpp subgroup, the GDF subgroup, and the Inhibin subgroup, likewise may be used in the practice of the instant invention.

FIG. 8 shows preferred amino acid sequences, in a single letter code, for the heel large peptide (FIG. 8A), the heel medium peptide (FIG. 8B) and the heel small peptide (FIG. 8C) for each member of the TGF-β superfamily. Consensus sequence patterns for each subgroup are shown also at the bottom of each subgroup. In the patterns, upper case letters identify conserved amino acid residues in the standard single letter amino acid code, upper case letter "X" indicates that any naturally occurring amino acid is acceptable at that location, lower case letter "z" indicates that any naturally occurring amino acid or a peptide bond is acceptable at that location, and the other lower case letters identify groups of amino acids defined in accordance with the pattern definition table set forth in FIG. 10, that may be introduced at a preselected position in the amino acid sequence without affecting the structure of the resulting morphon construct.

Figure 8D:
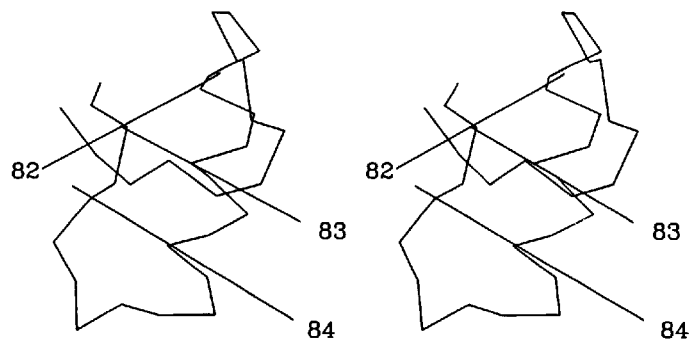
Figure 8E:
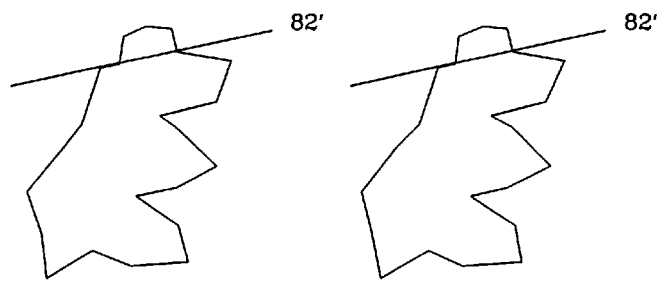
Figure 8F:
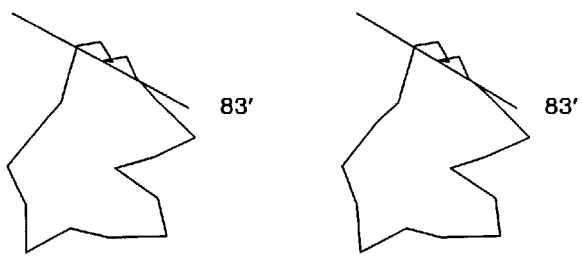
Figure 8G:

FIG. 8D shows stereo alpha carbon traces illustrating the whole heel region, whereas FIGS. 8E, 8F, and 8G show stereo alpha carbon traces of the heel region large, medium, and small peptides, respectively. In FIG. 8D, the lines labeled 82, 83, and 84 pass through the alpha carbons that are cyclized to form the large, medium, and small peptides of the heel region, respectively. The lines with primed labels pass through the cyclized alpha carbons and correspond to the similarly numbered unprimed lines in FIG. 8D. It is apparent from FIGS. 8D–8G that the structural features indicative of the heel region can be maintained while reducing the overall size of the heel element.

It is contemplated that large heel peptides useful in the practice of the instant invention may be selected from a heel region sequence belonging any one of the TGF-β superfamily members identified herein. Large heel peptides useful in the practice of the instant invention are set forth below and include, for example:

| | |
|---|---|
| TGF-β1 | SEQ. ID. No. 1, residues 46 through 61, |
| TGF-β2 | SEQ. ID. No. 2, residues 46 through 61, |
| TGF-β3 | SEQ. ID. No. 3, residues 46 through 61, |
| TGF-β4 | SEQ. ID. No. 4, residues 46 through 61, |
| TGF-β5 | SEQ. ID. No. 5, residues 46 through 61, |
| dpp | SEQ. ID. No. 6, residues 49 through 64, |
| Vg-1 | SEQ. ID. No. 7, residues 49 through 64, |
| Vgr-1 | SEQ. ID. No. 8, residues 49 through 64, |
| 60A | SEQ. ID. No. 9, residues 49 through 64, |
| BMP-2A | SEQ. ID. No. 10, residues 49 through 63, |
| BMP-3 | SEQ. ID. No. 11, residues 49 through 65, |
| BMP-4 | SEQ. ID. No. 12, residues 49 through 63, |
| BMP-5 | SEQ. ID. No. 13, residues 49 through 64, |
| BMP-6 | SEQ. ID. No. 14, residues 49 through 64, |
| Dorsalin | SEQ. ID. No. 15, residues 49 through 64, |
| OP-1 | SEQ. ID. No. 16, residues 49 through 64, |
| OP-2 | SEQ. ID. No. 17, residues 49 through 64, |
| OP-3 | SEQ. ID. No. 18, residues 49 through 64, |
| GDF-1 | SEQ. ID. No. 19, residues 53 through 69, |
| GDF-3 | SEQ. ID. No. 20, residues 49 through 63, |
| GDF-9 | SEQ. ID. No. 21, residues 49 through 64, |
| Inhibin α | SEQ. ID. No. 22, residues 51 through 64, |
| Inhibin βA | SEQ. ID. No. 23, residues 51 through 68, and |
| Inhibin βB | SEQ. ID. No. 24, residues 51 through 67. |

In addition, it is contemplated that medium heel peptides useful in the practice of the instant invention may be selected from a heel sequence belonging any one of the TGF-β superfamily members identified herein. Medium heel peptides useful in the practice of the instant invention are set forth below and include, for example:

| | |
|---|---|
| TGF-β1 | SEQ. ID. No. 1, residues 49 through 61, |
| TGF-β2 | SEQ. ID. No. 2, residues 49 through 61, |
| TGF-β3 | SEQ. ID. No. 3, residues 49 through 61, |
| TGF-β4 | SEQ. ID. No. 4, residues 49 through 61, |
| TGF-β5 | SEQ. ID. No. 5, residues 49 through 61, |
| dpp | SEQ. ID. No. 6, residues 52 through 64, |
| Vg-1 | SEQ. ID. No. 7, residues 52 through 64, |
| Vgr-1 | SEQ. ID. No. 8, residues 52 through 64, |
| 60A | SEQ. ID. No. 9, residues 52 through 64, |
| BMP-2A | SEQ. ID. No. 10, residues 52 through 63, |
| BMP-3 | SEQ. ID. No. 11, residues 52 through 65, |
| BMP-4 | SEQ. ID. No. 12, residues 52 through 63, |

| | -continued |
|---|---|
| BMP-5 | SEQ. ID. No. 13, residues 52 through 64, |
| BMP-6 | SEQ. ID. No. 14, residues 52 through 64, |
| Dorsalin | SEQ. ID. No. 15, residues 52 through 64, |
| OP-1 | SEQ. ID. No. 16, residues 52 through 64, |
| OP-2 | SEQ. ID. No. 17, residues 52 through 64, |
| OP-3 | SEQ. ID. No. 18, residues 52 through 64, |
| GDF-1 | SEQ. ID. No. 19, residues 56 through 69, |
| GDF-3 | SEQ. ID. No. 20, residues 52 through 63, |
| GDF-9 | SEQ. ID. No. 21, residues 52 through 64, |
| Inhibin α | SEQ. ID. No. 22, residues 54 through 64, |
| Inhibin βA | SEQ. ID. No. 23, residues 54 through 68, and |
| Inhibin βB | SEQ. ID. No. 24, residues 54 through 67. |

Furthermore, it is contemplated that small heel peptides useful in the practice of the instant invention may be selected from a heel sequence belonging any one of the TGF-β superfamily members identified herein. Small heel peptides useful in the practice of the instant invention are set forth below and include, for example:

| | |
|---|---|
| TGF-β1 | SEQ. ID. No. 1, residues 53 through 59, |
| TGF-β2 | SEQ. ID. No. 2, residues 53 through 59, |
| TGF-β3 | SEQ. ID. No. 3, residues 53 through 59, |
| TGF-β4 | SEQ. ID. No. 4, residues 53 through 59, |
| TGF-β5 | SEQ. ID. No. 5, residues 53 through 59, |
| dpp | SEQ. ID. No. 6, residues 56 through 62, |
| Vg-1 | SEQ. ID. No. 7, residues 56 through 62, |
| Vgr-1 | SEQ. ID. No. 8, residues 56 through 62, |
| 60A | SEQ. ID. No. 9, residues 56 through 62, |
| BMP-2A | SEQ. ID. No. 10, residues 56 through 61, |
| BMP-3 | SEQ. ID. No. 11, residues 56 through 63, |
| BMP-4 | SEQ. ID. No. 12, residues 56 through 61, |
| BMP-5 | SEQ. ID. No. 13, residues 56 through 62, |
| BMP-6 | SEQ. ID. No. 14, residues 56 through 62, |
| Dorsalin | SEQ. ID. No. 15, residues 56 through 62, |
| OP-1 | SEQ. ID. No. 16, residues 56 through 62, |
| OP-2 | SEQ. ID. No. 17, residues 56 through 62, |
| OP-3 | SEQ. ID. No. 18, residues 56 through 62, |
| GDF-1 | SEQ. ID. No. 19, residues 60 through 67, |
| GDF-3 | SEQ. ID. No. 20, residues 56 through 61, |
| GDF-9 | SEQ. ID. No. 21, residues 56 through 62, |
| Inhibin α | SEQ. ID. No. 22, residues 58 through 62, |
| Inhibin βA | SEQ. ID. No. 22, residues 58 through 66, and |
| Inhibin βB | SEQ. ID. No. 23, residues 58 through 65. |

Similarly, it is contemplated that the large, medium and small heel subgroup peptide patterns shown in FIGS. 8A, 8B, and 8C, respectively, for the TGF-β subgroup, the vg/dpp subgroup, the GDF subgroup, and the Inhibin subgroup, also may be used in the practice of the instant invention.

FIG. 9 shows preferred amino acid sequences, in a single amino acid code for the finger 2 large peptide (FIG. 9A), the finger 2 medium peptide (FIG. 9B) and the finger 2 small peptide (FIG. 9C) for each member of the TGF-β superfamily. Consensus sequence patterns for each subgroup are shown also at the bottom of each subgroup. In the patterns, upper case letters identify conserved amino acids in the standard single letter amino acid code, upper case letter "X" indicates that any naturally occurring amino acid is acceptable at that location, lower case letter "z" indicates that any naturally occurring amino acid or a peptide bond is acceptable at that location, and the other lower case letters identify groups of amino acids, in accordance with the pattern definition table set forth in FIG. 10, that may be introduced at a pre-selected position in the amino acid sequence without affecting the structure of the resulting morphon construct.

FIG. 9D shows stereo alpha carbon traces illustrating the whole finger 2 region, whereas FIGS. 9E, 9F, and 9G show stereo alpha carbon traces of the finger 2 large, medium, and small peptides, respectively. In FIG. 9D, the lines labeled 92, 93, and 94 pass through the alpha carbons that are cyclized to form the large, medium, and small peptides of the finger 2 region, respectively. The lines with primed labels pass through the cyclized alpha carbons and correspond to the similarly numbered unprimed lines in FIG. 9D. It is apparent from FIGS. 9D–9G that the structural features indicative of the finger 2 region can be maintained while reducing the overall size of the finger 2 element.

It is contemplated that large finger 2 peptides useful in the practice of the instant invention may be selected from a finger 2 sequence belonging any one of the TGF-β superfamily members identified herein. Large finger 2 peptides useful in the practice of the instant invention are set forth below and include, for example:

| | |
|---|---|
| TGF-β1 | SEQ. ID. No. 1, residues 72 through 87, |
| TGF-β2 | SEQ. ID. No. 2, residues 72 through 87, |
| TGF-β3 | SEQ. ID. No. 3, residues 72 through 87, |
| TGF-β4 | SEQ. ID. No. 4, residues 72 through 87, |
| TGF-β5 | SEQ. ID. No. 5, residues 72 through 87, |
| dpp | SEQ. ID. No. 6, residues 75 through 91, |
| Vg-1 | SEQ. ID. No. 7, residues 75 through 91, |
| Vgr-1 | SEQ. ID. No. 8, residues 75 through 91, |
| 60A | SEQ. ID. No. 9, residues 75 through 91, |
| BMP-2A | SEQ. ID. No. 10, residues 74 through 90, |
| BMP-3 | SEQ. ID. No. 11, residues 76 through 92, |
| BMP-4 | SEQ. ID. No. 12, residues 74 through 90, |
| BMP-5 | SEQ. ID. No. 13, residues 75 through 91, |
| BMP-6 | SEQ. ID. No. 14, residues 75 through 91, |
| Dorsalin | SEQ. ID. No. 15, residues 75 through 92, |
| OP-1 | SEQ. ID. No. 16, residues 75 through 91, |
| OP-2 | SEQ. ID. No. 17, residues 75 through 91, |
| OP-3 | SEQ. ID. No. 18, residues 75 through 91, |
| GDF-1 | SEQ. ID. No. 19, residues 80 through 96, |
| GDF-3 | SEQ. ID. No. 20, residues 74 through 90, |
| GDF-9 | SEQ. ID. No. 21, residues 75 through 91, |
| Inhibin α | SEQ. ID. No. 22, residues 77 through 94, |
| Inhibin βA | SEQ. ID. No. 23, residues 79 through 95, and |
| Inhibin βB | SEQ. ID. No. 24, residues 78 through 94. |

In addition, it is contemplated that medium finger 2 peptides useful in the practice of the instant invention may be selected from a finger 2 sequence belonging any one of the TGF-β superfamily members identified herein. Medium finger 2 peptides useful in the practice of the instant invention are set forth below and include, for example:

| | |
|---|---|
| TGF-β1 | SEQ. ID. No. 1, residues 74 through 85, |
| TGF-β2 | SEQ. ID. No. 2, residues 74 through 85, |
| TGF-β3 | SEQ. ID. No. 3, residues 74 through 85, |
| TGF-β4 | SEQ. ID. No. 4, residues 74 through 85, |
| TGF-β5 | SEQ. ID. No. 5, residues 74 through 85, |
| dpp | SEQ. ID. No. 6, residues 77 through 89, |
| Vg-1 | SEQ. ID. No. 7, residues 77 through 89, |
| Vgr-1 | SEQ. ID. No. 8, residues 77 through 89, |
| 60A | SEQ. ID. No. 9, residues 77 through 89, |
| BMP-2A | SEQ. ID. No. 10, residues 76 through 88, |
| BMP-3 | SEQ. ID. No. 11, residues 78 through 90, |
| BMP-4 | SEQ. ID. No. 12, residues 76 through 88, |
| BMP-5 | SEQ. ID. No. 13, residues 77 through 89, |
| BMP-6 | SEQ. ID. No. 14, residues 77 through 89, |
| Dorsalin | SEQ. ID. No. 15, residues 77 through 90, |
| OP-1 | SEQ. ID. No. 16, residues 77 through 89, |
| OP-2 | SEQ. ID. No. 17, residues 77 through 89, |
| OP-3 | SEQ. ID. No. 18, residues 77 through 89, |
| GDF-1 | SEQ. ID. No. 19, residues 82 through 94, |
| GDF-3 | SEQ. ID. No. 20, residues 76 through 88, |
| GDF-9 | SEQ. ID. No. 21, residues 77 through 89, |
| Inhibin α | SEQ. ID. No. 22, residues 79 through 92, |

-continued

| | |
|---|---|
| Inhibin βA | SEQ. ID. No. 23, residues 81 through 93, and |
| Inhibin βB | SEQ. ID. No. 24, residues 80 through 92. |

Furthermore, it is contemplated that small finger 2 peptides useful in the practice of the instant invention may be selected from a finger 2 sequence belonging any one of the TGF-β superfamily members identified herein. Small finger 2 peptides useful in the practice of the instant invention are set forth below and include, for example:

| | |
|---|---|
| TGF-β1 | SEQ. ID. No. 1, residues 76 through 83, |
| TGF-β2 | SEQ. ID. No. 2, residues 76 through 83, |
| TGF-β3 | SEQ. ID. No. 3, residues 76 through 83, |
| TGF-β4 | SEQ. ID. No. 4, residues 76 through 83, |
| TGF-β5 | SEQ. ID. No. 5, residues 76 through 83, |
| dpp | SEQ. ID. No. 6, residues 79 through 87, |
| Vg-1 | SEQ. ID. No. 7, residues 79 through 87, |
| Vgr-1 | SEQ. ID. No. 8, residues 79 through 87, |
| 60A | SEQ. ID. No. 9, residues 79 through 87, |
| BMP-2A | SEQ. ID. No. 10, residues 78 through 86, |
| BMP-3 | SEQ. ID. No. 11, residues 80 through 88, |
| BMP-4 | SEQ. ID. No. 12, residues 78 through 86, |
| BMP-5 | SEQ. ID. No. 13, residues 79 through 87, |
| BMP-6 | SEQ. ID. No. 14, residues 79 through 87, |
| Dorsalin | SEQ. ID. No. 15, residues 79 through 88, |
| OP-1 | SEQ. ID. No. 16, residues 79 through 87, |
| OP-2 | SEQ. ID. No. 17, residues 79 through 87, |
| OP-3 | SEQ. ID. No. 18, residues 79 through 87, |
| GDF-1 | SEQ. ID. No. 19, residues 84 through 92, |
| GDF-3 | SEQ. ID. No. 20, residues 78 through 86, |
| GDF-9 | SEQ. ID. No. 21, residues 79 through 87, |
| Inhibin α | SEQ. ID. No. 22, residues 81 through 90, |
| Inhibin βA | SEQ. ID. No. 23, residues 83 through 91, and |
| Inhibin βB | SEQ. ID. No. 24, residues 82 through 90. |

Similarly, it is contemplated that the large, medium and small finger 2 subgroup peptide patterns shown in FIGS. 9A, 9B, and 9C, respectively, for the TGF-β subgroup, the vg/dpp subgroup, the GDF subgroup, and the Inhibin subgroup, also may be used in the practice of the instant invention.

In addition, it is contemplated that the amino acid sequences of the respective finger and heel regions may be altered by amino acid substitution, especially by exploiting substitute residues selected in accordance with the principles disclosed in Smith et al. (1990), supra. Briefly, Smith et al. disclose an amino acid class hierarchy similar to the one summarized in FIG. 10, which may be used to rationally substitute one amino acid for another while minimizing gross conformational distortions of the type which would inactivate protein function. In any event, it is contemplated that many synthetic first finger, second finger, and heel region sequences, having only 70% homology with natural regions, preferably 80%, and most preferably at least 90%, can be used to produce morphon constructs.

Amino acid sequence patterns showing amino acids preferred at each location in the finger and heel regions, deduced in accordance with the principles described in Smith et al. (1990) supra, also are show in FIGS. 5–9, and are referred to as the: TGF-β; Vg/dpp; GDF; and Inhibin subgroup patterns. The amino acid sequences defining the finger 1, heel and finger 2 sequence patterns of each subgroup are set forth in FIGS. 5A, 5B, and 5C, respectively. In addition, the amino acid sequences defining the entire TGF-β, Vg/dpp, GDF and Inhibin subgroup patterns are set forth in the Sequence Listing as SEQ. ID. Nos. 25, 26, 27, and 28, respectively.

Figure 6:
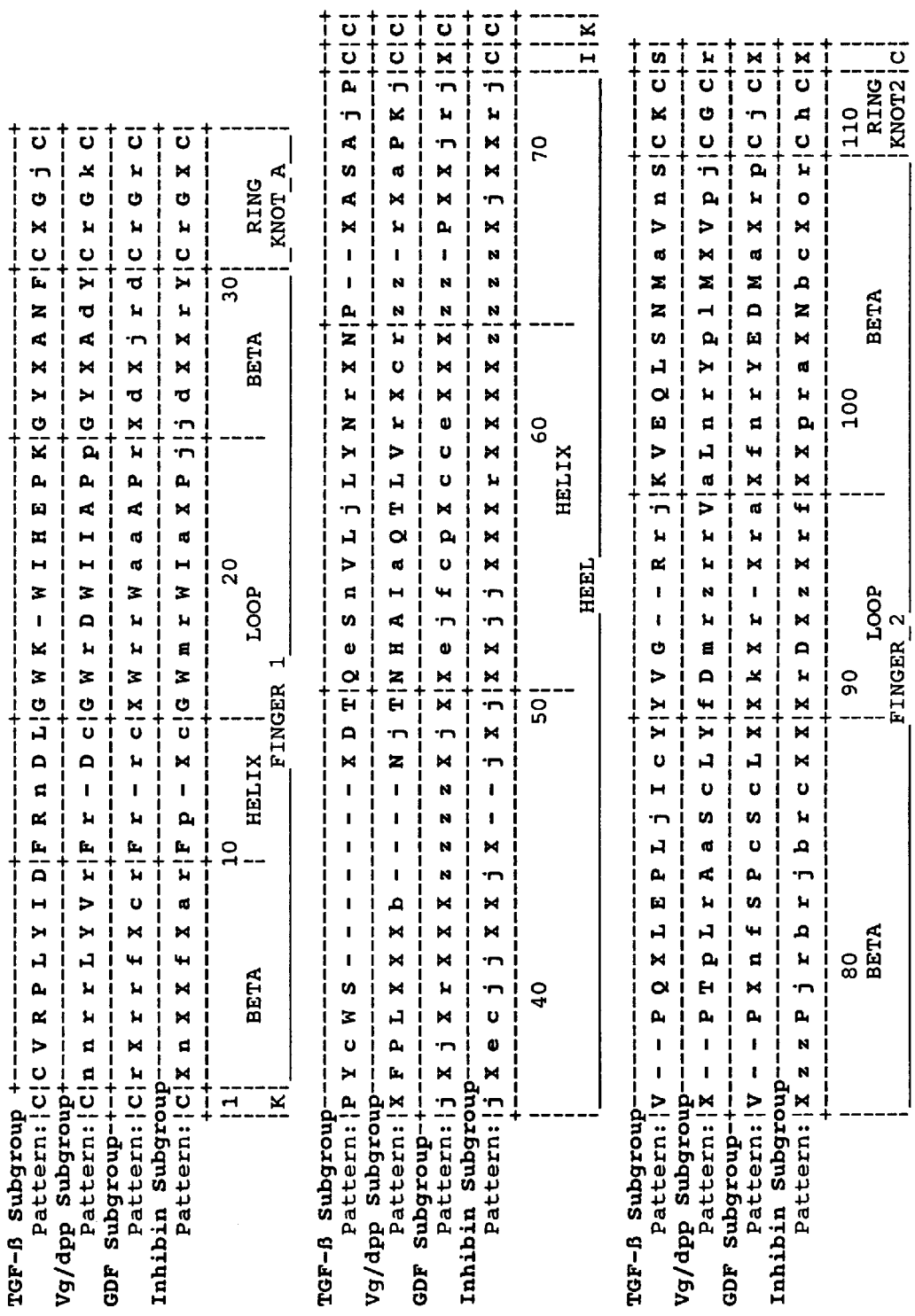

The preferred amino acid sequence patterns for each su bgroup, disclosed in FIGS. 5A, 5B, and 5C, and summarized in FIG. 6, enable one skilled in the art to identify alternative amino acids that may be incorporated at specific positions in the finger 1, heel, and finger 2 elements. The amino acids identified in upper case letters in a single letter amino acid code identify conserved amino acids that together are believed to define structural and functional elements of the finger and heel regions. The upper case letter "X" in FIGS. 5 and 6 indicates that any naturally occurring amino acid is acceptable at that position. The lower case letter "z" in FIGS. 5 and 6 indicates that either a gap or any of the naturally occurring amino acids is acceptable at that position. The lower case letters stand for the amino acids indicated in accordance with the pattern definition table set forth in FIG. 10 and identify groups of amino acids which are useful in that location.

In accordance the amino acid sequence subgroup patterns set forth in FIGS. 5–9, it is contemplated, for example, that the skilled artisan may be able to predict that where applicable, one amino acid may b e substituted by another without inducing disruptive stereochemical changes within the resulting protein construct. For example, in FIG. 5A, in the TGF-β subgroup pattern at residue number 12 it is contemplated that either a lysine residue (K) or a glutamine residue (Q) may be present at this position without affecting the structure of the resulting construct. Accordingly, the sequence pattern at position 12 contains an "n" which in accordance with FIG. 10 defines an amino acid residue selected from the group consisting of lysine or glutamine. It is contemplated, therefore, that many synthetic finger 1, finger 2 and heel region amino acid sequences, having 70% homology, preferably 80%, and most preferably at least 90% with the natural regions, may be used to produce conformationally active constructs of the invention.

In accordance with these principles, it is contemplated that one may design a synthetic morphon construct by starting with the amino acid sequence patterns belonging to the TGF-β, Vg/dpp, GDF, or Inhibin subgroup patterns shown in FIGS. 7 and 6. Thereafter, by using conventional recombinant DNA methodologies a preselected amino acid may be substituted by another as guided by the principles herein and the resulting protein construct tested for binding activity in combination with either agonist or antagonist activity.

The TGF-β subgroup pattern, SEQ. ID. No. 25, accommodates the homologies shared among members of the TGF-β subgroup identified to date including TGF-β1, TGF-β2, TGF-β3, TGF-β4, and TGF-β5. The generic sequence, shown below, includes both the conserved amino acids (standard three letter code) as well as alternative amino acids (Xaa) present at the variable positions within the sequence and defined by the rules set forth in FIG. 10.

TGF-β Subgroup Pattern

```
Cys Cys Val Arg Pro Leu Tyr Ile Asp Phe Arg Xaa Asp
1               5                   10

Leu Gly Trp Lys Trp Ile His Glu Pro Lys Gly Tyr Xaa
        15                  20                  25

Ala Asn Phe Cys Xaa Gly Xaa Cys Pro Tyr Xaa Trp Ser
                30              35

Xaa Asp Thr Gln Xaa Ser Xaa Val Leu Xaa Leu Tyr Asn
40                  45                  50
```

```
                        -continued
Xaa Xaa Asn Pro Xaa Ala Ser Ala Xaa Pro Cys Cys Val
    55          60                          65

Pro Gln Xaa Leu Glu Pro Leu Xaa Ile Xaa Tyr Tyr Val
            70              75

Gly Arg Xaa Xaa Lys Val Glu Gln Leu Ser Asn Met Xaa
    80              85                      90

Val Xaa Ser Cys Lys Cys Ser.
        95
```

Each Xaa can be independently selected from a group of one or more specified amino acids defined as follows, wherein: Xaa12 is Arg or Lys; Xaa26 is Ala, Arg, Asn, Asp, Cys, Glu, Gln, Gly, His, Ile, Leu, Lys, Met, Phe, Pro, Ser, Thr, Trp, Tyr or Val; Xaa31 is Ala, Arg, Asn, Asp, Cys, Glu, Gln, Gly, His, Ile,Leu, Lys, Met, Phe, Pro, Ser. Thr, Trp, Tyr or Val; Xaa33 is Ala, Gly, Pro, Ser, or Thr; Xaa37 is Ile, Leu, Met or Val; Xaa40 isAla, Arg, Asn, Asp, Cys, Glu, Gln, Gly, His, Ile, Leu, Lys, Met, Phe, Pro, Ser, Thr, Trp, Tyr or Val; Xaa44 is His, Phe, Trp or Tyr; Xaa46 is Arg or Lys; Xaa49 is Ala, Gly, Pro, Ser, or Thr; Xaa53 is Arg, Asn, Asp, Gln, Glu, His, Lys, Ser or Thr; Xaa54 is Ala, Arg, Asn, Asp, Cys, Glu, Gln, Gly, His, Ile, Leu, Lys, Met, Phe, Pro, Ser, Thr, Trp, Tyr or Val; Xaa57 is Ala, Arg, Asn, Asp, Cys, Glu, Gln, Gly, His, Ile, Leu, Lys, Met, Phe, Pro, Ser, Thr, Trp, Tyr or Val; Xaa61 is Ala, Gly, Pro, Ser, or Thr; Xaa68 is Ala, Arg, Asn, Asp, Cys, Glu, Gln, Gly, His, Ile, Leu, Lys, Met, Phe, Pro, Ser, Thr, Trp, Tyr or Val; Xaa73 is Ala, Gly, Pro, Ser, or Thr; Xaa75 is Ile, Leu, Met or Val; Xaa81 is Arg, Asn, Asp, Gln, Glu, His, Lys, Ser or Thr; Xaa82 is Ala, Gly, Pro, Ser, or Thr; Xaa91 is Ile or Val; Xaa93 is Arg or Lys.

The Vg/dpp subgroup pattern, SEQ. ID. No. 26, accommodates the homologies shared among members of the Vg/dpp subgroup identified to date including dpp, vg-1, vgr-1, 60A, BMP-2A (BMP-2), Dorsalin, BMP-2B (BMP-4), BMP-3, BMP-5, BMP-6, OP-1 (BMP-7), OP-2 and OP-3. The generic sequence, below, includes both the conserved amino acids (standard three letter code) as well as alternative amino acids (Xaa) present at the variable positions within the sequence and defined by the rules set forth in FIG. 10.

```
                    Vgg/dpp Subgroup Pattern
Cys Xaa Xaa Xaa Xaa Leu Tyr Val Xaa Phe Xaa Asp Xaa
1               5                   10

Gly Trp Xaa Asp Trp Ile Ile Ala Pro Xaa Gly Tyr Xaa
    15              20                  25

Ala Xaa Tyr Cys Xaa Gly Xaa Cys Xaa Phe Pro Leu Xaa
            30              35

Xaa Xaa Xaa Asn Xaa Thr Asn His Ala Ile Xaa Gln Thr
40              45                      50

Leu Val Xaa Xaa Xaa Xaa Xaa Xaa Xaa Xaa Xaa Pro Lys
        55              60                      65

Xaa Cys Cys Xaa Pro Thr Xaa Leu Xaa Ala Xaa Ser Xaa
                70              75

Leu Tyr Xaa Asp Xaa Xaa Xaa Xaa Xaa Val Xaa Leu Xaa
        80              85                  90

Xaa Tyr Xaa Xaa Met Xaa Val Xaa Xaa Cys Gly Cys
            95                  100

Xaa.
```

Each Xaa can be independently selected from a group of one or more specified amino acids defined as follows, wherein: Xaa2 is Arg or Lys; Xaa3 is Arg or Lys; Xaa4 is Arg, Asn, Asp, Gln, Glu, His, Lys, Ser or Thr; Xaa5 is Arg, Asn, Asp, Gln, Glu, His, Lys, Ser or Thr; Xaa9 is Arg, Asn, Asp, Gln, Glu, His, Lys, Ser or Thr; Xaa11 is Arg, Asn, Asp, Gln, Glu, His, Lys, Ser or Thr; Xaa13 is Ile, Leu, Met or Val; Xaa16 is Arg, Asn, Asp, Gln, Glu, His, Lys, Ser or Thr; Xaa23 is Arg, Gln, Glu,or Lys; Xaa26 is Ala, Arg, Asn, Asp, Cys, Glu, Gln, Gly, His, Ile, Leu, Lys, Met, Phe, Pro, Ser, Thr, Trp, Tyr or Val; Xaa28 is Phe, Trp or Tyr; Xaa31 is Arg, Asn, Asp, Gln, Glu, His, Lys, Ser or Thr; Xaa33 is Asp or Glu; Xaa35 is Ala, Arg, Asn, Asp, Cys, Glu, Gln, Gly, His, Ile, Leu, Lys, Met, Phe, Pro, Ser, Thr, Trp, Tyr or Val; Xaa39 is Ala, Arg, Asn, Asp, Cys, Glu, Gln, Gly, His, Ile, Leu, Lys, Met, Phe, Pro, Ser, Thr, Trp, Tyr or Val; Xaa40 is Ala, Arg, Asn, Asp, Cys, Glu, Gln, Gly, His, Ile, Leu, Lys, Met, Phe, Pro, Ser, Thr, Trp, Tyr or Val; Xaa41 is Ala, Arg, Asn, Asp, Cys, Glu, Gln, Gly, His, Ile, Leu, Lys, Met, Phe, Pro, Ser, Thr, Trp, Tyr or Val; Xaa42 is Leu or Met; Xaa44 is Ala, Gly, Pro, Ser, or Thr; Xaa50 is Ile or Val; Xaa55 is Arg, Asn, Asp, Gln, Glu, His, Lys, Ser or Thr; Xaa56 is Ala, Arg, Asn, Asp, Cys, Glu, Gln, Gly, His, Ile, Leu, Lys, Met, Phe, Pro, Ser, Thr, Trp, Tyr or Val; Xaa57 is Ile, Leu, Met or Val; Xaa58 is Arg, Asn, Asp, Gln, Glu, His, Lys, Ser or Thr; Xaa59 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa60 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa61 is Arg, Asn, Asp, Gln, Glu, His, Lys, Ser or Thr; Xaa62 is Ala, Arg, Asn, Asp, Cys, Glu, Gln, Gly, His, Ile, Leu, Lys, Met, Phe, Pro, Ser, Thr, Trp, Tyr or Val; Xaa63 is Ile or Val; Xaa66 is Ala, Gly, Pro, Ser, or Thr; Xaa69 is Ala, Arg, Asn, Asp, Cys, Glu, Gln, Gly, His, Ile, Leu, Lys, Met, Phe, Pro, Ser, Thr, Trp, Tyr or Val; Xaa72 is Arg, Gln, Glu,or Lys; Xaa74 is Arg, Asn, Asp, Gln, Glu, His, Lys, Ser or Thr; Xaa76 is Ile or Val; Xaa78 is Ile, Leu, Met or Val; Xaa81 is Cys, Ile, Leu, Met, Phe, Trp, Tyr or Val; Xaa83 is Asn, Asp or Glu; Xaa84 is Arg, Asn, Asp, Gln, Glu, His, Lys, Ser or Thr; Xaa85 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa86 is Arg, Asn, Asp, Gln, Glu, His, Lys, Ser or Thr; Xaa87 is Arg, Asn, Asp, Gln, Glu, His, Lys, Ser or Thr; Xaa89 is Ile or Val; Xaa91 is Arg or Lys; Xaa92 is Arg, Asn, Asp, Gln, Glu, His, Lys, Ser or Thr; Xaa94 is Arg, Gln, Glu,or Lys; Xaa95 is Asn or Asp; Xaa97 is Ala, Arg, Asn, Asp, Cys, Glu, Gln, Gly, His, Ile, Leu, Lys, Met, Phe, Pro, Ser, Thr, Trp, Tyr or Val; Xaa99 is Arg, Gln, Glu, or Lys; Xaa100 is Ala, Gly, Pro, Ser, or Thr; Xaa104 is Arg, Asn, Asp, Gln, Glu, His, Lys, Ser or Thr.

The GDF subgroup pattern, SEQ. ID. No. 27, accommodates the homologies shared among members of the GDF subgroup identified to date including GDF-1, GDF-3, and GDF-9. The generic sequence, shown below, includes both the conserved amino acids (standard three letter code) as well as alternative amino acids (Xaa) present at the variable positions within the sequence and defined by the rules set forth in FIG. 10.

```
                    GDF Subgroup Pattern
Cys Xaa Xaa Xaa Xaa Xaa Xaa Xaa Xaa Phe Xaa Xaa Xaa
1               5                   10

Xaa Trp Xaa Xaa Trp Xaa Xaa Ala Pro Xaa Xaa Xaa Xaa
    15              20                  25
```

```
Xaa Xaa Xaa Cys Xaa Gly Xaa Cys Xaa Xaa Xaa Xaa
            30          35

Xaa Xaa Xaa Xaa Xaa Xaa Xaa Xaa Xaa Xaa Xaa Xaa
40              45                  50

Xaa Xaa Xaa Xaa Xaa Xaa Xaa Xaa Xaa Xaa Xaa Pro
        55              60                  65

Xaa Xaa Xaa Xaa Xaa Xaa Cys Val Pro Xaa Xaa Xaa Ser
                70              75

Pro Xaa Ser Xaa Leu Xaa Xaa Xaa Xaa Xaa Xaa Xaa
    80              85                  90

Xaa Xaa Xaa Xaa Tyr Glu Asp Met Xaa Xaa Xaa Xaa Cys
            95              100

Xaa Cys Xaa.
105
```

Each Xaa can be independently selected from a group of one or more specified amino acids defined as follows, wherein: Xaa2 is Arg, Asn, Asp, Gln, Glu, His, Lys, Ser or Thr; Xaa3 is Ala, Arg, Asn, Asp, Cys, Glu, Gln, Gly, His, Ile, Leu, Lys, Met, Phe, Pro, Ser, Thr, Trp, Tyr or Val; Xaa4 is Arg, Asn, Asp, Gln, Glu, His, Lys, Ser or Thr; Xaa5 is Arg, Asn, Asp, Gln, Glu, His, Lys, Ser or Thr; Xaa6 is Cys, Ile, Leu, Met, Phe, Trp, Tyr or Val; Xaa7 is Ala, Arg, Asn, Asp, Cys, Glu, Gln, Gly, His, Ile, Leu, Lys, Met, Phe, Pro, Ser, Thr, Trp, Tyr or Val; Xaa8 is Ile, Leu, Met or Val; Xaa9 is Arg, Asn, Asp, Gln, Glu, His, Lys, Ser or Thr; Xaa11 is Arg, Asn, Asp, Gln, Glu, His, Lys, Ser or Thr; Xaa12 is Arg, Asn, Asp, Gin, Glu, His, Lys, Ser or Thr; Xaa13 is Ile, Leu, Met or Val; Xaa14 is Ala, Arg, Asn, Asp, Cys, Glu, Gln, Gly, His, Ile, Leu, Lys, Met, Phe, Pro, Ser, Thr, Trp, Tyr or Val; Xaa16 is Arg, Asn, Asp, Gln, Glu, His, Lys, Ser or Thr; Xaa17 is Arg, Asn, Asp, Gln, Glu, His, Lys, Ser or Thr; Xaa19 is Ile or Val; Xaa20 is lle or Val; Xaa23 is Arg, Asn, Asp, Gln, Glu, His, Lys, Ser or Thr; Xaa24 is Ala, Arg, Asn, Asp, Cys, Glu, Gln, Gly, His, Ile, Leu, Lys, Met, Phe, Pro, Ser, Thr, Trp, Tyr or Val; Xaa25 is Phe, Trp or Tyr; Xaa26 is Ala, Arg, Asn, Asp, Cys, Glu, Gln, Gly, His, Ile, Leu, Lys, Met, Phe, Pro, Ser, Thr, Trp, Tyr or Val; Xaa27 is Ala, Gly, Pro, Ser, or Thr; Xaa28 is Arg, Asn, Asp, Gln, Glu, His, Lys, Ser or Thr; Xaa29 is Phe, Trp or Tyr; Xaa31 is Arg, Asn, Asp, Gln, Glu, His, Lys, Ser or Thr; Xaa33 is Arg, Asn, Asp, Gln, Glu, His, Lys, Ser or Thr; Xaa35 is Ala, Gly, Pro, Ser, or Thr; Xaa36 is Ala, Arg, Asn, Asp, Cys, Glu, Gln, Gly, His, Ile, Leu, Lys, Met, Phe, Pro, Ser, Thr, Trp, Tyr or Val; Xaa37 is Ala, Gly, Pro, Ser, or Thr; Xaa38 is Ala, Arg, Asn, Asp, Cys, Glu, Gln, Gly, His, Ile, Leu, Lys, Met, Phe, Pro, Ser, Thr, Trp, Tyr or Val; Xaa39 is Arg, Asn, Asp, Gln, Glu, His, Lys, Ser or Thr; Xaa40 is Ala, Arg, Asn, Asp, Cys, Glu, Gln, Gly, His, Ile, Leu, Lys, Met, Phe, Pro, Ser, Thr, Trp, Tyr or Val; Xaa41 is Ala, Arg, Asn, Asp, Cys, Glu, Gln, Gly, His, Ile, Leu, Lys, Met, Phe, Pro, Ser, Thr, Trp, Tyr or Val; Xaa42 is Ala, Arg, Asn, Asp, Cys, Glu, Gln, Gly, His, Ile, Leu, Lys, Met, Phe, Pro, Ser, Thr, Trp, Tyr or Val; Xaa43 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa44 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa45 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa46 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa47 is Ala, Arg, Asn, Asp, Cys, Glu, Gln, Gly, His, lie, Leu, Lys, Met, Phe, Pro, Ser, Thr, Trp, Tyr or Val; Xaa48 is Ala, Gly, Pro, Ser, or Thr; Xaa49 is Ala, Arg, Asn, Asp, Cys, Glu, Gln, Gly, His, Ile, Leu, Lys, Met, Phe, Pro, Ser, Thr, Trp, Tyr or Val; Xaa50 is Ala, Arg, Asn, Asp, Cys, Glu, Gln, Gly, His, Ile, Leu, Lys, Met, Phe, Pro, Ser, Thr, Trp, Tyr or Val; Xaa51 is His, Phe, Trp or Tyr; Xaa52 is Ala, Gly, Pro, Ser, or Thr; Xaa53 is Cys, Ile, Leu, Met, Phe, Trp, Tyr or Val; Xaa54 is Ile, Leu, Met or Val; Xaa55 is Arg, Gln, Glu,or Lys; Xaa56 is Ala, Arg, Asn, Asp, Cys, Glu, Gln, Gly, His, Ile, Leu, Lys, Met, Phe, Pro, Ser, Thr, Trp, Tyr or Val; Xaa57 is Ile, Leu, Met or Val; Xaa58 is Ile, Leu, Met or Val; Xaa59 is His, Phe, Trp or Tyr; Xaa60 is Ala, Arg, Asn, Asp, Cys, Glu, Gln, Gly, His, Ile, Leu, Lys, Met, Phe, Pro, Ser, Thr, Trp, Tyr or Val; Xaa61 is Ala, Arg, Asn, Asp, Cys, Glu, Gin, Gly, His, Ile, Leu, Lys, Met, Phe, Pro, Ser, Thr, Trp, Tyr or Val; Xaa62 is Ala, Arg, Asn, Asp, Cys, Glu, Gln, Gly, His, Ile, Leu, Lys, Met, Phe, Pro, Ser, Thr, Trp, Tyr or Val; Xaa63 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa64 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa66 is Ala, Arg, Asn, Asp, Cys, Glu, Gln, Gly, His, Ile, Leu, Lys, Met, Phe, Pro, Ser, Thr, Trp, Tyr or Val; Xaa67 is Ala, Arg, Asn, Asp, Cys, Glu, Gln, Gly, His, Ile, Leu, Lys, Met, Phe, Pro, Ser, Thr, Trp, Tyr or Val; Xaa68 is Ala, Gly, Pro, Ser, or Thr; Xaa69 is Arg, Asn, Asp, Gln, Glu, His, Lys, Ser or Thr; Xaa70 is Ala, Gly, Pro, Ser, or Thr; Xaa71 is Ala, Arg, Asn, Asp, Cys, Glu, Gln, Gly, His, Ile, Leu, Lys, Met, Phe, Pro, Ser, Thr, Trp, Tyr or Val; Xaa75 is Ala, Arg, Asn, Asp, Cys, Glu, Gln, Gly, His, Ile, Leu, Lys, Met, Phe, Pro, Ser, Thr, Trp, Tyr or Val; Xaa76 is Arg or Lys; Xaa77 is Cys, Ile, Leu, Met, Phe, Trp, Tyr or Val; Xaa80 is Ile, Leu, Met or Val; Xaa82 is Ile, Leu, Met or Val; Xaa84 is Ala, Arg, Asn, Asp, Cys, Glu, Gln, Gly, His, Ile, Leu, Lys, Met, Phe, Pro, Ser, Thr, Trp, Tyr or Val; Xaa85 is Ala, Arg, Asn, Asp, Cys, Glu, Gln, Gly, His, Ile, Leu, Lys, Met, Phe, Pro, Ser, Thr, Trp, Tyr or Val; Xaa86 is Asp or Glu; Xaa87 is Ala, Arg, Asn, Asp, Cys, Glu, Gln, Gly, His, Ile, Leu, Lys, Met, Phe, Pro, Ser, Thr, Trp, Tyr or Val; Xaa88 is Arg, Asn, Asp, Gln, Glu, His, Lys, Ser or Thr; Xaa89 is Ala, Arg, Asn, Asp, Cys, Glu, Gln, Gly, His, Ile, Leu, Lys, Met, Phe, Pro, Ser, Thr, Trp, Tyr or Val; Xaa90 is Arg, Asn, Asp, Gln, Glu, His, Lys, Ser or Thr; Xaa91 is Ile or Val; Xaa92 is Ala, Arg, Asn, Asp, Cys, Giu, Gin, Gly, His, lie, Leu, Lys, Met, Phe, Pro, Ser, Thr, Trp, Tyr or Val; Xaa93 is Cys, Ile, Leu, Met, Phe, Trp, Tyr or Val; Xaa94 is Arg or Lys; Xaa95 is Arg, Asn, Asp, Gin, Glu, His, Lys, Ser or Thr; Xaa100 is Ile or Val; Xaa101 is Ala, Arg, Asn, Asp, Cys, Glu, Gin, Gly, His, lie, Leu, Lys, Met, Phe, Pro, Ser, Thr, Trp, Tyr or Val; Xaa102 is Arg, Asn, Asp, Gin, Glu, His, Lys, Ser or Thr; Xaa103 is Arg, Gln, Glu, or Lys; Xaa105 is Ala, Gly, Pro, Ser, or Thr; Xaa107 is Ala, Arg, Asn, Asp, Cys, Glu, Gin, Gly, His, Ile, Leu, Lys, Met, Phe, Pro, Ser, Thr, Trp, Tyr or Val.

The Inhibin subgroup pattern, SGQ. ID. No. 28, accommodates the homologies shared among members of the Inhibin subgroup identified to date including Inhibin α, Inhibin βA and Inhibin βB. The generi c sequence, shown below, includes both the conserved amino acids (standard three letter code) as well as alternative amino acids (Xaa) present at the variable positions within the sequence and defined by the rules set forth in FIG. 10.

```
              Inhibin Subgroup pattern
Cys Xaa Xaa Xaa Xaa Xaa Xaa Xaa Xaa Phe Xaa Xaa Xaa
1               5                       10

Gly Trp Xaa Xaa Trp Ile Xaa Xaa Pro Xaa Xaa Xaa Xaa
        15              20                      25

Xaa Xaa Tyr Cys Xaa Gly Xaa Cys Xaa Xaa Xaa Xaa
            30              35

Xaa Xaa Xaa Xaa Xaa Xaa Xaa Xaa Xaa Xaa Xaa
40                  45                      50

Xaa Xaa Xaa Xaa Xaa Xaa Xaa Xaa Xaa Xaa Xaa
        55              60                  65

Xaa Xaa Xaa Xaa Cys Cys Xaa Xaa Pro Xaa Xaa Xaa
                70              75

Xaa Xaa Xaa Xaa Xaa Xaa Xaa Xaa Asp Xaa Xaa Xaa
80                      85                  90

Xaa Xaa Xaa Xaa Xaa Xaa Xaa Xaa Asn Xaa Xaa Xaa
            95                  100

Xaa Cys Xaa Cys Xaa.
105
```

Each Xaa can be independently selected from a group of one or more specified amino acids defined as follows, wherein: Xaa2 is Ala, Arg, Asn, Asp, Cys, Giu, Gin, Gly, His, Ile, Leu, Lys, Met, Phe, Pro, Ser, Thr, Trp, Tyr or Val; Xaa3 is Arg or Lys; Xaa4 is Ala, Arg, Asn, Asp, Cys, Glu, Gin, Gly, His, Ile, Leu, Lys, Met, Phe, Pro, Ser, Thr, Trp, Tyr or Val; Xaa5 is Ala, Arg, Asn, Asp, Cys, Glu, Gln, Gly, His, Ile, Leu, Lys, Met, Phe, Pro, Ser, Thr, Trp, Tyr or Val; Xaa6 is Cys, Ile, Leu, Met, Phe, Trp, Tyr or Val; Xaa7 is Ala, Arg, Asn, Asp, Cys, Glu, Gln, Gly, His, Ile, Leu, Lys, Met, Phe, Pro, Ser, Thr, Trp, Tyr or Val; Xaa8 is Ile or Val; Xaa9 is Arg, Asn, Asp, Gln, Glu, His, Lys, Ser or Thr; Xaa11 is Arg, Gln, Glu,or Lys; Xaa12 is Ala, Arg, Asn, Asp, Cys, Glu, Gin, Gly, His, Ile, Leu, Lys, Met, Phe, Pro, Ser, Thr, Trp, Tyr or Val; Xaa13 is Ile, Leu, Met or Val; Xaa16 is Asn, Asp or Glu; Xaa17 is Arg, Asn, Asp, Gln, Glu, His, Lys, Ser or Thr; Xaa20 is Ile or Val; Xaa21 is Ala, Arg, Asn, Asp, Cys, Glu, Gln, Gly, His, Ile, Leu, Lys, Met, Phe, Pro, Ser, Thr, Trp, Tyr or Val; Xaa23 is Ala, Gly, Pro, Ser, or Thr; Xaa24 is Ala, Gly, Pro, Ser, or Thr; Xaa25 is Phe, Trp or Tyr; Xaa26 is Ala, Arg, Asn, Asp, Cys, Glu, Gln, Gly, His, Ile, Leu, Lys, Met, Phe, Pro, Ser, Thr, Trp, Tyr or Val; Xaa27 is Ala, Arg, Asn, Asp, Cys, Glu, Gln, Gly, His, Ile, Leu, Lys, Met, Phe, Pro, Ser, Thr, Trp, Tyr or Val; Xaa28 is Arg, Asn, Asp, Gin, Glu, His, Lys, Ser or Thr; Xaa31 is Arg, Asn, Asp, Gln, Glu, His, Lys, Ser or Thr; Xaa33 is Ala, Arg, Asn, Asp, Cys, Glu, Gln, Gly, His, Ile, Leu, Lys, Met, Phe, Pro, Ser, Thr, Trp, Tyr or Val; Xaa35 is Ala, Gly, Pro, Ser, or Thr; Xaa36 is Ala, Arg, Asn, Asp, Cys, Glu, Gln, Gly, His, Ile, Leu, Lys, Met, Phe, Pro, Ser, Thr, Trp, Tyr or Val; Xaa37 is His, Phe, Trp or Tyr; Xaa38 is Ile, Leu, Met or Val; Xaa39 is Ala, Gly, Pro, Ser, or Thr; Xaa40 is Ala, Gly, Pro, Ser, or Thr; Xaa41 is Ala, Arg, Asn, Asp, Cys, Glu, Gln, Gly, His, Ile, Leu, Lys, Met, Phe, Pro, Ser, Thr, Trp, Tyr or Val; Xaa42 is Ala, Arg, Asn, Asp, Cys, Glu, Gln, Gly, His, Ile, Leu, Lys, Met, Phe, Pro, Ser, Thr, Trp, Tyr or Val; Xaa43 is Ala, Gly, Pro, Ser, or Thr; Xaa44 is Ala, Arg, Asn, Asp, Cys, Glu, Gln, Gly, His, Ile, Leu, Lys, Met, Phe, Pro, Ser, Thr, Trp, Tyr or Val; Xaa45 is Ala, Gly, Pro, Ser, or Thr; Xaa46 is Ala, Arg, Asn, Asp, Cys, Glu, Gln, Gly, His, Ile, Leu, Lys, Met, Phe, Pro, Ser, Thr, Trp, Tyr or Val; Xaa47 is Ala, Gly, Pro, Ser, or Thr; Xaa48 is Ala, Arg, Asn, Asp, Cys, Glu, Gln, Gly, His, Ile, Leu, Lys, Met, Phe, Pro, Ser, Thr, Trp, Tyr or Val; Xaa49 is Ala, Arg, Asn, Asp, Cys, Glu, Gln, Gly, His, Ile, Leu, Lys, Met, Phe, Pro, Ser, Thr, Trp, Tyr or Val; Xaa50 is Ala, Gly, Pro, Ser, or Thr; Xaa51 is Ala, Gly, Pro, Ser, or Thr; Xaa52 is Ala, Arg, Asn, Asp, Cys, Glu, Gln, Gly, His, Ile, Leu, Lys, Met, Phe, Pro, Ser, Thr, Trp, Tyr or Val; Xaa53 is Ala, Arg, Asn, Asp, Cys, Glu, Gln, Gly, His, Ile, Leu, Lys, Met, Phe, Pro, Ser, Thr, Trp, Tyr or Val; Xaa54 is Ala, Arg, Asn, Asp, Cys, Glu, Gln, Gly, His, Ile, Leu, Lys, Met, Phe, Pro, Ser, Thr, Trp, Tyr or Val; Xaa55 is Arg, Asn, Asp, Gln, Glu, His, Lys, Ser or Thr; Xaa56 is Ala, Arg, Asn, Asp, Cys, Glu, Gln, Gly, His, Ile, Leu, Lys, Met, Phe, Pro, Ser, Thr, Trp, Tyr or Val; Xaa57 is Ala, Arg, Asn, Asp, Cys, Glu, Gln, Gly, His, Ile, Leu, Lys, Met, Phe, Pro, Ser, Thr, Trp, Tyr or Val; Xaa58 is Ala, Arg, Asn, Asp, Cys, Glu, Gln, Gly, His, Ile, Leu, Lys, Met, Phe, Pro, Ser, Thr, Trp, Tyr or Val; Xaa59 is Ala, Arg, Asn, Asp, Cys, Glu, Gln, Gly, His, Ile, Leu, Lys, Met, Phe, Pro, Ser, Thr, Trp, Tyr or Val; Xaa60 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa61 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa62 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa63 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa64 is Ala, Arg, Asn, Asp, Cys, Glu, Gln, Gly, His, Ile, Leu, Lys, Met, Phe, Pro, Ser, Thr, Trp, Tyr or Val; Xaa65 is Ala, Gly, Pro, Ser, or Thr; Xaa66 is Ala, Arg, Asn, Asp, Cys, Glu, Gln, Gly, His, Ile, Leu, Lys, Met, Phe, Pro, Ser, Thr, Trp, Tyr or Val; Xaa67 is Ala, Arg, Asn, Asp, Cys, Glu, Gln, Gly, His, Ile, Leu, Lys, Met, Phe, Pro, Ser, Thr, Trp, Tyr or Val; Xaa68 is Arg, Asn, Asp, Gln, Glu, His, Lys, Ser or Thr; Xaa69 is Ala, Gly, Pro, Ser, or Thr; Xaa72 is Ala, Arg, Asn, Asp, Cys, Glu, Gln, Gly, His, Ile, Leu, Lys, Met, Phe, Pro, Ser, Thr, Trp, Tyr or Val; Xaa73 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa74 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa76 is Ala, Gly, Pro, Ser, or Thr; Xaa77 is Arg, Asn, Asp, Gln, Glu, His, Lys, Ser or Thr; Xaa78 is Leu or Met; Xaa79 is Arg, Asn, Asp, Gln, Glu, His, Lys, Ser or Thr; Xaa80 is Ala, Gly, Pro, Ser, or Thr; Xaa81 is Leu or Met; Xaa82 is Arg, Asn, Asp, Gln, Glu, His, Lys, Ser or Thr; Xaa83 is Ile, Leu, Met or Val; Xaa84 is Ala, Arg, Asn, Asp, Cys, Glu, Gln, Gly, His, Ile, Leu, Lys, Met, Phe, Pro, Ser, Thr, Trp, Tyr or Val; Xaa85 is Ala, Arg, Asn, Asp, Cys, Glu, Gln, Gly, His, Ile, Leu, Lys, Met, Phe, Pro, Ser, Thr, Trp, Tyr or Val; Xaa86 is Ala, Arg, Asn, Asp, Cys, Glu, Gln, Gly, His, Ile, Leu, Lys, Met, Phe, Pro, Ser, Thr, Trp, Tyr or Val; Xaa87 is Arg, Asn, Asp, Gln, Glu, His, Lys, Ser or Thr; Xaa89 is Ala, Arg, Asn, Asp, Cys, Glu, Gln, Gly, His, Ile, Leu, Lys, Met, Phe, Pro, Ser, Thr, Trp, Tyr or Val; Xaa90 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa91 is Ala, Arg, Asn, Asp, Cys, Glu, Gln, Gly, His, Ile, Leu, Lys, Met, Phe, Pro, Ser, Thr, Trp, Tyr or Val; Xaa92 is Arg, Asn, Asp, Gln, Glu, His, Lys, Ser or Thr; Xaa93 is Cys, Ile, Leu, Met, Phe, Trp, Tyr or Val; Xaa94 is Ala, Arg, Asn, Asp, Cys, Glu, Gln, Gly, His, Ile, Leu, Lys, Met, Phe, Pro, Ser, Thr, Trp, Tyr or Val; Xaa95 is Ala, Arg, Asn, Asp, Cys, Glu, Gln, Gly, His, Ile, Leu, Lys, Met, Phe, Pro, Ser, Thr, Trp, Tyr or Val; Xaa96 is Arg, Gln, Glu,or Lys; Xaa97 is Arg, Asn, Asp, Gln, Glu, His, Lys, Ser or Thr; Xaa98 is Ile or Val; Xaa99 is Ala, Arg, Asn, Asp, Cys, Glu, Gln, Gly, His, Ile, Leu, Lys, Met, Phe, Pro, Ser, Thr, Trp, Tyr or Val; Xaa101 is Leu or Met; Xaa102 is Ile, Leu, Met or Val; Xaa103 is Ala, Arg, Asn, Asp, Cys, Glu, Gln, Gly, His, Ile, Leu, Lys, Met, Phe, Pro, Ser, Thr, Trp, Tyr or Val; Xaa104 is Gln or Glu; Xaa105 is Arg, Asn, Asp, Gln, Glu, His, Lys, Ser or Thr; Xaa107 is Ala or Gly; Xaa109 is Ala, Arg, Asn, Asp, Cys, Glu, Gln, Gly, His, Ile, Leu, Lys, Met, Phe, Pro, Ser, Thr, Trp, Tyr or Val.

II. Polypeptide Linker Considerations.

In the morphon constructs, polypeptide linker sequences join and maintain the spatial relationship of the finger and heel regions thereby helping to maintain the cysteine structural motif, i.e., the cysteine pattern and knot structure, which characterizes and is believed to be important in maintaining the tertiary structure of each subunit of a TGF-β superfamily member.

It is contemplated that the polypeptide linkers preferably are about 2–20, and most preferably about 3–13 amino acids in length. The polypeptide linkers should be long enough to permit the finger and heel regions to assume their proper conformation as defined as being able to bind a receptor that typically binds a TGF-β superfamily member. The specific amino acid composition of the polypeptide linker may vary, however, cysteine residues preferably should be avoided. Cysteine residues in the linker sequence may disulfide bond with the cysteine residues that define the knot structure thereby affecting the cysteine structural motif. It is contemplated that the amino acid sequence of each linker may be based either in whole or in part upon: 1) the amino acid sequences normally present at the ends of the template finger and heel regions; 2) unrelated amino acid sequences, predicted by computer based algorithms, to be sufficient to connect the ends of the finger and heel regions without affecting the spatial arrangement of the finger and heel regions in the morphon construct; 3) multiples or portions of pentomeric repeat units of $Gly_4Ser$ or $Ser_4Gly$; or 4) a combination thereof.

Accordingly, the artisan simply may choose an amino acid sequence, such as a β-turn, based upon the amino acid sequence that normally would connect the finger and heel regions within a template molecule. Alternatively, once the appropriate heel and finger regions have been chosen in accordance with the principles described above, the artisan may use a variety of commercially available computer-based algorithms to predict appropriate linker sequences capable of linking the finger and heel regions. Currently preferred, publicly available computer programs include, but are not limited to, CONGEN (Bruccoleri et al. (1987) *Biopolymers* 26:137) and TWEAK (Shenkin et al. (1987) *Biopolymers* 26:2053–2085), the disclosures of which are incorporated herein by reference. Currently preferred, commercially available software packages include, but are not limited to, INSIGHTII, HOMOLOGY, and DISCOVER, all of which are available from Biosym, Inc. Other computer-based programs useful in producing appropriate linker sequences are disclosed in U.S. Pat. Nos. 4,704,692; 4,881,175; 4,939,666; 4,946,778; and 5,260,203, the disclosures of which are incorporated herein by reference. The aforementioned programs and software packages enable the artisan to identify pre-existing amino acid sequences in protein structure databases or build using molecular simulation and/or thermodynamic calculations amino acid sequences for linking two polypeptide chains through designated N- and C-termini. In addition, as mentioned above, the artisan may simply link the ends of the appropriate finger and heel regions with an amino acid sequence based in whole, or in part, on the pentomeric repeat units of $Gly_4Ser$ or $Ser_4Gly$. Such repeats have been used successfully to construct single-chain antibody binding sites. Methodologies for designing, making, testing and using linkers based on the pentomeric repeats of $Gly_4Ser$ or $Ser_4Gly$ are disclosed in U.S. Pat. Nos. 5,132,405; 5,091,513; and 5,258,498 and PCT Application No. US88/01737, the disclosures of which are incorporated herein by reference.

It is contemplated that synthetic morphons may be joined through their N- or /C-termini via a polypeptide linker to a second functional protein domain to produce a multifunctional protein construct. For example, a morphon construct may be linked by means of an additional polypeptide linker to a single-chain antibody binding site for targeting, or to a chemokine, hormone, toxin, or other physiologically active functional protein. For details of the construction of these multifunctional proteins using such linkers, see U.S. Pat. Nos. 5,132,405 and 5,091,513.

III. Design and Production of Morphons.

As mentioned above, the biosynthetic constructs of the invention preferably are manufactured by using conventional recombinant DNA methodologies well known and thoroughly documented in the art.

For example, the constructs may be manufactured by the assembly of synthetic nucleotide sequences and/or joining DNA restriction fragments to produce a synthetic DNA molecule. The DNA molecules then are ligated into an expression vehicle, for example an expression plasmid, and transfected into an appropriate host cell, for example *E. coli*. The protein encoded by the DNA molecule then is expressed, purified, folded if necessary, tested in vitro for binding activity with a receptor having binding affinity for the template TGF-β superfamily member, and subsequently tested to assess whether the biosynthetic construct mimics the activity of the t emplate superfamily member.

Alternatively, a library of synthetic DNA constructs can be prepared sim ultaneously for example, by the assembly of synthetic nucleotide sequences that differ in nucleotide composition in a preselected region. For example, it is contemplated that during production of a morphon construct based upon a specific TGF-β superfamily member, the artisan may choose appropriate finger and heel regions for such a superfamily member (for example from FIGS. 5–9). Once the appropriate finger and heel regions have been selected, the artisan then may produce synthetic DNA encoding these regions, which subsequently may be connected by linker sequences encoding polypeptide linkers. For example, if a plurality of DNA molecules encoding different linker sequences are included into a ligation reaction containing DNA molecules encoding finger and heel sequences, by judicious choice of appropriate restriction sites and reaction conditions, the artisan may produce a library of DNA constructs wherein each of the DNA constructs encode finger and heel regions but connected by different linker sequences. The resulting DNAs then are ligated into a suitable expression vehicle, i.e., a plasmid useful in the preparation of a phage display library, transfected into a host cell, and the polypeptides encoded by the synthetic DNAs expressed to generate a pool of candidate compounds. The pool of candidate compounds subsequently can be screened to identify lead compounds having binding affinity and/or selectivity for a pre-selected receptor.

Screening may be performed by passing a solution comprising the candidate compounds through a chromatography column containing surface immobilized receptor. Then lead compounds with the desired binding specificity are eluted, for example by means of a salt gradient and/or a concentration gradient of the template TGF-β superfamily member. Nucleotide sequences encoding the lead compounds subsequently may be isolated and characterized. Once the appropriate nucleotide sequences of the lead compounds have been identified, the lead compounds subsequently may be produced, either by conventional recombinant DNA or peptide synthesis methodologies, in quantities sufficient to test whether the particular construct mimics the activity of the template TGF-β superfamily member.

It is contemplated that, which ever approach is adopted to produce DNA molecules encoding morphons of the invention, the tertiary structure of the lead compound or compounds may subsequently be modulated in order to optimize binding and/or biological activity by, for example, by a combination of nucleotide mutagenesis methodologies aided by the principles described herein and phage display methodologies. Accordingly, an artisan may produce and test simultaneously large numbers of candidate compounds. The refined compounds produced by this approach subsequently may be screened for either agonist or antagonist activity by using conventional in vitro and/or in vivo assays similar to the assays discussed hereinbelow.

A. Gene Synthesis.

The processes for manipulating, amplifying, and recombining DNA which encode amino acid sequences of interest generally are well known in the art, and therefore, are not described in detail herein. Methods of identifying and isolating genes encoding members of the TGF-β superfamily and their cognate receptors also are well understood, and are described in the patent and other literature.

Briefly, the construction of DNAs encoding the biosynthetic constructs disclosed herein is performed using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, polymerase chain reaction (PCR) techniques for amplifying appropriate nucleic acid sequences from libraries, and synthetic probes for isolating genes of members of the TGF-b superfamily and their cognate receptors. Various promoter sequences from bacteria, mammals, or insects to name a few, and other regulatory DNA sequences used in achieving expression, and various types of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector.

One method for obtaining DNA encoding the biosynthetic constructs disclosed herein is by assembly of synthetic oligonucleotides produced in a conventional, automated, oligonucleotide synthesizer followed by ligation with appropriate ligases. For example, overlapping, complementary DNA fragments may be synthesized using phosphoramidite chemistry, with end segments left unphosphorylated to prevent polymerization during ligation. One end of the synthetic DNA is left with a "sticky end" corresponding to the site of action of a particular restriction endonuclease, and the other end is left with an end corresponding to the site of action of another restriction endonuclease. The complimentary DNA fragments are ligated together to produce a synthetic DNA construct.

Alternatively nucleic acid strands encoding finger 1, finger 2 and heel regions may be isolated from libraries of nucleic acids, for example, by colony hybridization procedures such as those described in Sambrook et al. eds. (1989) "Molecular Cloning", Coldspring Harbor Laboratories Press, NY, and/or by PCR amplification methodologies, such as those disclosed in Innis et al. (1990) "PCR Protocols, A guide to methods and applications", Academic Press. The nucleic acids encoding the finger and heel regions then are joined together to produce a synthetic DNA encoding the biosynthetic single-chain morphon construct of interest.

It is appreciated, however, that a library of DNA constructs encoding a plurality of morphons may be produced simultaneously by standard recombinant DNA methodologies, such as the ones, described above, For example, the skilled artisan by the use of cassette mutagenesis or oligonucleotide directed mutagenesis may produce, for example, a series of DNA constructs each of which contain different DNA sequences within a predefined location, e.g., within a DNA cassette encoding a linker sequence. The resulting library of DNA constructs subsequently may be expressed, for example, in a phage display library (see section V below) and any protein constructs that binds to a specific receptor may be isolated by affinity purification, e.g., using a chromatographic column comprising surface immobilized receptor (see section V below). Once molecules that bind the preselected receptor have been isolated, their binding and agonist properties may be modulated using the empirical refinement techniques also discussed in section V, below.

B. Protein Expression

If a single DNA construct of interest has been synthesized, it may be integrated into an expression vector and transfected into an appropriate host cell for protein expression. Useful prokaryotic host cells include, but are not limited to, *E. coli*, and *B. Subtilis*. Useful eukaryotic host cells include, but are not limited to, yeast cells, insect cells, myeloma cells, fibroblast 3T3 cells, monkey kidney or COS cells, chinese hamster ovary (CHO) cells, mink-lung epithelial cells, human foreskin fibroblast cells, human glioblastoma cells, and teratocarcinoma cells. Alternatively, the synthetic genes may be expressed in a cell-free system such as the rabbit reticulocyte lysate system.

The vector additionally may include various sequences to promote correct expression of the recombinant protein, including transcriptional promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest also may be manipulated to remove potentially inhibiting sequences or to minimize unwanted secondary structure formation. The morphon proteins also may be expressed as fusion proteins. After being translated, the protein may be purified from the cells themselves or recovered from the culture medium and then cleaved at a specific protease site if so desired.

For example, if the gene is to be expressed in *E. coli*, it is cloned into an appropriate expression vector. This can be accomplished by positioning the engineered gene downstream of a promoter sequence such as Trp or Tac, and/or a gene coding for a leader peptide such as fragment B of protein A (FB). During expression, the resulting fusion proteins accumulate in refractile bodies in the cytoplasm of the cells, and may be harvested after disruption of the cells by French press or sonication. The isolated refractile bodies then are solubilized, and the expressed proteins folded and the leader sequence cleaved, if necessary, by methods already established with many other recombinant proteins.

Expression of the engineered genes in eukaryotic cells requires cells and cell lines that are easy to transfect, are capable of stably maintaining foreign DNA with an unrearranged sequence, and which have the necessary cellular components for efficient transcription, translation, post-translation modification, and secretion of the protein. In addition, a suitable vector carrying the gene of interest also is necessary. DNA vector design for transfection into mammalian cells should include appropriate sequences to promote expression of the gene of interest as described herein, including appropriate transcription initiation, termination, and enhancer sequences, as well as sequences that enhance translation efficiency, such as the Kozak consensus sequence. Preferred DNA vectors also include a marker gene and means for amplifying the copy number of the gene of interest. A detailed review of the state of the art of the production of foreign proteins in mammalian cells, including useful cells, protein expression-promoting sequences, marker genes, and gene amplification methods, is disclosed in Bendig (1988) *Genetic Engineering* 7:91–127.

The best characterized transcription promoters useful for expressing a foreign gene in a particular mammalian cell are the SV40 early promoter, the adenovirus promoter (AdMLP), the mouse metallothionein-I promoter (mMT-I), the Rous sarcoma virus (RSV) long terminal repeat (LTR), the mouse mammary tumor virus long terminal repeat (MMTV-LTR), and the human cytomegalovirus major intermediate-early promoter (hCMV). The DNA sequences for all of these promoters are known in the art and are available commercially.

The use of a selectable DHFR gene in a dhfr-cell line is a well characterized method useful in the amplification of genes in mammalian cell systems. Briefly, the DHFR gene is provided on the vector carrying the gene of interest, and addition of increasing concentrations of the cytotoxic drug methotrexate, which is metabolized by DHFR, leads to amplification of the DHFR gene copy number, as well as that of the associated gene of interest. DHFR as a selectable, amplifiable marker gene in transfected chinese hamster ovary cell lines (CHO cells) is particularly well characterized in the art. Other useful amplifiable marker genes include the adenosine deaminase (ADA) and glutamine synthetase (GS) genes.

The choice of cells/cell lines is also important and depends on the needs of the experimenter. COS cells provide high levels of transient gene expression, providing a useful means for rapidly screening the biosynthetic constructs of the invention. COS cells typically are transfected with a simian virus 40 (SV40) vector carrying the gene of interest. The transfected COS cells eventually die, thus preventing the long term production of the desired protein product. However, transient expression does not require the time consuming process required for the development of a stable cell line, and thus provides a useful technique for testing preliminary constructs for binding activity.

The various cells, cell lines and DNA sequences that can be used for mammalian cell expression of the single-chain constructs of the invention are well characterized in the art and are readily available. Other promoters, selectable markers, gene amplification methods and cells also may be used to express the proteins of this invention. Particular details of the transfection, expression, and purification of recombinant proteins are well documented in the art and are understood by those having ordinary skill in the art. Further details on the various technical aspects of each of the steps used in recombinant production of foreign genes in mammalian cell expression systems can be found in a number of texts and laboratory manuals in the art, such as, for example, F. M. Ausubel et al., ed., *Current Protocols in Molecular Biology*, John Wiley & Sons, New York, (1989).

IV. Screening Binding and Biological Activity.

Depending upon the cell type used, the DNA encoding the morphon constructs may be expressed to produce morphons having either folded or unfolded conformations. For example, it is appreciated that the morphon may spontaneously fold into an active conformation during production in a host cell, such as a myeloma cell. However, during expression in prokaryotic organisms, such as *E. coli*, the protein may form unfolded protein aggregates called inclusion bodies. The inclusion bodies, once harvested are subjected in vitro to standard denaturing and renaturing conditions to produce a biologically active protein conformation.

Irrespective of which protein expression, harvesting, and, if necessary folding, methodologies are used, the resulting proteins that bind preferentially to a preselected receptor subsequently may be identified using standard methodologies, i.e., ligand/receptor binding assays, well known, and thoroughly documented in the art. See for example: Legerski et al. (1992) *Biochem. Biophys. Res. Comm.* 183: 672–679; Frakar et al. (1978) *Biochem. Biophys. Res. Comm* 80:849–857; Chio et al. (1990) Nature 343: 266–269; Dahlman et al. (1988) *Biochem* 27: 1813–1817; Strader et al. (1989) *J. Biol. Chem.* 264: 13572–13578; and D'Dowd et al. (1988) *J. Biol. Chem.* 263:15985–15992.

Typically, in a ligand/receptor binding assay, the template TGF-β superfamily member of interest having a known, quantifiable affinity for a preselected receptor is labeled with a detectable moiety, for example, a radiolabel, a chromogenic label, or a fluorogenic label. Aliquots of purified receptor, receptor binding domain fragments, or cells expressing the receptor of interest on their surface are incubated with the labeled TGF-β superfamily member in the presence of various concentrations of the unlabeled morphon. The relative binding affinity of a candidate morphon may be measured by quantitating the ability of the candidate (unlabeled morphon) to inhibit the binding of the labeled template TGF-β superfamily member with the receptor. In performing the assay, fixed concentrations of the receptor and the TGF-β superfamily member are incubated in the presence and absence of unlabeled morphon. Sensitivity may be increased by pre-incubating the receptor with the candidate morphon before adding the labeled template TGF-β superfamily member. After the labeled competitor has been added, sufficient time is allowed for adequate competitor binding, and then free and bound labeled superfamily members are separated from one another, and one or the other measured.

Useful labels useful in the practice of the screening procedures include radioactive labels, i.e., $^{125}$I, $^{131}$I, $^{111}$In or $^{77}$Br, chromogenic labels, spectroscopic labels such as those disclosed in Haughland (1994) "*Handbook of Fluorescent and Research Chemicals* 5 ed." by Molecular Probes, Inc., Eugene, OR, or conjugated enzymes having high turnover rates, i.e., horseradish peroxidase, alkaline phosphatase, or β-galactosidase, used in combination with chemiluminescent or fluorogenic substrates.

The biological activity, namely the agonist or antagonist properties of the resulting constructs may subsequently be characterized using conventional in vivo and in vitro assays that have been developed to measure the biological activity of any TGF-β superfamily member. It is appreciated, however, the type of assay used will depend on the TGF-β superfamily member upon which the morphon is based. For example, morphon constructs based upon natural OP-1 protein may be assayed using any of the biological assays that have been developed to date for measuring OP-1 activity, see, for example, the exemplification's set forth below.

V. Enhancement of Binding Activity.

Once lead compounds have been identified i.e., those having at least basal binding affinity for a receptor that normally binds the template TGF-β superfamily member, their affinities may be enhanced by a combination of computer-based protein structure modeling and rational drug design methodologies. For example, after computer modeling of the candidate morphon construct, solvent exposed surfaces of the finger and heel regions or alternatively linker sequences may be mutated to enhance or modulate binding activity and/or specificity.

During such an approach, it is appreciated that several structural elements may independently be mutated in separate constructs. After isolating morphons having the highest binding and/or biological activity, each of the elements giving rise to enhanced activity may be isolated, characterized and then combined in a single construct. This type of approach has been used successfully in the production of a human growth hormone analog that has an affinity for hormone receptor 400-fold greater than the wild type human growth hormone (Wells et al., in "*Advances in Gene Technology: Protein Engineering and Beyond*" p105). Alternatively, a plurality of regions within the protein may be modified simultaneously in a single experiment and constructs having the highest binding affinity and/or specificity isolated. It is appreciated, however, that several rounds of mutagenesis and screening may be performed until a construct having the desired binding affinity is found.

An important aspect of the refinement process is that when recombinant DNA methodologies are used it is necessary to establish and maintain a physical connection between the polypeptide of interest and the nucleic acid encoding it. A system useful in the practice of this aspect of the invention includes, for example, phage display methodologies wherein the peptide of interest is immobilized on the surface of the phage as a fusion with a phage coat protein, see for example, Scott et al. (1990) *Science* 249: 386–390; Parmely et al., (1988) *Gene* 73: 305–318; Devlin et al., (1990) *Science* 249: 404–406; McCafferty et al. (1990) *Nature* 348: 552–554; Marks et al. (1992) *J. Biol. Chem.* 267:16007–16010; Lowman et al. (1991) *Biochem.* 30:10832–10838; Wells et al. supra; Amberg et al. in *Strategies in Molecular Biology* 6:2–4; and the Recombinant Phage Antibody System instruction manual from Pharmacia, P-L Biochemicals.

Briefly, the DNAs encoding candidate morphon constructs are expressed on the surface of phage particles, typically as N-terminal fusions to a phage minor coat protein. In a typical refinement experiment, it is contemplated that nucleotides encoding specific portions of the synthetic gene, e.g., those encoding linker sequences, may be randomized so as to produce a library of nucleic acid sequences encoding constructs that have random amino acid sequences in that region (See Section 3A). Once a library of DNA molecules encoding morphons has been produced, the DNAs are ligated into the phage genome at a position adjacent to the gene encoding a minor coat protein. The resulting DNAs are packaged, amplified in a host cell, and expressed to produce recombinant phage particles having on their cell surface minor coat proteins fused to the protein of interest. The recombinant phage particles that express morphons constructs having the desired binding affinity and/or specificity for a receptor of interest subsequently are isolated by several rounds of affinity enrichment followed by phage growth. By using these approaches, single phage particles expressing polypeptides having specific biological properties may be isolated routinely from phage libraries comprising more than $10^6 14$ $10^8$ phage particles.

Affinity enrichment may, for example, be performed by passing a solution comprising recombinant phage particles through a chromatography column that comprises surface immobilized receptor under conditions which permit morphons expressed on the surface of recombinant phage particles to bind to the receptor. Then, the column is washed to remove residual and/or non-specifically bound phage, and phage expressing the conformationally active morphons eluted by specific desorption, for example, by addition of excess of the template TGF-β superfamily member, or by non-specific desorption, for example, using pH, polarity-reducing agents or chaotropic salts. The highest binding particles may be eluted using concentration gradient of the desorption inducing reagent wherein the highest binding particles elute at higher concentrations of the reagent. The highest binding particles, once eluted are re-amplified, and the nucleic acid encoding the morphon of interest isolated and sequenced. Once the DNA sequence, and therefore the nucleic acid sequence of the highest binding morphons, has been determined, then the refinement process may be repeated, for example, by mutagenesis of another portion of the molecule, until morphon molecules having a preferred binding activity have been produced. The resulting constructs subsequently may be assayed for biological activity using in vivo or in vitro assays that have been developed for each of the template TGF-β superfamily members identified to date.

Following the identification of useful morphon constructs, the morphons may be produced in commercially useful quantities, for example, by producing cell lines that express the morphon of interest or by producing synthetic peptides defining the appropriate amino acid sequence. It is appreciated, however, that conventional methodologies for producing the appropriate cell lines and for producing synthetic peptides are well known and thoroughly documented in the art, and so are not discussed in detail herein.

VI. Formulation and Bioactivity

The resulting morphon constructs may be provided to an individual as part of a therapy to enhance, inhibit, or otherwise modulate the in vivo binding interaction between a TGF-β superfamily member and one or more of its cognate receptors. The constructs may be formulated in a pharmaceutical composition, as described below, and may be administered by any suitable means, preferably directly or systematically, e.g., parentally or orally.

Where the morphon construct is to be provided directly (e.g., locally, as by injection, to a desired tissue site), or parentally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the therapeutic composition preferably comprises part of an aqueous solution. The solution preferably is physiologically acceptable so that in addition to delivery of the desired construct to the patient, the solution does not otherwise adversely affect the patient's electrolyte and volume balance. The aqueous medium for the therapeutic molecule thus may comprise, for example, normal physiological saline (0.9% NaCl, 0.15M), pH 7–7.4 or other pharmaceutically acceptable salts thereof.

Useful solutions for oral or parenteral administration may be prepared by any of the methods well known in the pharmaceutical art, described, for example, in *"Remington's Pharmaceutical Sciences"*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the morphogen in vivo.

Other potentially useful parenteral delivery systems for these therapeutic molecules include ethylene-vinyl acetate copolymer particles, osmotic pumps, implantable infusion systems, and liposomes. Formulations for inhalation administration may contain as excipients, for example, lactose, or may be aqueous solutions containing, for example, polyoxyethylene-9-lauryl ether, glycocholate and deoxycholate, or oily solutions for admninistration in the form of nasal drops, or as a gel to be applied intransally.

Finally, therapeutic molecules may be administered alone or in combination with other molecules known to effect tissue morphogenesis, i.e., molecules capable of tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration may include nerve growth factors. Other useful cofactors include symptom-alleviating cofactors, including antiseptics, antibiotics, antiviral and antifungal agents and analgesics and anesthetics.

Therapeutic molecules further can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition may include the biosynthetic construct dispersed in a fibrinogen-thrombin composition or other bioadhesive such as is disclosed, for example in PCT US91/09275, the disclosure of which is incorporated herein by reference. The composition then may be painted, sprayed or otherwise applied to the desired tissue surface.

The compositions can be formulated for parenteral or oral administration to humans or other mammals in therapeutically effective amounts, e.g., amounts which provide appropriate concentrations of the morphon to target tissue for a time sufficient to induce the desired effect.

Where the therapeutic molecule comprises part of a tissue or organ preservation solution, any commercially available preservation solution may be used to advantage. For example, useful solutions known in the art include Collins solution, Wisconsin solution, Belzer solution, Eurocollins solution and lactated Ringer's solution. A detailed description of preservation solutions and useful components may be found, for example, in U.S. Pat. No. 5,002,965, the disclosure of which is incorporated herein by reference.

It is contemplated also that some of the morphon constructs, for example morphons based upon members of the Vg/dpp subgroup, may exhibit the highest levels of activity in vivo when combined with carrier matrices i.e., insoluble polymer matrices. See for example, U.S. Pat. No. 5,266,683 the disclosure of which is incorporated by reference herein. The currently preferred carrier matrices are xenogenic, allogenic or autogenic in nature. It is contemplated, however, that synthetic materials comprising polylactic acid, polyglycolic acid, polybutyric acid, derivatives and copolymers thereof may also be used to generate suitable carrier matrices. Preferred synthetic and naturally derived matrix materials, their preparation, methods for formulating them with the morphogenic proteins of the invention, and methods of administration are well known in the art and so are not discussed in detailed herein. See for example, U.S. Pat. No. 5,266,683.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of a disease, tissue loss or defect, the overall health status of the particular patient, the relative biological efficacy of the compound selected, the formulation of the compound, the presence and types of excipients in the formulation, and the route of administration. In general terms, the therapeutic molecules of this invention may be provided to and individual where typical doses range from about 10 ng/kg to about 1 g/kg of body weight per day; with a preferred dose range being from about 0.1 mg/kg to 100 mg/kg of body weight.

Practice of the invention will be more fully understood from the following examples which are for illustrative purposes only and, therefore, should not be construed as limiting the invention in any way.

EXAMPLE I.

Design and Production of Morphon Based Upon the TGF-β Superfamily Member OP-1.

An exemplary OP-1 based morphon designed in accordance with the principles described herein and having a DNA sequence defined in the Sequence Listing as SEQ. ID. NO.: 29 and which encodes a protein sequence defined in the Sequence Listing as SEQ. ID. NO. 30 (and as shown in FIGS. 11A–E) may be produced using standard recombinant DNA methodologies, such as those described hereinabove. The DNA sequence encoding the exemplary OP-1 morphon, SEQ. ID. NO.: 29, comprises a plurality of restriction sites which, should the need arise, simplifies subsequent steps, i.e., cassette mutagenesis, in the empirical refinement of the morphon structure.

The OP-1 morphon protein sequence set forth in SEQ. ID. NO. 30 comprises from the N-teminus to the C-terminus, an OP-1 finger 1 sequence (amino acid residues 1–32 in SEQ. ID. NO. 30); a large linker sequence (amino acid residues 33–44 in SEQ. ID. NO. 30); an OP-1 heel sequence (amino acid residues 45–75 in SEQ. ID. NO. 30); a small linker sequence (amino acid residues 76–79 in SEQ. ID. NO. 30) and an OP-1 finger 2 sequence (amino acid residues 80–115 in SEQ. ID. NO. 30).

The DNA sequence encoding the OP-1 morphon (SEQ. ID. NO. 30) is defined in SEQ. ID. NO. 30 and may be produced by standard recombinant DNA methodologies, for example, synthesis of synthetic DNA sequences followed by their ligation into an appropriate expression vector. It is contemplated, however, that in order to enhance the likelihood of producing an OP-1 morphon construct having binding and/or agonist properties, the following method may be used.

Briefly, this method comprises the steps of inserting into a cDNA clone encoding human OP-1, an N-terminal linker, a C-terminal linker, a large loop connecting the finger 1 and heel regions, and a small loop connecting the heel and finger 2 regions. The modified cDNA subsequently is excised from its vector and ligated into a phage display vector, e.g. pCANTAB 5 from Pharmacia, and then, in a series of independent mutagenesis steps, in combination with screening in the phage display system, the linker regions are mutated by oligonucleotide directed mutagenesis to produce a pool of candidate morphon constructs. Phage which express on their virion surface morphon constructs that bind the OP-1 receptor are isolated and the gene encoding the morphon constructs sequenced. A final construct comprising finger and heel regions as well as linker regions identified from the highest binding individual constructs then are combined to produce an optimized OP-1 morphon construct. A C-terminal tail is introduced into the optimized morphon construct by oligonucleotide directed mutagenesis after which the resulting morphon construct is excised from its vector and inserted into an E. coli expression vector, e.g. pET from New England BioLabs, Beverly, Mass. A detailed description of this method is set forth below.

A SmaI to BamHI fragment of the OP-1 cDNA defined in SEQ. ID. NO. 29 (Ozkaynak et al. (1990) EMBO J. 9: 2085–2093) is cloned into Bluescript KS+(available from Stratagene Cloning Systems, La Jolla, Calif.) previously cleaved with EcoRV and BamHI. Once Transformed into E. coli, the resulting colonies are screened by a blue-white selection process wherein the desired colonies are blue. The correct clone may be identified by restriction screening to give the following expected restriction fragments.

| Restriction Enzyme | Fragment size (bp) |
| --- | --- |
| EcoR I | 84, 789, 3425 |
| Xho I | 161, 1223, 2914 |
| Sac II | 97, 650, 3551 |

Using synthetic oligonucleotides and either PCR or the site-directed mutagenesis methods, see for example, Kunkel, (1985) Proc. Natl. Acad. Sci. USA 822: 488; Kunkel et al. (1985) Meth. Enzymol. 154: 367; and U.S. Pat. No. 4,873,192, specific nucleotides are modified within the OP-1 cDNA to introduce large and small loops within the OP-1 gene and to introduce unique restriction sites at the ends of the OP-1 gene. With all of the following modifications, there is no frame shift and, therefore, E. coli transformed with the mutagenesis products that give white colonies indicate an error in the sequence.

In a first step, the large loop is introduced by oligonucleotide directed mutagenesis using the oligonucleotide set forth in SEQ. ID. NO. 34. The oligonucleotide for the large loop is designed so it that has N-terminal and C-terminal over lapping ends 15 bp long, and introduces a unique Bam HI restriction site which can be used to screen for incorporation.

Then, the small loop is introduced by oligonucleotide directed mutagenesis using the oligonucleotide set forth in SEQ. ID. NO. 33. The oligonucleotide for the small loop is designed so it that has N-terminal and C-terminal overlapping ends 18 bp long, and introduces a unique NheI restriction site which can be used to screen for incorporation.

Then, the C-terminus of the OP-1 gene is modified by oligonucleotide directed mutagenesis using the oligonucleotide set forth in SEQ. ID. NO. 35. The C-terminus is modified to remove the native stop codon and introduce a NotI site for cloning into a vector useful for producing a phage display library, specifically pCANTAB 5 phagemid from Pharmacia. The oligonucleotide designed for this purpose has N-terminal and C-terminal over lapping ends 14 bp long, and introduces both a unique NotI restriction site and a unique SphI restriction site. Both restriction sites can be used to screen for incorporation.

Then, the N-terminus of the OP-1 gene is modified by oligonucleotide directed mutagenesis using the oligonucleotide set forth in SEQ. ID. NO. 32. The N-terminus is modified to introduce a SfiI restriction site for cloning into the pCANTAB 5 phagemid and an NdeI restriction site for eventual cloning into an expression vector. The oligonucleotide designed for this purpose has N-terminal and C-terminal overlapping ends 22 bp long. Both the SfiI and the NdeI restriction sites can be used to screen for incorporation.

The OP-1 cDNA resulting from the previous four mutagenesis steps is set forth in SEQ. ID. NO. 37. In order to improve the efficiency of selecting OP-1 morphon constructs that bind an OP-1 receptor, mutagenesis of the large and small loops are performed in independent reactions. To enable this step, the resulting cDNA (SEQ. ID. NO. 37) is digested with the restriction enzymes SfiI and NotI, and the 376 bp SfiI to NotI fragment is cloned directly into the pCANTAB 5 phagemid previously digested with the restriction enzymes SfiI and NotI.

Mutations may be introduced into the small loop by oligonucleotide directed mutagenesis using oligonucleotides similar to those defined in SEQ. ID. Nos. 38 and 39. Mutations also may be introduced into the large loop by oligonucleotide directed mutagenesis using oligonucleotides similar to those set forth in SEQ. ID. Nos. 40, 41, 42, and 43. Oligonucleotides defined by SEQ. ID. Nos. 40 and 41 introduce changes in the first 20 base pairs defining the large loop while oligonucleotides defined by SEQ. ID. Nos. 42 and 43 introduce changes into the last half of the loop.

Libraries of phage expressing on their virion surfaces proteins produced by each of the separate loop mutagenesis steps are screened for binding activity with OP-1 receptor using a protocol set forth in the instructions for use with the "Recombinant Phage Antibody System" (Pharmacia). Briefly, the library of clones in pCANTAB 5 phagemid produced by each of the separate loop mutagenesis steps are transformed into competent E.coli TG1 and grown in the presence of KO7 helper phage. This step results in the production of phage expressing OP-1 morphons on their cell surface. The resulting phage are screened for binding activity with OP-1 receptor (Malpe et al. (1994) Biochem. Biophys. Res. Comm. 201: 1140–1147; tenDijke et al. (1994) J. Biol. Chem. 269:16985–16988) previously immobilized on a solid surface, e.g., Affigel 15, Fractrogel, plastic surface or a magnetic bead (Hermanson et al. in "Immobilized Affinity Ligand Techniques" (1992) Academic Press, Inc, San Diego). Phage that fail to bind the receptor are removed by washing exhaustively (more than 20 washes) with a buffer containing phosphate buffered saline (PBS), followed by exhaustive washes (more than 20 washes) with PBS containing 0.05% Triton X-100. Then, specific binding constructs are eluted from the solid surface with a buffer containing 0.1 M glycine, pH 3.0, and 0.05% Triton X-100 and the eluate neutralized with 1M Tris-HCl pH8.0, 0.05% Triton X-100. Phage having specific affinity for OP-1 are harvested. At this stage, however, the eluate may contain several different phage where each phage particle can bind OP-1 receptor.

In order to isolate individual phage particles, E. coli then are reinfected with the eluted phage, and infected colonies are titrated out to give individual colonies into microtiter plates. Then, the infected E. coli are harvested from each well of the microtiter plate, infected with KO7 helper phage to reinduce the expression of the OP-1 morphon on the surface of the resulting phage, and the resulting mixture is added to individual well s of a second microliter dish containing surface immobilized OP-1 receptor. Using this approach, individual phage can be screened for binding activity with immobilized OP-1 receptor. Binding is visualized with an horse radish peroxidase conjugated antibody having binding specificity for an antigen on the surface of the phage. The individual phage subsequently are eluted from the OP-1 receptor bound to the surface of a well on the microtiter dish and the DNA isolated from them. After sequencing, the DNA sequences encoding particular regions, for example, the small and large loops, that generate the high binding affinity are combined in a single morphon construct.

Then, a linker is introduced into the C-terminus of the penultimate morphon gene by oligonucleotide directed mutagenesis using the oligonucleotide set forth in SEQ. ID. NO.36. The linker introduces the non-suppressible stop codon TAA at the end of the morphon gene "... RACGSH*" (SEQ. ID. NO. 45) and follows the stop codon with a unique BglII site (AGATCT). Success in making this change is determined by the absence of exported phage (the termination codon blocks the production of gene 3 protein) and the ability to cleave plasmid DNA with BglII. Then, the optimized OP-1 morphon gene is excised with NdeI and BglII and cloned into a pET vector (New England Biolabs, Beverly, Mass.) previously cleaved with NdeI and BamHI.

Expression of the morphon gene to produce the morphon gene product is induced after the expression of T7 RNA polymerase (initiated through infected with λCE6 phage). During expression, the OP-1 morphon is produced in inclusion granules which are harvested from the cell paste. The protein then is dissolved in 6M guanidine-HCl, 0.2 M Tris-HCl, pH 8.2, and 0.1 M 2-mercaptoethanol and dialyzed exhaustively against 6M urea, 2.5 mM Tris-HCl, pH 7.5 and 1 mM EDTA. 2-mercaptoethanol is added to a final concentration of 0.1 M and the solution incubated at room temperature. Then, the mixture is dialyzed exhaustively against buffer containing 2.5 mM Tris-HCl, pH 7.5 and 1 mM EDTA. Folded OP-1 morphon then is purified by affinity chromatography on a column packed with surface immobilized OP-1 receptor. Unbound material is removed by washing as described above and the specific OP-1 receptor binding material is eluted also as described above.

EXAMPLE II.
Determination of Binding Activity of an OP-1 Based Morphon.

Cells expressing an OP-1 receptor on their cell surface are plated into 35 mm dishes and incubated for 48 hours in DMEM (Dulbecco's modified Eagle medium) plus 10% fetal calf serum. Purified OP-1, or an OP-1-analog is iodinated with $Na^{125}I$ by chloramine T oxidation, preferably having a specific activity of about 50–100 mCi/mg, by following essentially the protocol of Frolik et al. (1984) J. Biol. Chem. 595:10995–11000. Labeled OP-1, or OP-1-analog, then is purified using a standard procedure, e.g., by chromatographic separation. The plated cells then are washed twice with physiologically buffered saline in the presence of 0.1% BSA, and incubated at 22° C. in the presence of BSA, buffer and labeled OP-1 (1 ng) and various concentrations (e.g., 0–10 mg/ml) of unlabelled competitor, e.g., unlabelled OP-1 or the candidate OP-1 based morphon. Following binding, the cells are washed three times with cold buffer, solubilized in 0.5 ml of 0.5 N NaOH, removed from the dish, and radioactivity determined by gamma or scintillation counter. Data then are expressed as percent inhibition, where 100% inhibition of specific binding is the difference between binding in the absence of competitor and binding in the presence of a 100-fold molar excess of unlabelled competitor. Binding parameters preferably are determined using a computer program such as LIGAND (Munsun et al. (1980) Anal. Biochem. 107: 220–259). Upon performance of the assay, it is contemplated that the OP-1 based morphon may have specific binding activity for the OP-1 receptor. Upon confirmation of binding activity, the morphon may be tested subsequently for biological activity.

EXAMPLE III.
Determination of Biological Activity of an OP-1 Based Morphon.

The biological activity of the resulting OP-1 based morphons may be determined using any of the using standard in vivo and in vitro assays, typically used for assessing native OP-1 activity. A variety of exemplary assays are set forth below.

A. Mitogenic Effect on Rat and Human Osteoblasts

The following example is designed to demonstrate the ability of OP-1 morphons to induce proliferation of osteoblasts in vitro. It is contemplated that in this, and all the other examples involving osteoblast cultures, rat osteoblast-enriched primary cultures preferably are used. Although these cultures are heterogeneous in that the individual cells are at different stages of differentiation, the culture is believed to more accurately reflect the metabolism and function of osteoblasts in vivo than osteoblast cultures obtained from established cell lines. Unless otherwise indicated, all chemicals referenced are standard, commercially available reagents, readily available from a number of sources, including Sigma Chemical, Co., St. Louis; Calbiochem, Corp., San Diego and Aldrich Chemical Co., Milwaukee.

Briefly, rat osteoblast-enriched primary cultures are prepared by sequential collagenase digestion of newborn rat calvaria (e.g., from 1–2 day-old animals, Long-Evans strain, Charles River Laboratories, Wilmington, Mass.), following standard procedures, such as are described, for example, in Wong et al., (1975) Proc. Natl. Acad. Sci. USA 72: 3167–3171. Rat osteoblast single cell suspensions then are plated onto a multi-well plate (e.g., a 24 well plate at a concentration of 50,000 osteoblasts per well) in alpha MEM (modified Eagle's medium, Gibco, Inc., Long Island) containing 10% FBS (fetal bovine serum), L-glutamine and penicillin/streptomycin. The cells are incubated for 24 hours at 37° C., at which time the growth medium is replaced with alpha MEM containing 1% FBS and the cells incubated for an additional 24 hours so that cells are in serum-deprived growth medium at the time of the experiment.

The cultured cells are divided into four groups: (1) wells which receive, for example, 0.1, 1.0, 10.0, 40.0 and 80.0 ng of OP-1 morphon, (2) wells which receive 0.1, 1.0, 10.0 and 40.0 ng of wild type OP-1; (3) wells which receive 0.1, 1.0, 10.0, and 40.0 ng of TGF-β, and (4) the control group, which receive no growth factors. The cells then are incubated for an additional 18 hours after which the wells are pulsed with 2 mCi/well of $^3$H-thymidine and incubated for six more hours. The excess label then is washed off with a cold solution of 0.15 M NaCl and then 250 ml of 10% tricholoracetic acid is added to each well and the wells incubated at room temperature for 30 minutes. The cells then are washed three times with cold distilled water, and lysed by the addition of 250 ml of 1% sodium dodecyl sulfate (SDS) for a period of 30 minutes at 37° C. The resulting cell lysates are harvested using standard means and the incorporation of $^3$H-thymidine into cellular DNA determined by liquid scintillation as an indication of mitogenic activity of the cells. In the experiment, it is contemplated that the OP-1 morphon construct like natural OP-1 will stimulate $^3$H-thymidine incorporation into DNA, and therefore promote osteoblast cell proliferation. In contrast, the effect of the TGF-β is expected to be transient and biphasic. Furthermore, it is contemplated that at higher concentrations, TGF-β will have no significant effect on osteoblast cell proliferation.

The in vitro effect of the OP-1 morphon on osteoblast proliferation also may be evaluated using human primary osteoblasts (obtained from bone tissue of a normal adult patient and prepared as described above) and on human osteosarcoma-derived cell lines.

B. Progenitor Cell Stimulation.

The following example is designed to demonstrate the ability of OP-1 morphons to stimulate the proliferation of mesenchymal progenitor cells. Useful naive stem cells include pluripotential stem cells, which may be isolated from bone marrow or umbilical cord blood using conventional methodologies, (see, for example, Faradji et al. (1988) *Vox Sang*. 55 (3): 133–138 or Broxmeyer et al. (1 989) *Proc. Natl. Acad. Sci. USA*. 86: 3828–3832), as well as naive stem cells obtained from blood. Alternatively, embryonic cells (e.g., from a cultured mesodermal cell line) may be used.

Another method for obtaining progenitor cells and for determining the ability of OP-1 morphons to stimulate cell proliferation is to capture progenitor cells from an in vivo source. For example, a biocompatible matrix material able to allow the influx of migratory progenitor cells may be implanted at an in vivo site long enough to allow the influx of migratory progenitor cells. For example, a bone-derived, guanidine-extracted matrix, formulated as disclosed for example in Sampath et al. (1983) *Proc. Natl. Acad. Sci. USA* 80: 6591–6595, or U.S. Pat. No. 4,975,526, may be implanted into a rat at a subcutaneous site, essentially following the method of Sampath et al. After three days the implant is removed, and the progenitor cells associated with the matrix dispersed and cultured.

Progenitor cells, however obtained, then are incubated in vitro with the candidate OP-1 morphon under standard cell culture conditions, such as those described hereinbelow. In the absence of external stimuli, the progenitor cells do not, or only minimally, proliferate on their own in culture. It is contemplated, however, that progenitor cells cultured in the presence of a biologically active OP-1 morphon, like OP-1, will proliferate. Cell growth can be determined visually or spectrophotometrically using standard methods well known in the art.

C. Morphogen-Induced Cell Differentiation.

A variety of assays may be used to determine OP-1 based morphon-induced cellular differentiation.

(1) Embryonic Mesenchyme Differentiation

As with natural OP-1, it is contemplated that OP-1 morphons may be utilized to induce cell differentiation. The ability of OP-1 morphons to induce cell differentiation may be demonstrated by culturing early mesenchymal cells in the presence of OP-1 morphon and then studying the histology of the cultured cells by staining with toluidine blue using standard cell culturing and cell staining methodologies well described in the art. For example, it is known that rat mesenchymal cells destined to become mandibular bone, when separated from the overlying epithelial cells at stage 11 and cultured in vitro under standard tissue culture conditions, e.g., in a chemically defined, serum-free medium, containing for example, 67% DMEM (Dulbecco's modified Eagle's medium), 22% F-12 medium, 10 mM Hepes pH 7, 2mM glutamine, 50 mg/ml transferrin, 25 mg/ml insulin, trace elements, 2mg/ml bovine serum albumin coupled to oleic acid, with HAT (0.1 mM hypoxanthine, 10 mM aminopterin, 12 mM thymidine, will not continue to differentiate. However, if these same cells are left in contact with the overlying endoderm for an additional day, at which time they become stage 12 cells, they will continue to differentiate on their own in vitro to form chondrocytes. Further differentiation into osteoblasts and, ultimately, mandibular bone, requires an appropriate local environment, e.g., a vascularized environment.

It is anticipated that, as with natural OP-1, stage 11 mesenchymal cells, cultured in vitro in the presence of OP-1 morphon, e.g., 10–100 ng/ml, will continue to differentiate in vitro to form chondrocytes just as they continue to differentiate in vitro if they are cultured with the cell products harvested from the overlying endodermal cells. This experiment may be performed with different mesenchymal cells to demonstrate the cell differentiation capability of OP-1 morphon in different tissues.

As another example of morphogen-induced cell differentiation, the ability of OP-1 morphons to induce osteoblast differentiation may be demonstrated in vitro using primary osteoblast cultures, or osteoblast-like cells lines, and assaying for a variety of bone cell markers that are specific markers for the differentiated osteoblast phenotype, e.g., alkaline phosphatase activity, parathyroid hormone-mediated cyclic AMP (cAMP) production, osteocalcin synthesis, and enhanced mineralization rates.

(2) Alkaline Phosphatase Induction of Osteoblasts

Cultured osteoblasts in serum-free medium are incubated with, a range of OP-1 morphon concentrations, for example, 0.1, 1.0, 10.0, 40.0 or 80.0 ng OP-1 morphon/ml medium; or with a similar concentration range of natural OP-1 or TGF-β. After a 72 hour incubation the cell layer is extracted with 0.5 ml of 1% Triton X-100. The resultant cell extract, is centrifuged, and 100 ml of the extract is added to 90 ml of paranitroso-phenylphosphate (PNPP)/glycerine mixture and incubated for 30 minutes in a 37° C. water bath and the reaction stopped with 100 ml NaOH. The samples then are run through a plate reader (e.g., Dynatech MR700 plate reader, and absorbance measured at 400 nm, using p-nitrophenol as a standard) to determine the presence and amount of alkaline phosphate activity. Protein concentrations are determined by the BioRad method. Alkaline phosphatase activity is calculated in units/mg protein, where 1 unit=1 nmol p-nitrophenol liberated/30 minutes at 37° C.

It is contemplated that the OP-1 morphon, like natural OP-1 alone, will stimulate the production of alkaline phosphatase in osteoblasts thereby promoting the growth and expression of the osteoblast differentiated phenotype.

The long term effect of OP-1 morphon on the production of alkaline phosphatase by rat osteoblasts also may be demonstrated as follows.

Rat osteoblasts are prepared and cultured in multi-well plates as described above. In this example six sets of 24 well plates are plated with 50,000 rat osteoblasts per well. The wells in each plate, prepared as described above, then are divided into three groups: (1) those which receive, for example, 1 ng of OP-1 morphon per ml of medium; (2) those which receive 40 ng of OP-1 morphon per ml of medium; and (3) those which received 80 ng of OP-1 morphon per ml of medium. Each plate then is incubated for different lengths of time: 0 hours (control time), 24 hours, 48 hours, 96 hours, 120 hours and 144 hours. After each incubation period, the cell layer is extracted with 0.5 ml of 1% Triton X-100. The resultant cell extract is centrifuged, and alkaline phosphatase activity determined using paranitroso-phenylphosphate (PNPP), as above. It is contemplated that the OP-1 morphon, like natural OP-1, will stimulate the production of alkaline phosphatase in osteoblasts in dose-dependent manner so that increasing doses of OP-1 morphon will further increase the level of alkaline phosphatase production. Moreover, it is contemplated that the OP-1 morphon-stimulated elevated levels of alkaline phosphatase in the treated osteoblasts will last for an extended period of time.

(3) Induction of PTH-Mediated cAMP

This experiment is designed to test the effect of OP-1 morphons on parathyroid hormone-mediated cAMP production in rat osteoblasts in vitro. Briefly, rat osteoblasts are prepared and cultured in a multiwell plate as described above. The cultured cells then are divided into four groups: (1) wells which receive, for example, 1.0, 10.0 and 40.0 ng OP-1 morphon/ml medium); (2) wells which receive for example, natural OP-1, at similar concentration ranges; (3) wells which receive for example, TGF-β, at similar concentration ranges; and (4) a control group which receives no growth factors. The plate then is incubated for another 72 hours. At the end of the 72 hours the cells are treated with medium containing 0.5% bovine serum albumin (BSA) and 1 mM 3-isobutyl-1-methylxanthine for 20 minutes followed by the addition into half of the wells of human recombinant parathyroid hormone (hPTH, Sigma, St. Louis) at a concentration of 200 ng/ml for 10 minutes. The cell layer then is extracted from each well with 0.5 ml of 1% Triton X-100. The cAMP levels then are determined using a radioimmunoassay kit (e.g., Amersham, Arlington Heights, Ill.). It is contemplated that OP-1 morphon alone, like OP-1, will stimulate an increase in the PTH-mediated cAMP response, thereby promoting the growth and expression of the osteoblast differentiated phenotype.

(4) Induction of Osteocalcin Production

Osteocalcin is a bone-specific protein synthesized by osteoblasts which plays an integral role in the rate of bone mineralization in vivo. Circulating levels of osteocalcin in serum are used as a marker for osteoblast activity and bone formation in vivo. Induction of osteocalcin synthesis in osteoblast-enriched cultures can be used to demonstrate OP-1 morphon efficacy in vitro.

Rat osteoblasts are prepared and cultured in a multi-well plate as above. In this experiment the medium is supplemented with 10%FBS, and on day 2, cells are fed with fresh medium supplemented with fresh 10 mM β-glycerophosphate (Sigma, Inc.). Beginning on day 5 and twice weekly thereafter, cells are fed with a complete mineralization medium containing all of the above components plus fresh L(+)-ascorbate, at a final concentration of 50 mg/ml medium. OP-1 morphon then is added to the wells directly, e.g., in 50% acetonitrile (or 50% ethanol) containing 0.1% trifluoroacetic acid (TFA), at no more than 5ml morphon/ml medium. Control wells receive solvent vehicle only. The cells then are re-fed and the conditioned medium sample diluted 1:1 in standard radioimmunoassay buffer containing standard protease inhibitors and stored at −20° C. until assayed for osteocalcin. Osteocalcin synthesis is measured by standard radioimmunoassay using a commercially available osteocalcin-specific antibody.

Mineralization is determined on long term cultures (13 day) using a modified von Kossa staining technique on fixed cell layers: cells are fixed in fresh 4% paraformaldehyde at 23° C. for 10 min, following rinsing cold 0.9% NaCl. Fixed cells then are stained for endogenous alkaline phosphatase at pH 9.5 for 10 min, using a commercially available kit (Sigma, Inc.). Purple stained cells then are dehydrated with methanol and air dried. After 30 min incubation in 3% $AgNO_3$ in the dark, $H_2$O-rinsed samples are exposed for 30 sec to 254 nm UV light to develop the black silver-stained phosphate nodules. Individual mineralized foci (at least 20 mm in size) are counted under a dissecting microscope and expressed as nodules/culture.

It is contemplated that the OP-1 morphon, like natural OP-1, will stimulate osteocalcin synthesis in osteoblast cultures. Furthermore, it is contemplated that the increased osteocalcin synthesis in response to OP-1 morphon will be in a dose dependent manner thereby showing a significant increase over the basal level after 13 days of incubation. The enhanced osteocalcin synthesis also may be confirmed by detecting the elevated osteocalcin mRNA message (20-fold increase) using a rat osteocalcin-specific probe. In addition, the increase in osteoclacin synthesis correlates with increased mineralization in long term osteoblast cultures as determined by the appearance of mineral nodules. It is contemplated also that OP-1 morphon, like natural OP-1, will increase significantly the initial mineralization rate as compared to untreated cultures.

(5) Morphogen-Induced CAM Expression

Members of the vg/dpp subgroup induce CAM expression, particularly N-CAM expression, as part of their induction of morphogenesis (see copending USSN 922, 813). CAMs are morphoregulatory molecules identified in all tissues as an essential step in tissue development. N-CAMs, which comprise at least 3 isoforms (N-CAM-180, N-CAM-1 40 and N-CAM-120, where "180", "140" and "120" indicate the apparent molecular weights of the isoforms as measured by SDS polyacrylamide gel electrophoresis) are expressed at least transiently in developing tissues, and permanently in nerve tissue. Both the N-CAM-180 and N-CAM-140 isoforms are expressed in both developing and adult tissue. The N-CAM-120 isoform is found only in adult tissue. Another neural CAM is L1.

The ability of OP-1 based morphons to stimulate CAM expression may be demonstrated using the following protocol, using NG108-15 cells. NG108-15 is a transformed hybrid cell line (neuroblastoma x glioma, America Type Tissue Culture (ATCC), Rockville, Md.), exhibiting a morphology characteristic of transformed embryonic neurons. As described in Example D, below, untreated NG108-15 cells exhibit a fibroblastic, or minimally differentiated, morphology and express only the 180 and 140 isoforms of N-CAM normally associated with a developing cell. Following treatment with members of the vg/dpp subgroup these cells exhibit a morphology characteristic of adult neurons and express enhanced levels of all three N-CAM isoforms.

In this example, NG108-15 cells are cultured for 4 days in the presence of increasing concentrations of either the OP-1 morphon or natural OP-1 using standard culturing procedures, and standard Western blots performed on whole cell extracts. N-CAM isoforms are detected with an antibody which crossreacts with all three isoforms, mAb H28.123, obtained from Sigma Chemical Co., St. Louis, the different isoforms being distinguishable by their different mobilities on an electrophoresis gel. Control NG108-15 cells (untreated) express both the 140 kDa and the 180 kDa isoforms, but not the 120 kDa, as determined by Western blot analyses using up to 100 mg of protein. It is contemplated that treatment of NG108-15 cells with OP-1 morphon, like natural OP-1 may result in a dose-dependent increase in the expression of the 180 kDa and 140 kDa isoforms, as well as the induction of the 120 kDa isoform induced. In addition, it is contemplated that the OP-1 morphon, like natural OP-1-induced CAM expression may correlate with cell aggregation, as determined by histology.

(D) OP-1 Morphon-Induced Redifferentiation of Transformed Phenotype

It is contemplated that OP-1 morphon, like natural OP-1, also induces redifferentiation of transformed cells to a morphology characteristic of untransformed cells. The examples provided below detail morphogen-induced redifferentiation of a transformed human cell line of neuronal origin (NG108-15); as well as mouse neuroblastoma cells (N1E-115), and human embryo carcinoma cells, to a morphology characteristic of untransformed cells.

As described above, NG108-15 is a transformed hybrid cell line produced by fusing neuroblastoma x glioma cells (obtained from ATTC, Rockville, Md.), and exhibiting a morphology characteristic of transformed embryonic neurons, e.g., having a fibroblastic morphology. Specifically, the cells have polygonal cell bodies, short, spike-like processes and make few contacts with neighboring cells. Incubation of NG108-15 cells, cultured in a chemically defined, serum-free medium, with 0.1 to 300 ng/ml of OP-1 morphon natural or OP-1 for four hours induces an orderly, dose-dependent change in cell morphology.

For example, NG108-15 cells are subcultured on poly-L-lysine coated 6 well plates. Each well contains 40–50,000 cells in 2.5 ml of chemically defined medium. On the third day, 2.5 ml of OP-1 morphon or natural OP-1 in 60% ethanol containing 0.025% trifluoroacetic is added to each well. The media is changed daily with new aliquots of morphogen. It is contemplated that OP-1 morphon like OP-1 may induce a dose-dependent redifferentiation of the transformed cells, including a rounding of the soma, an increase in phase brightness, extension of the short neurite processes, and other significant changes in the cellular ultrastructure. After several days it is contemplated also that treated cells may begin to form epithelioid sheets that then become highly packed, multi-layered aggregates, as determined visually by microscopic examination.

Moreover, it is contemplated that the redifferentiation may occur without any associated changes in DNA synthesis, cell division, or cell viability, making it unlikely that the morphologic changes are secondary to cell differentiation or a toxic effect of the morphogen. In addition, it is contemplated that the morphon-induced redifferentiation may not inhibit cell division, as determined by $^3$H-thymidine uptake, unlike other molecules such as butyrate, DMSO, retinoic acid or Forskolin which have been shown to stimulate differentiation of transformed cells, in analogous experiments. Thus, it is contemplated that the OP-1 morphon like natural OP-1 may maintain cell stability and viability after inducing redifferentiation.

The morphogen described herein would, therefore, provide useful therapeutic agents for the treatment of neoplasias and neoplastic lesions of the nervous system, particularly in the treatment of neuroblastomas, including retinoblastomas, and gliomas.

(E) Maintenance of Phenotype.

OP-1 morphons, like natural OP-1 also may be used to maintain a cell's differentiated phenotype. This application is particularly useful for inducing the continued expression of phenotype in senescent or quiescent cells.

(1) In Vitro Model for Phenotypic Maintenance

The phenotypic maintenance capability of morphogens is determined readily. A number of differentiated cells become senescent or quiescent after multiple passages in vitro under standard tissue culture conditions well described in the art (e.g., *Culture of Animal Cells: A Manual of Basic Techniques*, C. R. Freshney, ed., Wiley, 1987). However, if these cells are cultivated in vitro in association with a morphogen such as OP-1, cells are stimulated to maintain expression of their phenotype through multiple passages. For example, the alkaline phosphatase activity of cultured osteoblasts, such as cultured osteosarcoma cells and calvaria cells, is significantly reduced after multiple passages in vitro. However, if the cells are cultivated in the presence of OP-1 alkaline phosphatase activity is maintained over extended periods of time. Similarly, phenotypic expression of myocytes also is maintained in the presence of a morphogen. In the experiment, osteoblasts are cultured as described in Example A. The cells are divided into groups, incubated with varying concentrations of either OP-1 morphon or natural OP-1 (e.g., 0–300 ng/ml) and passaged multiple times (e.g., 3–5 times) using standard methodology. Passaged cells then are tested for alkaline phosphatase activity, as described in Example C as an indication of differentiated cell metabolic function. It is contemplated that osteoblasts cultured in the absence of OP-1 morphon, like natural OP-1, may have reduced alkaline phosphatase activity, as compared to OP-1 morphon, or natural OP-1-treated cells.

(2) In Vivo Model for Phenotypic Maintenance

Phenotypic maintenance capability also may be demonstrated in vivo, using a standard rat model for osteoporosis. Long Evans female rats (Charles River Laboratories, Wilmington, Mass.) are Sham-operated (control animals) or ovariectomized using standard surgical techniques, to produce an osteoporotic condition resulting from decreased estrogen production. Following surgery, e.g., 200 days after ovariectomy, rats are systemically provided with phosphate buffered saline (PBS) or morphogen, (e.g., OP-1 morphon, or natural OP-1, 1–100 mg) for 21 days (e.g., by daily tail vein injection.) The rats then are sacrificed and serum alkaline phosphatase levels, serum calcium levels, and serum osteocalcin levels are determined, using standard methodologies as described therein and above. It is contemplated that the OP-1 morphon treated rats, like the OP-1 treated rats may exhibit elevated levels of osteocalcin and alkaline phosphatase activity. It is contemplated also that histomorphometric analysis on the tibial diasypheal bone may show improved bone mass in OP-1 morphon treated animals as compared with untreated, ovariectomized rats.

F. Proliferation of Progenitor Cell Populations

Progenitor cells may be stimulated to proliferate in vivo or ex vivo. It is contemplated that cells may be stimulated in vivo by injecting or otherwise providing a sterile preparation containing the OP-1 morphon into the individual. For example, the hemopoietic pluripotential stem cell population of an individual may be stimulated to proliferate by injecting or otherwise providing an appropriate concentration of OP-1 morphon to the individual's bone marrow.

Progenitor cells may be stimulated ex vivo by contacting progenitor cells of the population to be enhanced with a morphogenically active OP-1 morphon under sterile conditions at a concentration and for a time sufficient to stimulate proliferation of the cells. Suitable concentrations and stimulation times may be determined empirically, essentially following the procedure described in Example A, above. It is contemplated that a OP-1 morphon concentration of between about 0.1–100 ng/ml and a stimulation period of from about 10 minutes to about 72 hours, or, more generally, about 24 hours, typically should be sufficient to stimulate a cell population of about $10^4$ to $10^6$ cells. The stimulated cells then may be provided to the individual as, for example, by injecting the cells to an appropriate in vivo locus. Suitable biocompatible progenitor cells may be obtained by any of the methods known in the art or described hereinabove.

G. Regeneration of Damaged or Diseased Tissue

It is contemplated that OP-1 morphons may be used to repair diseased or damaged mammalian tissue. The tissue to be repaired preferably is assessed first, and excess necrotic or interfering scar tissue removed as needed, e.g., by ablation or by surgical, chemical, or other methods known in the medical arts.

OP-1 morphon then may be provided directly to the tissue locus as part of a sterile, biocompatible composition, either by surgical implantation or injection. The morphon also may be provided systemically, as by oral or parenteral administration. Alternatively, a sterile, biocompatible composition containing progenitor cells stimulated by a morphogenically active OP-1 morphon may be provided to the tissue locus. The existing tissue at the locus, whether diseased or damaged, provides the appropriate matrix to allow the proliferation and tissue-specific differentiation of progenitor cells. In addition, a damaged or diseased tissue locus, particularly one that has been further assaulted by surgical means, provides a morphogenically permissive environment. Systemic provision of OP-1 morphon may be sufficient for certain applications (e.g., in the treatment of osteoporosis and other disorders of the bone remodeling cycle, as an example).

In some circumstances, particularly where tissue damage is extensive, the tissue may not be capable of providing a sufficient matrix for cell influx and proliferation. In these instances, it may be necessary to provide progenitor cells stimulated by the OP-1 morphon to the tissue locus in association with a suitable, biocompatible, formulated matrix, prepared by any of the means described below. The matrix preferably is in vivo biodegradable. The matrix also may be tissue-specific and/or may comprise porous particles having dimensions within the range of 70–850 mm, most preferably 150–420 mm.

OP-1 morphon also may be used to prevent or substantially inhibit immune/inflammatory response-mediated tissue damage and scar tissue formation following an injury. OP-1 morphon may be provided to a newly injured tissue locus, to induce tissue morphogenesis at the locus, preventing the aggregation of migrating fibroblasts into nondifferentiated connective tissue. Preferably the OP-1 morphon may be provided as a sterile pharmaceutical preparation injected into the tissue locus within five hours of the injury. Where an immune/inflammatory response is unavoidably or deliberately induced, as part of, for example, a surgical or other aggressive clinical therapy, OP-1 morphon preferably may be provided prophylactically to the patient, prior to, or concomitant with, the therapy.

Below are several examples, describing protocols for demonstrating OP-1 morphoninduced tissue morphogenesis in bone, liver, nerve, dentin, cementum and periodontal tissue.

(1) OP-1 Morphon-Induced Bone Morphogenesis

A particularly useful mammalian tissue model system for demonstrating and evaluating the morphogenic activity of a protein is the endochondral bone tissue morphogenesis model known in the art and described, for example, in U.S. Pat. No. 4,968,590 and incorporated herein by reference. The ability to induce endochondral bone formation includes the ability to induce proliferation and differentiation of progenitor cells into chondroblasts and osteoblasts, the ability to induce cartilage matrix formation, cartilage calcification, and bone remodeling, and the ability to induce formation of an appropriate vascular supply and hematopoeitic bone marrow differentiation.

The local environment in which the morphogenic material is placed is important for tissue morphogenesis. As used herein, "local environment" is understood to include the tissue structural matrix and the environment surrounding the tissue. For example, in addition to needing an appropriate anchoring substratum for their proliferation, the cells stimulated by morphogens need signals to direct the tissue-specificity of their differentiation. These signals vary for the different tissues and may include cell surface markers. In addition, vascularization of new tissue requires a local environment which supports vascularization.

The following sets forth various procedures for evaluating the in vivo morphogenic utility of OP-1 morphon and OP-1 morphon containing compositions. The compositions may be injected or surgically implanted in a mammal, following any of a number of procedures well known in the art. For example, surgical implant bioassays may be performed essentially following the procedure of Sampath et al. (1983) *Proc. Natl. Acad. Sci. USA* 80: 6591–6595 and U.S. Pat. No. 4,968,590.

Histological sectioning and staining is preferred to determine the extent of morphogenesis in vivo, particularly in tissue repair procedures. Excised implants are fixed in Bouins Solution, embedded in paraffin, and cut into 6–8 mm sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include: (1) leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoclastic cells, and the commencement of bone remodeling and dissolution of the implanted matrix on days twelve to eighteen; and (8) hematopoietic bone marrow differentiation in the resulting ossicles on day twenty-one.

In addition to histological evaluation, biological markers may be used as markers for tissue morphogenesis. Useful markers include tissue-specific enzymes whose activities may be assayed (e.g., spectrophotometrically) after homogenization of the implant. These assays may be useful for quantitation and for rapidly obtaining an estimate of tissue formation after the implants are removed from the animal. For example, alkaline phosphatase activity may be used as a marker for osteogenesis.

Incorporation of systemically provided OP-1 morphon may be followed using labelled protein (e.g., radioactively labelled) and determining its localization in the new tissue, and/or by monitoring their disappearance from the circulatory system using a standard labeling protocol and pulse-chase procedure. OP-1 morphon also may be provided with a tissue-specific molecular tag, whose uptake may be monitored and correlated with the concentration of OP-1 morphon provided. As an example, ovary removal in female rats results in reduced bone alkaline phosphatase activity, and renders the rats predisposed to osteoporosis (as described in Example E). If the female rats now are provided with OP-1 morphon, a reduction in the systemic concentration of calcium may be seen, which correlates with the presence of the provided OP-1 morphon and which is anticipated to correspond with increased alkaline phosphatase activity.

(2) OP-1 Morphon-Induced Liver Regeneration

As another example, a method for inducing morphogenesis of substantially injured liver tissue following a partial hepatectomy utilizing OP-1 morphon is presented. Variations on this general protocol may be used to test morphogen activity of OP-1 morphon in other different tissues. The general method involves excising an essentially nonregenerating portion of a tissue and providing OP-1 morphon, preferably as a soluble pharmaceutical preparation to the excised tissue locus, closing the wound, and examining the site at a future date. Like bone, liver has a potential to regenerate upon injury during post-fetal life.

OP-1 morphon, e.g., 1 mg/ml, in a biocompatible solution, for example, a purified OP-1 morphon, is solubilized in 50% ethanol, or compatible solvent, containing 0.1% trifluoroacetic acid, or compatible acid. The injectable OP-1 morphon solution is prepared, e.g., by diluting one volume of OP-1 morphon solvent-acid stock solution with 9 volumes of 0.2% rat serum albumin in sterile PBS (phosphate-buffered saline).

In the experiment, growing rats or aged rats (e.g., Long Evans, Charles River Laboratories, Wilmington) are anesthetized by using ketamine. Two of the liver lobes (left and right) are cut out (approximately 1/3 of the lobe) and the OP-1 morphon is injected locally at multiple sites along the cut ends. The amount of OP-1 morphon injected may be, e.g., 20–100 µg in 100–1000 µl PBS/RSA (phosphate buffered saline/rat serum albumin) injection buffer. Placebo samples comprise injection buffer only. In experimental essays, five rats in each group preferably are used. The wound is closed and the rats are allowed to eat normal food and drink tap water.

After 12 days, the rats are sacrificed and liver regeneration is observed visually, to evaluate the effects of the OP-1 morphon on liver regeneration most effectively. It is contemplated that the OP-1 morphon injected group may show complete liver tissue regeneration with no sign remaining of any cut in the liver. By contrast, the control group into which only PBS is injected, show typically only minimal regeneration with the incision remaining in the sample.

(3) OP-1 Morphon-Induced Dentin, Cementum and Periodontal Ligament Regeneration

As still another example, the ability of OP-1 morphons to induce dentinogenesis also may be demonstrated. To date, the unpredictable response of dental pulp tissue to injury is a basic clinical problem in dentistry. Cynomolgus monkeys are chosen as primate models as monkeys are presumed to be more indicative of human dental biology than models based on lower non-primate mammals.

Using standard dental surgical procedures, small areas (e.g., 2 mm) of dental pulps are surgically exposed by removing the enamel and dentin immediately above the pulp (by drilling) of sample teeth, performing a partial amputation of the coronal pulp tissue, inducing hemostasis, application of the pulp treatment, and sealing and filling the cavity by standard procedures.

Pulp treatments used may include: an OP-1 morphon dispersed in a carrier matrix; carrier matrix alone, and no treatment. Twelve teeth per animal (four for each treatment) are prepared, and two animals are used. At four weeks, teeth are extracted and processed histologically for analysis of dentin formation, and/or ground to analyze dentin mineralization. The effect of OP-1 morphon on osteodentin reparation may be observed visually by comparing with the control samples. It is contemplated that the OP-1 morphon, like natural OP-1, plus a carrier matrix may induce formation of reparative, osteodentin bridges, traversing on surgically exposed healthy dental pulps. By contrast, pulps treated with carrier matrix alone, do not form reparative dentin.

(4) OP-1 Morphon-Induced Nerve Tissue Repair

As yet another example, the induction of regenerative effects on central nervous system (CNS) repair, by a morphogenically active OP-1 morphon, may be demonstrated using a rat brain stab model. Briefly, male Long Evans rats are anesthetized and the head area prepared for surgery. The calvariae is exposed using standard surgical procedures and a hole drilled toward the center of each lobe using a 0.035 K wire, just piercing the calvariae. 25 ml solutions containing either OP-1 morphon (25 mg), natural OP-1 (25 mg) or PBS then is provided to each of the holes by Hamilton syringe. Solutions are delivered to a depth approximately 3 mm below the surface, into the underlying cortex, corpus callosum and hippocampus. The skin then is sutured and the animal allowed to recover.

Three days post surgery, rats are sacrificed by decapitation and their brains processed for sectioning. Scar tissue formation is evaluated by immunofluoresence staining for glial fibrillary acidic protein, a marker protein for glial scarring, to qualitatively determine the degree of scar formation. It is contemplated that the OP-1 morphon, like natural OP-1, may result in reduced levels of glial fibrillary acidic protein in the tissue sections of animals treated with OP-1 morphon, evidencing the ability of the morphogen to inhibit glial scar formation, thereby stimulating nerve regeneration.

The ability of OP-1 morphon to stimulate peripheral nervous system axonal growth over extended distances may be demonstrated using the following model. Neurons of the peripheral nervous system can sprout new processes on their own following injury, but without guidance these sproutings typically fail to connect appropriately and die. Where the break is extensive, e.g., greater than 5 or 10 mm, regeneration is poor or nonexistent. Previous experiments with OP-1, show that morphogens stimulate peripheral nervous system axonal growth over extended distances, allowing repair and regeneration of damaged peripheral neural pathways.

In this example OP-1 morphon stimulation of nerve regeneration may be demonstrated using the rat sciatic nerve model. The rat sciatic nerve can regenerate spontaneously across a 5 mm gap, and occasionally across a 10 mm gap, provided that the severed ends are inserted in a saline-filled nerve guidance channel. In this experiment, nerve regeneration across at least a 12mm gap is tested.

Adult female Sprague-Dawley rats (Charles River Laboratories, Inc.) weighing 230–250 g are anesthetized with intraperitoneal injections of sodium pentobarbital (35 mg/kg body weight). A skin incision is made parallel and just posterior to the femur. The avascular intermuscular plane between vastus lateralis and hamstring muscles are entered and followed to the loose fibroareolar tissue surrounding the sciatic nerve. The loose tissue is divided longitudinally thereby freeing the sciatic nerve over its full extent without devascularizing any portion. Under a surgical microscope the sciatic nerves are transected with microscissors at mid-thigh and grafted with an OP-1 morphon gel graft that separates the nerve stumps by 12 mm. The graft region is encased in a silicone tube 20 mm in length with a 1.5 mm inner diameter, the interior of which is filled with the morphon solution. Specifically, the central 12 mm of the tube consists of an OP-1 morphon gel prepared by mixing 1 to 5 mg of substantially pure OP-1 morphon produced with approximately 100 ml of MATRIGEL™ (from Collaborative Research, Inc., Bedford, Mass.), an extracellular matrix extract derived from mouse sarcoma tissue, and containing solubilized tissue basement membrane, including laminin, type IV collagen, heparin sulfate, proteoglycan and entactin, in phosphate-buffered saline. The morphon-filled tube then is implanted directly into the defect site, allowing 4 mm on each end to insert the nerve stumps. Each stump is abutted against the morphon gel and is secured in the silicone tube by three stitches of commercially available surgical 10-0 nylon through the epineurium, the fascicle protective sheath.

In addition to OP-1 morphon gel grafts, control grafts of empty silicone tubes, silicone tubes filled with gel only and "reverse" autografts, wherein 12 mm transected segments of the animal's sciatic nerve are rotated 180° prior to suturing, preferably also are grafted. All experiments preferably are performed in quadruplicate. All wounds preferably are closed by wound clips that are removed after 10 days. Rats can be grafted on both legs. At 3 weeks the animals are sacrificed, and the grafted segments removed and frozen on dry ice immediately. Frozen sections then are cut throughout the graft site, and examined for axonal regeneration by immunofluorescent staining using anti-neurofilament antibodies labeled with flurocein (obtained, for example, from Sigma Chemical Co., St. Louis).

It is contemplated that regeneration of the sciatic nerve may occur across the entire 12 mm distance in all graft sites when the gap is filled with the OP-1 morphon gel. By contrast, empty silicone tubes, gel alone and reverse autografts do not show nerve regeneration.

The invention may be embodied in other specific forms without departing from the spirit and scope thereof. Accordingly, other embodiments are within the following claims.

What is claimed is:

1. A biosynthetic single-chain protein comprising:

a single polypeptide chain defined by a formula selected from the group consisting of:

(a) F1-L-F2-L-H;

(b) F1-L-H-L-F2;

(c) F2-L-F1-L-H;

(d) F2-L-H-L-F1;

(e) H-L-F1-L-F2; and (f) H-L-F2-L-F1;

wherein F1 comprises an amino acid sequence comprising amino acid residues 7–26 of SEQ ID NO: 16, H comprises an amino acid sequence comprising amino acid residues 56–62 of SEQ ID NO: 16, F2 comprises an amino acid sequence comprising amino acid residues 79–87 of SEQ ID NO:16, and L comprises a polypeptide linker, and wherein the single-chain protein is capable of inducing endochondral bone formation in a mammal.

2. The biosynthetic single-chain protein of claim 1, wherein H comprises residues 52–64 of SEQ ID NO: 16.

3. The biosynthetic single-chain protein of claims 2, wherein F2 comprises residues 77–89 of SEQ ID NO: 16.

4. The biosynthetic single-chain protein of claim 1, wherein F2 comprises residues 77–89 of SEQ ID NO: 16.

5. The biosynthetic single-chain protein of claim 1, wherein F1 comprises residues 5–28 of SEQ ID NO: 16.

6. The biosynthetic single-chain protein of claim 1 or 5, wherein H comprises residues 49–64 of SEQ ID NO: 16.

7. The biosynthetic single-chain protein of claim 6, wherein F2 comprises residues 75–91 of SEQ ID NO:16.

8. The biosynthetic single-chain protein of claim 1 or 5, wherein F2 comprises residues 75–91 of SEQ ID NO:16.

9. The biosynthetic single-chain protein of claim 1 comprising the amino acid sequence of SEQ ID NO: 30.

* * * * *

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..98
        (D) OTHER INFORMATION: /note= "TGF-B1 SEQUENCE"

(xi) SEQUENCE DESCRIPTION: SEQ ID NO:1:

```
Cys Cys Val Arg Gln Leu Tyr Ile Asp Phe Arg Lys Asp Leu Gly Trp
1               5                   10                  15

Lys Trp Ile His Glu Pro Lys Gly Tyr His Ala Asn Phe Cys Leu Gly
            20                  25                  30

Pro Cys Pro Tyr Ile Trp Ser Leu Asp Thr Gln Tyr Ser Lys Val Leu
        35                  40                  45

Ala Leu Tyr Asn Gln His Asn Pro Gly Ala Ser Ala Ala Pro Cys Cys
    50                  55                  60

Val Pro Gln Ala Leu Glu Pro Leu Pro Ile Val Tyr Tyr Val Gly Arg
65                  70                  75                  80

Lys Pro Lys Val Glu Gln Leu Ser Asn Met Ile Val Arg Ser Cys Lys
                85                  90                  95

Cys Ser
```

(2) INFORMATION FOR SEQ ID NO:2:

(i) SEQUENCE CHARACTERISTICS:
            (A) LENGTH: 98 amino acids
            (B) TYPE: amino acid
            (C) STRANDEDNESS: single
            (D) TOPOLOGY: linear (ii) MOLECULE TYPE: protein (ix) FEATURE:
            (A) NAME/KEY: Protein
            (B) LOCATION: 1..98
            (D) OTHER INFORMATION: /note= "TGF-B2 SEQUENCE"

(xi) SEQUENCE DESCRIPTION: SEQ ID NO:2:

Cys Cys Leu Arg Pro Leu Tyr Ile Asp Phe Lys Arg Asp Leu Gly Trp
1               5                   10                  15

Lys Trp Ile His Glu Pro Lys Gly Tyr Asn Ala Asn Phe Cys Ala Gly
                20                  25                  30

Ala Cys Pro Tyr Leu Trp Ser Ser Asp Thr Gln His Ser Arg Val Leu
            35                  40                  45

Ser Leu Tyr Asn Thr Ile Asn Pro Glu Ala Ser Ala Ser Pro Cys Cys
        50                  55                  60

Val Ser Gln Asp Leu Glu Pro Leu Thr Ile Leu Tyr Tyr Ile Gly Lys
65                  70                  75                  80

Thr Pro Lys Ile Glu Gln Leu Ser Asn Met Ile Val Lys Ser Cys Lys
                85                  90                  95

Cys Ser (2) INFORMATION FOR SEQ ID NO:3:

(i) SEQUENCE CHARACTERISTICS:
            (A) LENGTH: 98 amino acids
            (B) TYPE: amino acid
            (C) STRANDEDNESS: single
            (D) TOPOLOGY: linear (ii) MOLECULE TYPE: protein (ix) FEATURE:
            (A) NAME/KEY: Protein
            (B) LOCATION: 1..98
            (D) OTHER INFORMATION: /note= "TGF-B3 SEQUENCE"

(xi) SEQUENCE DESCRIPTION: SEQ ID NO:3:

Cys Cys Val Arg Pro Leu Tyr Ile Asp Phe Arg Gln Asp Leu Gly Glu
1               5                   10                  15

Lys Trp Val His Glu Pro Lys Gly Tyr Tyr Ala Asn Phe Cys Ser Gly
                20                  25                  30

Pro Cys Pro Tyr Leu Arg Ser Ala Asp Thr Thr His Ser Thr Val Leu
            35                  40                  45

Gly Leu Tyr Asn Thr Leu Asn Pro Glu Ala Ser Ala Ser Pro Cys Cys
        50                  55                  60

Val Pro Gln Asp Leu Glu Pro Leu Thr Ile Leu Tyr Tyr Val Gly Arg
65                  70                  75                  80

Thr Pro Lys Val Glu Gln Leu Ser Asn Met Val Val Lys Ser Cys Lys
                85                  90                  95

Cys Ser (2) INFORMATION FOR SEQ ID NO:4:

(i) SEQUENCE CHARACTERISTICS:
            (A) LENGTH: 98 amino acids (B) TYPE: amino acid
                (C) STRANDEDNESS: single
                (D) TOPOLOGY: linear (ii) MOLECULE TYPE: protein (ix) FEATURE:
                (A) NAME/KEY: Protein
                (B) LOCATION: 1..98
                (D) OTHER INFORMATION: /note= "TGF-B4 SEQUENCE"

(xi) SEQUENCE DESCRIPTION: SEQ ID NO:4:

```
Cys Cys Val Arg Pro Leu Tyr Ile Asp Phe Arg Lys Asp Leu Gln Trp
1               5                   10                  15

Lys Trp Ile His Glu Pro Lys Gly Tyr Met Ala Asn Phe Cys Met Gly
            20                  25                  30

Pro Cys Pro Tyr Ile Trp Ser Ala Asp Thr Gln Tyr Thr Lys Val Leu
        35                  40                  45

Ala Leu Tyr Asn Gln His Asn Pro Gly Ala Ser Ala Ala Pro Cys Cys
    50                  55                  60

Val Pro Gln Thr Leu Asp Pro Leu Pro Ile Ile Tyr Tyr Val Gly Arg
65                  70                  75                  80

Asn Val Arg Val Glu Gln Leu Ser Asn Met Val Val Arg Ala Cys Lys
                85                  90                  95

Cys Ser
```

(2) INFORMATION FOR SEQ ID NO:5:

(i) SEQUENCE CHARACTERISTICS:
                (A) LENGTH: 98 amino acids
                (B) TYPE: amino acid
                (C) STRANDEDNESS: single
                (D) TOPOLOGY: linear (ii) MOLECULE TYPE: protein (ix) FEATURE:
                (A) NAME/KEY: Protein
                (B) LOCATION: 1..98
                (D) OTHER INFORMATION: /note= "TGF-B5 SEQUENCE"

(xi) SEQUENCE DESCRIPTION: SEQ ID NO:5:

```
Cys Cys Val Lys Pro Leu Tyr Ile Asn Phe Arg Lys Asp Leu Gly Trp
1               5                   10                  15

Lys Trp Ile His Glu Pro Lys Gly Tyr Glu Ala Asn Tyr Cys Leu Gly
            20                  25                  30

Asn Cys Pro Tyr Ile Trp Ser Met Asp Thr Gln Tyr Ser Lys Val Leu
        35                  40                  45

Ser Leu Tyr Asn Gln Asn Asn Pro Gly Ala Ser Ile Ser Pro Cys Cys
    50                  55                  60

Val Pro Asp Val Leu Glu Pro Leu Pro Ile Ile Tyr Tyr Val Gly Arg
65                  70                  75                  80

Thr Ala Lys Val Glu Gln Leu Ser Asn Met Val Val Arg Ser Cys Asn
                85                  90                  95

Cys Ser
```

(2) INFORMATION FOR SEQ ID NO:6:

(i) SEQUENCE CHARACTERISTICS:
                (A) LENGTH: 102 amino acids
                (B) TYPE: amino acid
                (C) STRANDEDNESS: single
                (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "DPP SEQUENCE"

(xi) SEQUENCE DESCRIPTION: SEQ ID NO:6:

Cys Arg Arg His Ser Leu Tyr Val Asp Phe Ser Asp Val Gly Trp Asp
1               5                  10                  15

Asp Trp Ile Val Ala Pro Leu Gly Tyr Asp Ala Tyr Tyr Cys His Gly
            20                  25                  30

Lys Cys Pro Phe Pro Leu Ala Asp His Phe Asn Ser Thr Asn His Ala
        35                  40                  45

Val Val Gln Thr Leu Val Asn Asn Met Asn Pro Gly Lys Val Pro Lys
50                  55                  60

Ala Cys Cys Val Pro Thr Gln Leu Asp Ser Val Ala Met Leu Tyr Leu
65                  70                  75                  80

Asn Asp Gln Ser Thr Val Val Leu Lys Asn Tyr Gln Glu Met Thr Val
                85                  90                  95

Val Gly Cys Gly Cys Arg
            100

(2) INFORMATION FOR SEQ ID NO:7:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "VG1 SEQUENCE"

(xi) SEQUENCE DESCRIPTION: SEQ ID NO:7:

Cys Lys Lys Arg His Leu Tyr Val Glu Phe Lys Asp Val Gly Trp Gln
1               5                  10                  15

Asn Trp Val Ile Ala Pro Gln Gly Tyr Met Ala Asn Tyr Cys Tyr Gly
            20                  25                  30

Glu Cys Pro Tyr Pro Leu Thr Glu Ile Leu Asn Gly Ser Asn His Ala
        35                  40                  45

Ile Leu Gln Thr Leu Val His Ser Ile Glu Pro Glu Asp Ile Pro Leu
50                  55                  60

Pro Cys Cys Val Pro Thr Lys Met Ser Pro Ile Ser Met Leu Phe Tyr
65                  70                  75                  80

Asp Asn Asn Asp Asn Val Val Leu Arg His Tyr Glu Asn Met Ala Val
                85                  90                  95

Asp Glu Cys Gly Cys Arg
            100

(2) INFORMATION FOR SEQ ID NO:8:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
    (A) NAME/KEY: Protein
    (B) LOCATION: 1..102
    (D) OTHER INFORMATION: /note= "VGR1 SEQUENCE"

(xi) SEQUENCE DESCRIPTION: SEQ ID NO:8:

```
Cys Lys Lys Arg His Leu Tyr Val Glu Phe Lys Asp Val Gly Trp Gln
  1               5                  10                  15

Asn Trp Val Ile Ala Pro Gln Gly Tyr Met Ala Asn Tyr Cys Tyr Gly
             20                  25                  30

Glu Cys Pro Tyr Pro Leu Thr Glu Ile Leu Asn Gly Ser Asn His Ala
         35                  40                  45

Ile Leu Gln Thr Leu Val His Ser Ile Glu Pro Glu Asp Ile Pro Leu
 50                  55                  60

Pro Cys Cys Val Pro Thr Lys Met Ser Pro Ile Ser Met Leu Phe Tyr
 65                  70                  75                  80

Asp Asn Asn Asp Asn Val Val Leu Arg His Tyr Glu Asn Met Ala Val
                 85                  90                  95

Asp Glu Cys Gly Cys Arg
            100
```

(2) INFORMATION FOR SEQ ID NO:9:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "60A SEQUENCE"

(xi) SEQUENCE DESCRIPTION: SEQ ID NO:9:

```
Cys Gln Met Gln Thr Leu Tyr Ile Asp Phe Lys Asp Leu Gly Trp His
  1               5                  10                  15

Asp Trp Ile Ile Ala Pro Glu Gly Tyr Gly Ala Phe Tyr Cys Ser Gly
             20                  25                  30

Glu Cys Asn Phe Pro Leu Asn Ala His Met Asn Ala Thr Asn His Ala
         35                  40                  45

Ile Val Gln Thr Leu Val His Leu Leu Glu Pro Lys Lys Val Pro Lys
 50                  55                  60

Pro Cys Cys Ala Pro Thr Arg Leu Gly Ala Leu Pro Val Leu Tyr His
 65                  70                  75                  80

Leu Asn Asp Glu Asn Val Asn Leu Lys Lys Tyr Arg Asn Met Ile Val
                 85                  90                  95

Lys Ser Cys Gly Cys His
            100
```

NFORMATION FOR SEQ ID NO:10:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..101
        (D) OTHER INFORMATION: /note= "BMP-2A SEQUENCE"

(xi) SEQUENCE DESCRIPTION: SEQ ID NO:10:

Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
            20                  25                  30

Glu Cys Pro Phe Pro Leu Ala Asp His Leu Asn Ser Thr Asn His Ala
        35                  40                  45

Ile Val Gln Thr Leu Val Asn Ser Val Asn Ser Lys Ile Pro Lys Ala
    50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
            100

(2) INFORMATION FOR SEQ ID NO:11:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..103
        (D) OTHER INFORMATION: /note= "BMP3 SEQUENCE"

(xi) SEQUENCE DESCRIPTION: SEQ ID NO:11:

Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
            20                  25                  30

Ala Cys Gln Phe Pro Met Pro Lys Ser Leu Lys Pro Ser Asn His Ala
        35                  40                  45

Thr Ile Gln Ser Ile Val Arg Ala Val Gly Val Val Pro Gly Ile Pro
    50                  55                  60

Glu Pro Cys Cys Val Pro Glu Lys Met Ser Ser Leu Ser Ile Leu Phe
65                  70                  75                  80

Phe Asp Glu Asn Lys Asn Val Val Leu Lys Val Tyr Pro Asn Met Thr
                85                  90                  95

Val Glu Ser Cys Ala Cys Arg
            100

(2) INFORMATION FOR SEQ ID NO:12:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (ix) FEATURE:
    (A) NAME/KEY: Protein
    (B) LOCATION: 1..101
    (D) OTHER INFORMATION: /note= "BMP-4 SEQUENCE"

(xi) SEQUENCE DESCRIPTION: SEQ ID NO:12:

```
Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
            35                  40                  45

Ile Val Gln Thr Leu Val Asn Ser Val Asn Ser Ile Pro Lys Ala
        50                  55                  60

Cys Cys Val Pro Thr Glu Leu Ser Ala Ile Ser Met Leu Tyr Leu Asp
65                  70                  75                  80

Glu Tyr Asp Lys Val Val Leu Lys Asn Tyr Gln Glu Met Val Val Glu
                85                  90                  95

Gly Cys Gly Cys Arg
            100
```

(2) INFORMATION FOR SEQ ID NO:13:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "BMP-5 SEQUENCE"

(xi) SEQUENCE DESCRIPTION: SEQ ID NO:13:

```
Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
            20                  25                  30

Glu Cys Ser Phe Pro Leu Asn Ala His Met Asn Ala Thr Asn His Ala
            35                  40                  45

Ile Val Gln Thr Leu Val His Leu Met Phe Pro Asp His Val Pro Lys
        50                  55                  60

Pro Cys Cys Ala Pro Thr Lys Leu Asn Ala Ile Ser Val Leu Tyr Phe
65                  70                  75                  80

Asp Asp Ser Ser Asn Val Ile Leu Lys Lys Tyr Arg Asn Met Val Val
                85                  90                  95

Arg Ser Cys Gly Cys His
            100
```

(2) INFORMATION FOR SEQ ID NO:14:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:

(A) NAME/KEY: Protein
            (B) LOCATION: 1..102
            (D) OTHER INFORMATION: /note= "BMP-6 SEQUENCE"

(xi) SEQUENCE DESCRIPTION: SEQ ID NO:14:

Cys Arg Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Asn Pro Glu Tyr Val Pro Lys
    50                  55                  60

Pro Cys Cys Ala Pro Thr Lys Leu Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
                100

(2) INFORMATION FOR SEQ ID NO:15:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..103
        (D) OTHER INFORMATION: /note= "DORSALIN SEQUENCE"

(xi) SEQUENCE DESCRIPTION: SEQ ID NO:15:

Cys Arg Arg Thr Ser Leu His Val Asn Phe Lys Glu Ile Gly Trp Asp
1               5                   10                  15

Ser Trp Ile Ile Ala Pro Lys Asp Tyr Glu Ala Phe Glu Cys Lys Gly
            20                  25                  30

Gly Cys Phe Phe Pro Leu Thr Asp Asn Val Thr Pro Thr Lys His Ala
        35                  40                  45

Ile Val Gln Thr Leu Val His Leu Gln Asn Pro Lys Lys Ala Ser Lys
    50                  55                  60

Ala Cys Cys Val Pro Thr Lys Leu Asp Ala Ile Ser Ile Leu Tyr Lys
65                  70                  75                  80

Asp Asp Ala Gly Val Pro Thr Leu Ile Tyr Asn Tyr Glu Gly Met Lys
                85                  90                  95

Val Ala Glu Cys Gly Cys Arg
                100

(2) INFORMATION FOR SEQ ID NO:16:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102

(D) OTHER INFORMATION: /note= "OP-1 SEQUENCE"

(xi) SEQUENCE DESCRIPTION: SEQ ID NO:16:

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Tyr Tyr Cys Glu Gly
            20                  25                  30

Glu Cys Ala Phe Pro Leu Asn Ser Tyr Met Asn Ala Thr Asn His Ala
        35                  40                  45

Ile Val Gln Thr Leu Val His Phe Ile Asn Pro Glu Thr Val Pro Lys
50                  55                  60

Pro Cys Cys Ala Pro Thr Gln Leu Asn Ala Ile Ser Val Leu Tyr Phe
65              70                  75                  80

Asp Asp Ser Ser Asn Val Ile Leu Lys Lys Tyr Arg Asn Met Val Val
                85                  90                  95

Arg Ala Cys Gly Cys His
            100

(2) INFORMATION FOR SEQ ID NO:17:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "OP-2 SEQUENCE"

(xi) SEQUENCE DESCRIPTION: SEQ ID NO:17:

Cys Arg Arg His Glu Leu Tyr Val Ser Phe Gln Asp Leu Gly Trp Leu
1               5                   10                  15

Asp Trp Val Ile Ala Pro Gln Gly Tyr Ser Ala Tyr Tyr Cys Glu Gly
            20                  25                  30

Glu Cys Ser Phe Pro Leu Asp Ser Cys Met Asn Ala Thr Asn His Ala
        35                  40                  45

Ile Leu Gln Ser Leu Val His Leu Met Lys Pro Asn Ala Val Pro Lys
50                  55                  60

Ala Cys Cys Ala Pro Thr Lys Leu Ser Ala Thr Ser Val Leu Tyr Tyr
65              70                  75                  80

Asp Ser Ser Asn Asn Val Ile Leu Arg Lys His Arg Asn Met Val Val
                85                  90                  95

Lys Ala Cys Gly Cys His
            100

(2) INFORMATION FOR SEQ ID NO:18:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "OP-3 SEQUENCE"

(xi) SEQUENCE DESCRIPTION: SEQ ID NO:18:

Cys Arg Arg His Glu Leu Tyr Val Ser Phe Arg Asp Leu Gly Trp Leu
    1               5                   10                  15

Asp Ser Val Ile Ala Pro Gln Gly Tyr Ser Ala Tyr Tyr Cys Ala Gly
                    20                  25                  30

Glu Cys Ile Tyr Pro Leu Asn Ser Cys Met Asn Ser Thr Asn His Ala
                35                  40                  45

Thr Met Gln Ala Leu Val His Leu Met Lys Pro Asp Ile Ile Pro Lys
            50                  55                  60

Val Cys Cys Val Pro Thr Glu Leu Ser Ala Ile Ser Leu Leu Tyr Tyr
    65                  70                  75                  80

Asp Arg Asn Asn Asn Val Ile Leu Arg Arg Glu Arg Asn Met Val Val
                    85                  90                  95

Gln Ala Cys Gly Cys His
                100

(2) INFORMATION FOR SEQ ID NO:19:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..107
        (D) OTHER INFORMATION: /note= "GDF-1 SEQUENCE"

(xi) SEQUENCE DESCRIPTION: SEQ ID NO:19:

Cys Arg Thr Arg Arg Leu His Val Ser Phe Arg Glu Val Gly Trp His
    1               5                   10                  15

Arg Trp Val Ile Ala Pro Arg Gly Phe Leu Ala Asn Phe Cys Gln Gly
                    20                  25                  30

Thr Cys Ala Leu Pro Glu Thr Leu Arg Gly Pro Gly Gly Pro Pro Ala
                35                  40                  45

Leu Asn His Ala Val Leu Arg Ala Leu Met His Ala Ala Ala Pro Thr
            50                  55                  60

Pro Gly Ala Gly Ser Pro Cys Cys Val Pro Glu Arg Leu Ser Pro Ile
    65                  70                  75                  80

Ser Val Leu Phe Phe Asp Asn Ser Asp Asn Val Val Leu Arg His Tyr
                    85                  90                  95

Glu Asp Met Val Val Asp Glu Cys Gly Cys Arg
                100                 105

(2) INFORMATION FOR SEQ ID NO:20:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..101
        (D) OTHER INFORMATION: /note= "GDF-3 SEQUENCE"

(xi) SEQUENCE DESCRIPTION: SEQ ID NO:20:

Cys His Arg His Gln Leu Phe Ile Asn Phe Gln Asp Leu Gly Trp His
1               5                   10                  15

Lys Trp Val Ile Ala Pro Lys Gly Phe Met Ala Asn Tyr Cys His Gly
                20                  25                  30

Glu Cys Pro Phe Ser Met Thr Thr Tyr Leu Asn Ser Ser Asn Tyr Ala
            35                  40                  45

Phe Met Gln Ala Leu Met His Met Ala Asp Pro Lys Val Pro Lys Ala
        50                  55                  60

Val Cys Val Pro Thr Lys Leu Ser Pro Ile Ser Met Leu Tyr Gln Asp
65                  70                  75                  80

Ser Asp Lys Asn Val Ile Leu Arg His Tyr Glu Asp Met Val Val Asp
                85                  90                  95

Glu Cys Gly Cys Gly
            100

(2) INFORMATION FOR SEQ ID NO:21:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "GDF-9 SEQUENCE"

(xi) SEQUENCE DESCRIPTION: SEQ ID NO:21:

Cys Glu Leu His Asp Phe Arg Leu Ser Phe Ser Gln Leu Lys Trp Asp
1               5                   10                  15

Asn Trp Ile Val Ala Pro His Arg Tyr Asn Pro Arg Tyr Cys Lys Gly
                20                  25                  30

Asp Cys Pro Arg Ala Val Arg His Arg Tyr Gly Ser Pro Val His Thr
            35                  40                  45

Met Val Gln Asn Ile Ile Tyr Glu Lys Leu Asp Pro Ser Val Pro Arg
        50                  55                  60

Pro Ser Cys Val Pro Gly Lys Tyr Ser Pro Leu Ser Val Leu Thr Ile
65                  70                  75                  80

Glu Pro Asp Gly Ser Ile Ala Tyr Lys Glu Tyr Glu Asp Met Ile Ala
                85                  90                  95

Thr Arg Cys Thr Cys Arg
            100

(2) INFORMATION FOR SEQ ID NO:22:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..105
        (D) OTHER INFORMATION: /note= "INHIBIN-A SEQUENCE"

(xi) SEQUENCE DESCRIPTION: SEQ ID NO:22:

```
Cys His Arg Val Ala Leu Asn Ile Ser Phe Gln Glu Leu Gly Trp Glu
1               5                   10                  15

Arg Trp Ile Val Tyr Pro Pro Ser Phe Ile Phe His Tyr Cys His Gly
            20                  25                  30

Gly Cys Gly Leu His Ile Pro Pro Asn Leu Ser Leu Pro Val Pro Gly
            35                  40                  45

Ala Pro Pro Thr Pro Ala Gln Pro Tyr Ser Leu Leu Pro Gly Ala Gln
        50                  55                  60

Pro Cys Cys Ala Ala Leu Pro Gly Thr Met Arg Pro Leu His Val Arg
65                  70                  75                  80

Thr Thr Ser Asp Gly Gly Tyr Ser Phe Lys Tyr Glu Thr Val Pro Asn
                85                  90                  95

Leu Leu Thr Gln His Cys Ala Cys Ile
            100                 105
```

(2) INFORMATION FOR SEQ ID NO:23:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..106
        (D) OTHER INFORMATION: /note= "INHIBIN-BA SEQUENCE"

(xi) SEQUENCE DESCRIPTION: SEQ ID NO:23:

```
Cys Cys Lys Lys Gln Phe Phe Val Ser Phe Lys Asp Ile Gly Trp Asn
1               5                   10                  15

Asp Trp Ile Ile Ala Pro Ser Gly Tyr His Ala Asn Tyr Cys Glu Gly
            20                  25                  30

Glu Cys Pro Ser His Ile Ala Gly Thr Ser Gly Ser Ser Leu Ser Phe
            35                  40                  45

His Ser Thr Val Ile Asn His Tyr Arg Met Arg Gly His Ser Pro Phe
        50                  55                  60

Ala Asn Leu Lys Ser Cys Cys Val Pro Thr Lys Leu Arg Pro Met Ser
65                  70                  75                  80

Met Leu Tyr Tyr Asp Asp Gly Gln Asn Ile Ile Lys Lys Asp Ile Gln
                85                  90                  95

Asn Met Ile Val Glu Glu Cys Gly Cys Ser
                100                 105
```

(2) INFORMATION FOR SEQ ID NO:24:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..105
        (D) OTHER INFORMATION: /note= "INHIBIN-BB SEQUENCE"

(xi) SEQUENCE DESCRIPTION: SEQ ID NO:24:

```
Cys Cys Arg Gln Gln Phe Phe Ile Asp Phe Arg Leu Ile Gly Trp Asn
  1               5                          10                      15

Asp Trp Ile Ile Ala Pro Thr Gly Tyr Tyr Gly Asn Tyr Cys Glu Gly
              20                  25                  30

Ser Cys Pro Ala Tyr Leu Ala Gly Val Pro Gly Ser Ala Ser Ser Phe
              35                  40                  45

His Thr Ala Val Val Asn Gln Tyr Arg Met Arg Gly Leu Asn Pro Gly
       50                  55                  60

Thr Val Asn Ser Cys Cys Ile Pro Thr Lys Leu Ser Thr Met Ser Met
 65                  70                  75                  80

Leu Tyr Phe Asp Asp Glu Tyr Asn Ile Val Lys Arg Asp Val Pro Asn
                 85                  90                  95

Met Ile Val Glu Glu Cys Gly Cys Ala
             100                 105
```

(2) INFORMATION FOR SEQ ID NO:25:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..98
        (D) OTHER INFORMATION: /note= "TGF-B SUBGROUP SEQUENCE
            PATTERN. Each Xaa is independently selected from
            a group of one or more specified amino acids as
            defined in the specification."

(xi) SEQUENCE DESCRIPTION: SEQ ID NO:25:

```
Cys Cys Val Arg Pro Leu Tyr Ile Asp Phe Arg Xaa Asp Leu Gly Trp
  1               5                          10                      15

Lys Trp Ile His Glu Pro Lys Gly Tyr Xaa Ala Asn Phe Cys Xaa Gly
              20                  25                  30

Xaa Cys Pro Tyr Xaa Trp Ser Xaa Asp Thr Gln Xaa Ser Xaa Val Leu
              35                  40                  45

Xaa Leu Tyr Asn Xaa Xaa Asn Pro Xaa Ala Ser Ala Xaa Pro Cys Cys
       50                  55                  60

Val Pro Gln Xaa Leu Glu Pro Leu Xaa Ile Xaa Tyr Tyr Val Gly Arg
 65                  70                  75                  80

Xaa Xaa Lys Val Glu Gln Leu Ser Asn Met Xaa Val Xaa Ser Cys Lys
                 85                  90                  95

Cys Ser
```

(2) INFORMATION FOR SEQ ID NO:26:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..104
        (D) OTHER INFORMATION: /note= "VG/DPP SUBGROUP SEQUENCE
            PATTERN. Each Xaa is independently selected from
            a group of one or more specified amino acids as -continued defined in the specification"

(xi) SEQUENCE DESCRIPTION: SEQ ID NO:26:

```
Cys Xaa Xaa Xaa Xaa Leu Tyr Val Xaa Phe Xaa Asp Xaa Gly Trp Xaa
1               5                   10                  15

Asp Trp Ile Ile Ala Pro Xaa Gly Tyr Xaa Ala Xaa Tyr Cys Xaa Gly
            20                  25                  30

Xaa Cys Xaa Phe Pro Leu Xaa Xaa Xaa Asn Xaa Thr Asn His Ala
        35                  40                  45

Ile Xaa Gln Thr Leu Val Xaa Xaa Xaa Xaa Xaa Xaa Xaa Xaa Pro
    50                  55                  60

Lys Xaa Cys Cys Xaa Pro Thr Xaa Leu Xaa Ala Xaa Ser Xaa Leu Tyr
65              70                  75                  80

Xaa Asp Xaa Xaa Xaa Xaa Xaa Val Xaa Leu Xaa Xaa Tyr Xaa Xaa Met
                85                  90                  95

Xaa Val Xaa Xaa Cys Gly Cys Xaa
            100
```

(2) INFORMATION FOR SEQ ID NO:27:

(i) SEQUENCE CHARACTERISTICS:
       (A) LENGTH: 107 amino acids
       (B) TYPE: amino acid
       (C) STRANDEDNESS: single
       (D) TOPOLOGY: linear (ii) MOLECULE TYPE: protein (ix) FEATURE:
       (A) NAME/KEY: Protein
       (B) LOCATION: 1..107
       (D) OTHER INFORMATION: /note= "GDF SUBGROUP PATTERN.
           Each Xaa is independently selected from a group
           of one or more specified amino acids as defined
           in the specification"

(xi) SEQUENCE DESCRIPTION: SEQ ID NO:27:

```
Cys Xaa Xaa Xaa Xaa Xaa Xaa Xaa Phe Xaa Xaa Xaa Xaa Trp Xaa
1               5                   10                  15

Xaa Trp Xaa Xaa Ala Pro Xaa Xaa Xaa Xaa Xaa Xaa Cys Xaa Gly
            20                  25                  30

Xaa Cys Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Pro Xaa Xaa Xaa Xaa Xaa Xaa Cys Val Pro Xaa Xaa Xaa Ser Pro Xaa
65              70                  75                  80

Ser Xaa Leu Xaa Xaa Xaa Xaa Xaa Xaa Xaa Xaa Xaa Xaa Xaa Tyr
        85                  90                  95

Glu Asp Met Xaa Xaa Xaa Xaa Cys Xaa Cys Xaa
            100             105
```

(2) INFORMATION FOR SEQ ID NO:28:

(i) SEQUENCE CHARACTERISTICS:
       (A) LENGTH: 109 amino acids
       (B) TYPE: amino acid
       (C) STRANDEDNESS: single
       (D) TOPOLOGY: linear (ii) MOLECULE TYPE: protein (ix) FEATURE:

(A) NAME/KEY: Protein
            (B) LOCATION: 1..109
            (D) OTHER INFORMATION: /note= "INHIBIN SUBGROUP PATTERN.
                Each Xaa is independently selected from a group of
                one or more specified amino acids as defined in
                the specification"

(xi) SEQUENCE DESCRIPTION: SEQ ID NO:28:

Cys Xaa Xaa Xaa Xaa Xaa Xaa Xaa Xaa Phe Xaa Xaa Xaa Gly Trp Xaa
1               5                   10                  15

Xaa Trp Ile Xaa Xaa Pro Xaa Xaa Xaa Xaa Xaa Xaa Tyr Cys Xaa Gly
            20                  25                  30

Xaa Cys Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Cys Cys Xaa Xaa Xaa Pro Xaa Xaa Xaa Xaa Xaa
65                  70                  75                  80

Xaa Xaa Xaa Xaa Xaa Xaa Xaa Asp Xaa Xaa Xaa Xaa Xaa Xaa Xaa Xaa
                85                  90                  95

Xaa Xaa Xaa Asn Xaa Xaa Xaa Xaa Xaa Cys Xaa Cys Xaa
            100                 105

(2) INFORMATION FOR SEQ ID NO:29:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..348
        (D) OTHER INFORMATION: /product= "DNA ENCODING OP-1
            MORPHON"

(xi) SEQUENCE DESCRIPTION: SEQ ID NO:29:

ATGGCTTGTA AGAAGCACGA GCTGTATGTC AGCTTCCGAG ACCTGGGCTG GCAGGACTGG      60

ATCATCGCGC CTGAAGGCTA CGCCGCCTAC TACTGTGGCG GCTCTGGAGG TGGATCCGGT     120

GGAGGCTCCG GTGCCTTCCC TCTGAACTCC TACATGAACG CCACCAACCA CGCCATCGTG     180

CAGACGCTGG TCCACTTCAT CAACCCGGAA ACGGTGCCCA AGCCCGCTAG CGGTGGTTGT     240

GCGCCCACGC AGCTCAATGC CATCTCCGTC CTCTACTTCG ATGACAGCTC CAACGTCATC     300

CTGAAGAAAT ACAGAAACAT GGTGGTCCGG GCATGCGGCT CCCACTAA                  348

(2) INFORMATION FOR SEQ ID NO:30:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..115
        (D) OTHER INFORMATION: /note= "OP-1 MORPHON PROTEIN"

(xi) SEQUENCE DESCRIPTION: SEQ ID NO:30:

```
Met Ala Cys Lys Lys His Glu Leu Tyr Val Ser Phe Arg Asp Leu Gly
 1               5                  10                  15

Trp Gln Asp Trp Ile Ile Ala Pro Glu Gly Tyr Ala Ala Tyr Tyr Cys
                20                  25                  30

Gly Gly Ser Gly Gly Ser Gly Gly Ser Gly Ala Phe Pro Leu
            35                  40                  45

Asn Ser Tyr Met Asn Ala Thr Asn His Ala Ile Val Gln Thr Leu Val
        50                  55                  60

His Phe Ile Asn Pro Glu Thr Val Pro Lys Pro Ala Ser Gly Gly Cys
 65                  70                  75                  80

Ala Pro Thr Gln Leu Asn Ala Ile Ser Val Leu Tyr Phe Asp Asp Ser
                85                  90                  95

Ser Asn Val Ile Leu Lys Lys Tyr Arg Asn Met Val Val Arg Ala Cys
            100                 105                 110

Gly Ser His
        115
```

(2) INFORMATION FOR SEQ ID NO:31:

(i) SEQUENCE CHARACTERISTICS:
        (A) LENGTH: 1878 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..1878
        (D) OTHER INFORMATION: /product= "OP-1 cDNA"

(xi) SEQUENCE DESCRIPTION: SEQ ID NO:31:

```
GGGCGCAGCG GGGCCCGTCT GCAGCAAGTG ACCGACGGCC GGGACGGCCG CCTGCCCCCT      60

CTGCCACCTG GGGCGGTGCG GGCCCGGAGC CCGGAGCCCG GGTAGCGCGT AGAGCCGGCG     120

CGATGCACGT GCGCTCACTG CGAGCTGCGG CGCCGCACAG CTTCGTGGCG CTCTGGGCAC     180

CCCTGTTCCT GCTGCGCTCC GCCCTGGCCG ACTTCAGCCT GGACAACGAG GTGCACTCGA     240

GCTTCATCCA CCGGCGCCTC CGCAGCCAGG AGCGGCGGGA GATGCAGCGC GAGATCCTCT     300

CCATTTTGGG CTTGCCCCAC CGCCCGCGCC CGCACCTCCA GGGCAAGCAC AACTCGGCAC     360

CCATGTTCAT GCTGGACCTG TACAACGCCA TGGCGGTGGA GGAGGGCGGC GGGCCCGGCG     420

GCCAGGGCTT CTCCTACCCC TACAAGGCCG TCTTCAGTAC CCAGGGCCCC CCTCTGGCCA     480

GCCTGCAAGA TAGCCATTTC CTCACCGACG CCGACATGGT CATGAGCTTC GTCAACCTCG     540

TGGAACATGA CAAGGAATTC TTCCACCCAC GCTACCACCA TCGAGAGTTC CGGTTTGATC     600

TTTCCAAGAT CCCAGAAGGG GAAGCTGTCA CGGCAGCCGA ATTCCGGATC TACAAGGACT     660

ACATCCGGGA ACGCTTCGAC AATGAGACGT TCCGGATCAG CGTTTATCAG GTGCTCCAGG     720

AGCACTTGGG CAGGGAATCG GATCTCTTCC TGCTCGACAG CCGTACCCTC TGGGCCTCGG     780

AGGAGGGCTG GCTGGTGTTT GACATCACAG CCACCAGCAA CCACTGGGTG GTCAATCCGC     840

GGCACAACCT GGGCCTGCAG CTCTCGGTGG AGACGCTGGA TGGGCAGAGC ATCAACCCCA     900

AGTTGGCGGG CCTGATTGGG CGGCACGGGC CCCAGAACAA GCAGCCCTTC ATGGTGGCTT     960

TCTTCAAGGC CACGGAGGTC CACTTCCGCA GCATCCGGTC CACGGGGAGC AAACAGCGCA    1020

GCCAGAACCG CTCCAAGACG CCCAAGAACC AGGAAGCCCT GCGGATGGCC AACGTGGCAG    1080

AGAACAGCAG CAGCGACCAG AGGCAGGCCT GTAAGAAGCA CGAGCTGTAT GTCAGCTTCC    1140
```

```
GAGACCTGGG CTGGCAGGAC TGGATCATCG CGCCTGAAGG CTACGCCGCC TACTACTGTG    1200

AGGGGGAGTG TGCCTTCCCT CTGAACTCCT ACATGAACGC CACCAACCAC GCCATCGTGC    1260

AGACGCTGGT CCACTTCATC AACCCGGAAA CGGTGCCCAA GCCCTGCTGT GCGCCCACGC    1320

AGCTCAATGC CATCTCCGTC CTCTACTTCG ATGACAGCTC CAACGTCATC CTGAAGAAAT    1380

ACAGAAACAT GGTGGTCCGG GCCTGTGGCT GCCACTAGCT CCTCCGAGAA TTCAGACCCT    1440

TTGGGGCCAA GTTTTTCTGG ATCCTCCATT GCTCGCCTTG GCCAGGAACC AGCAGACCAA    1500

CTGCCTTTTG TGAGACCTTC CCCTCCCTAT CCCCAACTTT AAAGGTGTGA GAGTATTAGG    1560

AAACATGAGC AGCATATGGC TTTTGATCAG TTTTTCAGTG GCAGCATCCA ATGAACAAGA    1620

TCCTACAAGC TGTGCAGGCA AAACCTAGCA GGAAAAAAAA ACAACGCATA AGAAAAATG     1680

GCCGGGCCAG GTCATTGGCT GGGAAGTCTC AGCCATGCAC GGACTCGTTT CCAGAGGTAA    1740

TTATGAGCGC CTACCAGCCA GGCCACCCAG CCGTGGGAGG AAGGGGGCGT GGCAAGGGGT    1800

GGGCACATTG GTGTCTGTGC GAAAGGAAAA TTGACCCGGA AGTTCCTGTA ATAAATGTCA    1860

CAATAAAACG AATGAATG                                                  1878
```

(2) INFORMATION FOR SEQ ID NO:32:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..60
        (D) OTHER INFORMATION: /product= "N TERMINAL LINKER"

(xi) SEQUENCE DESCRIPTION: SEQ ID NO:32:

```
GCCAACGTGG CAGAGAACAG GGCCGAGCGG GCCCATATGG CTTGTAAGAA GCACGAGCTG      60
```

(2) INFORMATION FOR SEQ ID NO:33:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..48
        (D) OTHER INFORMATION: /product= "SMALL LOOP LINKER"

(xi) SEQUENCE DESCRIPTION: SEQ ID NO:33:

```
GAAACGGTGC CCAAGCCCGC TAGCGGTGGT TGTGCGCCCA CGCAGCTC                   48
```

(2) INFORMATION FOR SEQ ID NO:34:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: misc_feature
        (B) LOCATION: 1..66
        (D) OTHER INFORMATION: /product= "LONG LOOP LINKER"

(xi) SEQUENCE DESCRIPTION: SEQ ID NO:34:

GCCGCCTACT ACTGTGGCGG CTCTGGAGGT GGATCCGGTG GAGGCTCCGG TGCCTTCCCT    60

CTGAAC    66

(2) INFORMATION FOR SEQ ID NO:35:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..52
        (D) OTHER INFORMATION: /product= "C-TERMINAL LINKER 1"

(xi) SEQUENCE DESCRIPTION: SEQ ID NO:35:

CATGGTGGTC CGGGCATGCG GCTCCCACGG TGCGGCCGCA GAATTCAGAC CC    52

(2) INFORMATION FOR SEQ ID NO:36:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..42
        (D) OTHER INFORMATION: /product= "C-TERMINAL LINKER 2"

(xi) SEQUENCE DESCRIPTION: SEQ ID NO:36:

CGGGCATGCG GCTCCCACTA AAGATCTGCA GAATTCAGAC CC    42

(2) INFORMATION FOR SEQ ID NO:37:

(i) SEQUENCE CHARACTERISTICS:
        (A) LENGTH: 1392 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..1392
        (D) OTHER INFORMATION: /product= "MODIFIED OP-1 DNA"
    (xi) SEQUENCE DESCRIPTION: SEQ ID NO:37:

CCCGGGTAGC GCGTAGAGCC GGCGCGATGC ACGTGCGCTC ACTGCGAGCT GCGGCGCCGC    60

ACAGCTTCGT GGCGCTCTGG GCACCCCTGT TCCTGCTGCG CTCCGCCCTG GCCGACTTCA   120

GCCTGGACAA CGAGGTGCAC TCGAGCTTCA TCCACCGGCG CCTCCGCAGC CAGGAGCGGC   180

GGGAGATGCA GCGCGAGATC CTCTCCATTT TGGGCTTGCC CCACCGCCCG CGCCCGCACC   240

TCCAGGGCAA GCACAACTCG GCACCCATGT TCATGCTGGA CCTGTACAAC GCCATGGCGG   300

TGGAGGAGGG CGGCGGGCCC GGCGGCCAGG GCTTCTCCTA CCCCTACAAG GCCGTCTTCA   360

```
GTACCCAGGG CCCCCCTCTG GCCAGCCTGC AAGATAGCCA TTTCCTCACC GACGCCGACA    420

TGGTCATGAG CTTCGTCAAC CTCGTGGAAC ATGACAAGGA ATTCTTCCAC CCACGCTACC    480

ACCATCGAGA GTTCCGGTTT GATCTTTCCA AGATCCCAGA AGGGGAAGCT GTCACGGCAG    540

CCGAATTCCG GATCTACAAG GACTACATCC GGGAACGCTT CGACAATGAG ACGTTCCGGA    600

TCAGCGTTTA TCAGGTGCTC CAGGAGCACT TGGGCAGGGA ATCGGATCTC TTCCTGCTCG    660

ACAGCCGTAC CCTCTGGGCC TCGGAGGAGG GCTGGCTGGT GTTTGACATC ACAGCCACCA    720

GCAACCACTG GGTGGTCAAT CCGCGGCACA ACCTGGGCCT GCAGCTCTCG GTGGAGACGC    780

TGGATGGGCA GAGCATCAAC CCCAAGTTGG CGGGCCTGAT TGGGCGGCAC GGGCCCCAGA    840

ACAAGCAGCC CTTCATGGTG GCTTTCTTCA AGGCCACGGA GGTCCACTTC CGCAGCATCC    900

GGTCCACGGG GAGCAAACAG CGCAGCCAGA ACCGCTCCAA GACGCCCAAG AACCAGGAAG    960

CCCTGCGGAT GGCCAACAGC CCGGCCGAGC GGGCCCATAT GGCTTGTAAG AAGCACGAGC    1020

TGTATGTCAG CTTCCGAGAC CTGGGCTGGC AGGACTGGAT CATCGCGCCT GAAGGCTACG    1080

CCGCCTACTA CTGTGGCGGC TCTGGAGGTG GATCCGGTGG AGGCTCCGGT GCCTTCCCTC    1140

TGAACTCCTA CATGAACGCC ACCAACCACG CCATCGTGCA GACGCTGGTC CACTTCATCA    1200

ACCCGGAAAC GGTGCCCAAG CCCGCTAGCG GTGGTTGTGC GCCCACGCAG CTCAATGCCA    1260

TCTCCGTCCT CTACTTCGAT GACAGCTCCA ACGTCATCCT GAAGAAATAC AGAAACATGG    1320

TGGTCCGGGC ATGCGGCTCC CACGGTGCGG CCGCAGAATT CAGACCCTTT GGGGCCAAGT    1380

TTTTCTGGAT CC                                                       1392

(2) INFORMATION FOR SEQ ID NO:38:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..48
        (D) OTHER INFORMATION: /product= "SMALL LOOP MUTAGENESIS
            SEQUENCE A"

(xi) SEQUENCE DESCRIPTION: SEQ ID NO:38:

GAAACGGTGC CCAAGNNCNN TNNCNNTNNT NNTNNGCCCA CGCAGCTC                 48

(2) INFORMATION FOR SEQ ID NO:39:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..48
        (D) OTHER INFORMATION: /product= "SMALL LOOP MUTAGENESIS
            SEQUENCE B"

(xi) SEQUENCE DESCRIPTION: SEQ ID NO:39:

GAAACGGTGC CCAAGCCCNN NNNNNNNNNN TGTGCGCCCA CGCAGCTC                 48
```

(2) INFORMATION FOR SEQ ID NO:40:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..66
        (D) OTHER INFORMATION: /product= "LARGE LOOP MUTAGENESIS
            SEQUENCE A"

(xi) SEQUENCE DESCRIPTION: SEQ ID NO:40:

GCCGCCTACT ACTGTNNCNN CNNTNNAANNT NNANNCGGTG GAGGCTCCGG TGCCTTCCCT    60

CTGAAC                                                               66

(2) INFORMATION FOR SEQ ID NO:41:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..66
        (D) OTHER INFORMATION: /product= "LARGE LOOP MUTAGENESIS
            SEQUENCE B"

(xi) SEQUENCE DESCRIPTION: SEQ ID NO:41:

GCCGCCTACT ACTGTNNNNN NNNNNNNNNN NNNTCCGGTG GAGGCTCCGG TGCCTTCCCT    60

CTGAAC                                                               66

(2) INFORMATION FOR SEQ ID NO:42:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..66
        (D) OTHER INFORMATION: /product= "LARGE LOOP MUTAGENESIS
            SEQUENCE C"

(xi) SEQUENCE DESCRIPTION: SEQ ID NO:42:

GCCGCCTACT ACTGTGGCGG CTCTGGAGGT NNANNCNNTN NANNCNNCNN TNNCTTCCCT    60

CTGAAC                                                               66

(2) INFORMATION FOR SEQ ID NO:43:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA -continued

```
    (ix) FEATURE:
          (A) NAME/KEY: misc_feature
          (B) LOCATION: 1..66
          (D) OTHER INFORMATION: /product= "LARGE LOOP MUTAGENESIS
               SEQUENCE D"

(xi) SEQUENCE DESCRIPTION: SEQ ID NO:43:

GCCGCCTACT ACTGTGGCGG CTCTGGAGGT GGANNNNNNN NNNNNNNNNN NNNNTTCCCT     60

CTGAAC                                                                66

(2) INFORMATION FOR SEQ ID NO:44:

(i) SEQUENCE CHARACTERISTICS:
          (A) LENGTH: 4 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:44:

Cys Xaa Cys Xaa
1

(2) INFORMATION FOR SEQ ID NO:45:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:45:

Arg Ala Cys Gly Ser His
1               5
```